United States Patent
Cardia et al.

(10) Patent No.: US 11,021,707 B2
(45) Date of Patent: Jun. 1, 2021

(54) REDUCED SIZE SELF-DELIVERING NUCLEIC ACID COMPOUNDS TARGETING LONG NON-CODING RNA

(71) Applicants: Phio Pharmaceuticals Corp., Marlborough, MA (US); Biogazelle NV, Zwijnaarde (BE)

(72) Inventors: James Cardia, Franklin, MA (US); Karen G. Bulock, Mendon, MA (US); Joke Hedwig Vandesompele, Zwijnaarde (BE); Gert Van Peer, Zwijnaarde (BE)

(73) Assignees: Phio Pharmaceuticals Corp., Marlborough, MA (US); Biogazelle NV, Zwijnaarde (BE)

( * ) Notice: Subject to any disclaimer, the term of this patent is extended or adjusted under 35 U.S.C. 154(b) by 0 days.

(21) Appl. No.: 15/769,555

(22) PCT Filed: Oct. 19, 2016

(86) PCT No.: PCT/US2016/057608
§ 371 (c)(1),
(2) Date: Apr. 19, 2018

(87) PCT Pub. No.: WO2017/070151
PCT Pub. Date: Apr. 27, 2017

(65) Prior Publication Data
US 2019/0048341 A1     Feb. 14, 2019

Related U.S. Application Data

(60) Provisional application No. 62/243,565, filed on Oct. 19, 2015.

(51) Int. Cl.
*C12N 15/113* (2010.01)
*A61K 31/713* (2006.01)
*C12N 15/11* (2006.01)

(52) U.S. Cl.
CPC .......... *C12N 15/113* (2013.01); *A61K 31/713* (2013.01); *C12N 15/111* (2013.01); *C12N 2310/113* (2013.01); *C12N 2310/14* (2013.01); *C12N 2310/315* (2013.01); *C12N 2310/321* (2013.01); *C12N 2310/334* (2013.01); *C12N 2310/335* (2013.01); *C12N 2310/3515* (2013.01); *C12N 2310/50* (2013.01); *C12N 2320/32* (2013.01)

(58) Field of Classification Search
None
See application file for complete search history.

(56) References Cited

U.S. PATENT DOCUMENTS

| 4,201,860 | A | 5/1980 | Naito et al. |
|---|---|---|---|
| 4,235,871 | A | 11/1980 | Papahadjopoulos et al. |
| 4,415,732 | A | 11/1983 | Caruthers et al. |
| 4,426,330 | A | 1/1984 | Sears |
| 4,501,728 | A | 2/1985 | Geho et al. |
| 4,737,323 | A | 4/1988 | Martin et al. |
| 4,810,646 | A | 3/1989 | Jamas et al. |
| 4,837,028 | A | 6/1989 | Allen |
| 4,853,386 | A | 8/1989 | Friebe et al. |
| 4,897,355 | A | 1/1990 | Eppstein et al. |
| 4,904,582 | A | 2/1990 | Tullis |
| 4,958,013 | A | 9/1990 | Letsinger |
| 4,992,540 | A | 2/1991 | Jamas et al. |
| 5,023,243 | A | 6/1991 | Tullis |
| 5,028,703 | A | 7/1991 | Jamas et al. |
| 5,032,401 | A | 7/1991 | Jamas et al. |
| 5,051,257 | A | 9/1991 | Pietronigro |
| 5,082,936 | A | 1/1992 | Jamas et al. |
| 5,112,963 | A | 5/1992 | Pieles et al. |
| 5,151,510 | A | 9/1992 | Stec et al. |
| 5,162,115 | A | 11/1992 | Pietronigro |
| 5,188,897 | A | 2/1993 | Suhadolnik et al. |
| 5,264,423 | A | 11/1993 | Cohen et al. |
| 5,264,562 | A | 11/1993 | Matteucci |
| 5,322,841 | A | 6/1994 | Jamas et al. |
| 5,401,727 | A | 3/1995 | Rorstad et al. |
| 5,405,939 | A | 4/1995 | Suhadolnik |
| 5,414,077 | A | 5/1995 | Lin et al. |
| 5,416,203 | A | 5/1995 | Letsinger |
| 5,417,978 | A | 5/1995 | Tari et al. |
| 5,419,966 | A | 5/1995 | Reed et al. |
| 5,432,272 | A | 7/1995 | Benner |
| 5,453,496 | A | 9/1995 | Caruthers et al. |

(Continued)

FOREIGN PATENT DOCUMENTS

| AU | 2004206255 B2 | 8/2004 |
|---|---|---|
| CN | 1 568 373 A | 1/2005 |

(Continued)

OTHER PUBLICATIONS

[No Author Listed] RedChip Small-Cap Investor Conference. RXI Pharmaceuticals (Nasdaq RXII). Jun. 16, 2009 Presentation. 22 pages.
[No Author Listed] Rxi Pharmaceutical Corporation. Ex 99.1. OTC: RXII. Mar. 2013. 38 pages.
[No Author Listed], Rxi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

(Continued)

*Primary Examiner* — Tracy Vivlemore
(74) *Attorney, Agent, or Firm* — Wolf, Greenfield & Sacks, P.C.

(57) ABSTRACT

The present disclosure relates to RNAi constructs with improved cellular uptake characteristics and methods of use of these compounds for silencing expression of long coding RNAs (lncRNAs).

19 Claims, 3 Drawing Sheets
Specification includes a Sequence Listing.

(56) References Cited

U.S. PATENT DOCUMENTS

| | | |
|---|---|---|
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,504,079 A | 4/1996 | Jamas et al. |
| 5,512,667 A | 4/1996 | Reed et al. |
| 5,514,786 A | 5/1996 | Cook et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,677 A | 3/1997 | Jamas et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,652,359 A | 7/1997 | Meyer, Jr. et al. |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| RE546,678 | 4/1998 | Buhr et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,780,607 A | 7/1998 | Goodnow, Jr. et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,849,902 A | 12/1998 | Arrow et al. |
| 5,851,548 A | 12/1998 | Dattagupta et al. |
| 5,855,910 A | 1/1999 | Ashley et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,968,811 A | 10/1999 | Greenshields |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev |
| 6,153,737 A | 11/2000 | Manoharan et al. |
| 6,207,819 B1 | 3/2001 | Manoharan et al. |
| 6,210,892 B1 | 4/2001 | Bennett et al. |
| 6,242,594 B1 | 6/2001 | Kelly |
| 6,248,878 B1 | 6/2001 | Matulic-Adamic et al. |
| 6,262,241 B1 | 7/2001 | Cook et al. |
| 6,271,358 B1 | 8/2001 | Manoharan et al. |
| 6,326,358 B1 | 12/2001 | Manoharan |
| 6,331,617 B1 | 12/2001 | Weeks et al. |
| 6,335,434 B1 | 1/2002 | Guzaev et al. |
| 6,346,416 B1 | 2/2002 | Dean et al. |
| 6,355,787 B1 | 3/2002 | Beckvermit et al. |
| 6,358,931 B1 | 3/2002 | Cook et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,448 B1 | 9/2002 | Wheatcroft et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,003 B1 | 11/2002 | Jordan et al. |
| 6,476,205 B1 | 11/2002 | Buhr et al. |
| 6,506,559 B1 | 1/2003 | Fire et al. |
| 6,528,631 B1 | 3/2003 | Cook et al. |
| 6,531,584 B1 | 3/2003 | Cook et al. |
| 6,673,611 B2 | 1/2004 | Thompson et al. |
| 6,683,167 B2 | 1/2004 | Meteley et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 6,887,906 B1 | 5/2005 | Teng et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,205,297 B2 | 4/2007 | Beauchamp et al. |
| 7,432,250 B2 | 10/2008 | Crooke |
| 7,538,095 B2 | 5/2009 | Fire et al. |
| 7,560,438 B2 | 7/2009 | Fire et al. |
| 7,595,387 B2 | 9/2009 | Leake et al. |
| 7,605,251 B2 | 10/2009 | Tan et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 8,110,674 B2 | 2/2012 | Manoharan et al. |
| 8,263,569 B2 | 9/2012 | Baulcombe et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |

(56) References Cited

U.S. PATENT DOCUMENTS

| | | |
|---|---|---|
| 10,479,992 B2 | 11/2019 | Woolf et al. |
| 10,633,654 B2 | 4/2020 | Pavco et al. |
| 10,662,430 B2 | 5/2020 | Libertine et al. |
| 10,774,330 B2 | 9/2020 | Khvorova et al. |
| 10,808,247 B2 | 10/2020 | Byrne et al. |
| 10,815,485 B2 | 10/2020 | Khvorova et al. |
| 2002/0049173 A1 | 4/2002 | Bennett et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0216346 A1 | 11/2003 | Sakurai et al. |
| 2004/0009938 A1 | 1/2004 | Manoharan et al. |
| 2004/0014715 A1 | 1/2004 | Ostroff |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0063654 A1 | 4/2004 | Davis et al. |
| 2004/0072785 A1 | 4/2004 | Wolff et al. |
| 2004/0102618 A1 | 5/2004 | Crooke et al. |
| 2004/0137471 A1 | 7/2004 | Vickers et al. |
| 2004/0162235 A1 | 8/2004 | Trubetskoy et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0229266 A1 | 11/2004 | Tuschl et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0020521 A1 | 1/2005 | Rana |
| 2005/0026286 A1 | 2/2005 | Chi et al. |
| 2005/0032733 A1 | 2/2005 | McSwiggen et al. |
| 2005/0037496 A1 | 2/2005 | Rozema et al. |
| 2005/0042227 A1 | 2/2005 | Zankel et al. |
| 2005/0064595 A1 | 3/2005 | MacLachlan et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0181382 A1 | 8/2005 | Zamore et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2005/0265957 A1 | 12/2005 | Monahan et al. |
| 2005/0281781 A1 | 12/2005 | Ostroff |
| 2006/0008910 A1 | 1/2006 | MacLachlan et al. |
| 2006/0009409 A1 | 1/2006 | Woolf |
| 2006/0069050 A1 | 3/2006 | Rana |
| 2006/0142228 A1 | 6/2006 | Ford et al. |
| 2006/0178324 A1 | 8/2006 | Hadwiger et al. |
| 2006/0178327 A1 | 8/2006 | Yeung |
| 2006/0211766 A1 | 9/2006 | Kaplan et al. |
| 2006/0240093 A1 | 10/2006 | MacLachlan et al. |
| 2007/0032441 A1 | 2/2007 | McSwiggen et al. |
| 2007/0166734 A1 | 7/2007 | Bhat et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0038296 A1 | 2/2008 | Brahmbhatt et al. |
| 2008/0071068 A1 | 3/2008 | Oba et al. |
| 2008/0085869 A1 | 4/2008 | Yamada et al. |
| 2008/0107694 A1 | 5/2008 | Trogden et al. |
| 2008/0112916 A1 | 5/2008 | Wagner et al. |
| 2008/0152661 A1 | 6/2008 | Rozema et al. |
| 2008/0311040 A1 | 12/2008 | Berry et al. |
| 2009/0023216 A1 | 1/2009 | Woolf |
| 2009/0131360 A1 | 5/2009 | Woolf et al. |
| 2009/0208564 A1 | 8/2009 | Li et al. |
| 2009/0247608 A1 | 10/2009 | Manoharan et al. |
| 2009/0306005 A1 | 12/2009 | Bhanot et al. |
| 2010/0040656 A1 | 2/2010 | Franklin et al. |
| 2010/0069620 A1 | 3/2010 | Zon |
| 2010/0136695 A1 | 6/2010 | Woolf |
| 2011/0039914 A1 | 2/2011 | Pavco et al. |
| 2011/0237522 A1 | 9/2011 | Khvorova et al. |
| 2011/0251258 A1 | 10/2011 | Samarsky et al. |
| 2011/0268761 A1 | 11/2011 | Levis et al. |
| 2011/0294869 A1 | 12/2011 | Petersen |
| 2012/0040459 A1* | 2/2012 | Khvorova ............ C12N 15/111 435/375 |
| 2014/0364482 A1 | 12/2014 | Khvorova et al. |
| 2015/0057362 A1 | 2/2015 | Levis et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0051288 A1 | 2/2017 | Byrne et al. |
| 2017/0051290 A1 | 2/2017 | Byrne et al. |
| 2017/0137823 A1 | 5/2017 | Kamens et al. |
| 2018/0030451 A1 | 2/2018 | Cauwenbergh |
| 2018/0155718 A1 | 6/2018 | Woolf et al. |
| 2018/0195066 A1 | 7/2018 | Byrne et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0161757 A1 | 5/2019 | Khvorova et al. |
| 2019/0169608 A1 | 6/2019 | Pavco et al. |
| 2019/0211337 A1 | 7/2019 | Khvorova et al. |
| 2019/0218557 A1 | 7/2019 | Kamens et al. |
| 2019/0233826 A1 | 8/2019 | Libertine et al. |
| 2020/0002701 A1 | 1/2020 | Khvorova et al. |
| 2020/0085764 A1 | 3/2020 | Maxwell et al. |
| 2020/0101028 A1 | 4/2020 | Levis et al. |
| 2020/0215113 A1 | 7/2020 | Eliseev |
| 2020/0308578 A1 | 10/2020 | Woolf et al. |

FOREIGN PATENT DOCUMENTS

| | | |
|---|---|---|
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | 4 095 895 B2 | 9/2004 |
| JP | 2007-525169 A | 9/2007 |
| JP | 2007-531520 A | 11/2007 |
| JP | 2009-519033 | 5/2009 |
| JP | 2013-538561 A | 10/2013 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/08003 A1 | 4/1994 |
| WO | WO 94/23028 A2 | 10/1994 |
| WO | WO 95/11910 A1 | 5/1995 |
| WO | WO 95/22553 A1 | 8/1995 |
| WO | WO 95/23162 A1 | 8/1995 |
| WO | WO 96/40964 A2 | 12/1996 |
| WO | WO 02/12348 A2 | 2/2002 |
| WO | WO 03/012052 A2 | 2/2003 |
| WO | WO 2003/064626 A2 | 8/2003 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/079533 A2 | 9/2005 |
| WO | WO 2005/097992 A2 | 10/2005 |

(56) References Cited

FOREIGN PATENT DOCUMENTS

| WO | WO 2006/007372 A2 | 1/2006 |
|---|---|---|
| WO | WO 2006/019430 A2 | 2/2006 |
| WO | WO 2006/039656 A2 | 4/2006 |
| WO | WO 2006/065601 A2 | 6/2006 |
| WO | WO 2006/128141 A2 | 11/2006 |
| WO | WO 2007/030167 A1 | 3/2007 |
| WO | WO 2007/050643 A2 | 5/2007 |
| WO | WO 2007/069068 A2 | 6/2007 |
| WO | WO 2007/089607 A2 | 8/2007 |
| WO | WO 2008/021157 A1 | 2/2008 |
| WO | WO 2008/036825 A2 | 3/2008 |
| WO | WO 2008/109353 A1 | 9/2008 |
| WO | WO 2009/020344 A2 | 2/2009 |
| WO | WO 2009/021157 A1 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/126933 A2 | 10/2009 |
| WO | WO 2009/134487 A2 | 11/2009 |
| WO | WO 2010/006237 A2 | 1/2010 |
| WO | WO 2010/011346 A1 | 1/2010 |
| WO | WO 2010/027830 A2 | 3/2010 |
| WO | WO 2010/042281 A2 | 4/2010 |
| WO | WO 2012/018881 A2 | 2/2012 |
| WO | WO 2015/024986 A1 | 2/2015 |

OTHER PUBLICATIONS

Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Aleckovic et al., J RNAi Gene Silencing. May 27, 2008;4(1):266-8.
Amaral et al., lncRNAdb: a reference database for long noncoding RNAs. Nucleic Acids Res. Jan. 2011;39(Database issue):D146-51. doi: 10.1093/nar/gkq1138. Epub Nov. 25, 2010.
Augustyns et al., Incorporation of hexose nucleoside analogues into oligonucleotides: synthesis, base-pairing properties and enzymatic stability. Nucleic Acids Res. Sep. 25, 1992;20(18):4711-6.
Baigude et al., Design and creation of new nanomaterials for therapeutic RNAi. ACS Chem Biol. Apr. 24, 2007;2(4):237-41.
Bergan et al., Electroporation enhances c-myc antisense oligodeoxynucleotide efficacy. Nucleic Acids Res. Jul. 25, 1993;21(15):3567-73.
Bertrand et al., Comparison of antisense oligonucleotides and siRNAs in cell culture and in vivo. Biochem Biophys Res Commun. Aug. 30, 2002;296(4):1000-4.
Bongartz et al., Improved biological activity of antisense oligonucleotides conjugated to a fusogenic peptide. Nucleic Acids Res. Nov. 11, 1994;22(22):4681-8.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA interference in mammalian cells by chemically-modified RNA. Biochemistry. Jul. 8, 2003;42(26):7967-75.
Brown et al., RNAi off-targeting: Light at the end of the tunnel. J RNAi Gene Silencing. Jul. 28, 2006;2(2):175-7.
Bunnell et al., Targeted delivery of antisense oligonucleotides by molecular conjugates. Somat Cell Mol Genet. Nov. 1992;18(6):559-69.
Cardia et al., Novel self-delivering RNAi compounds with enhanced cellular updatake and distribution properties. Keystone RNAi Silencing Conference. Jan. 14-19, 2010. Poster. 1 Page.
Caruthers et al., Chemical and biochemical studies with dithioate DNA. Nucleosides & Nucleotides. 1991;10(1-3):47-59.
Chen et al., Constructing lncRNA functional similarity network based on lncRNA-disease associations and disease semantic similarity. Sci Rep. Jun. 10, 2015;5:11338. doi: 10.1038/srep11338.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.
Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.
Chiang et al., Antisense oligonucleotides inhibit intercellular adhesion molecule 1 expression by two distinct mechanisms. J Biol Chem. Sep. 25, 1991;266(27):18162-71.
Chiu et al., siRNA function in RNAi: a chemical modification analysis. RNA. Sep. 2003;9(9):1034-48.
Choung et al., Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Czauderna et al., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Dykxhoorn et al., The silent treatment: siRNAs as small molecule drugs. Gene Ther. Mar. 2006;13(6):541-52. Review.
Eichelbaum et al., Influence of pharmacogenetics on drug disposition and response. Clin Exp Pharmacol Physiol. Oct.-Nov. 1996;23(10-11):983-5. Review.
Eissmann et al., Loss of the abundant nuclear non-coding RNA MALAT1 is compatible with life and development. RNA Biol. Aug. 2012;9(8):1076-87. doi: 10.4161/rna.21089. Epub Aug. 1, 2012.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Fisher et al., Intracellular disposition and metabolism of fluorescently-labeled unmodified and modified oligonucleotides microinjected into mammalian cells. Nucleic Acids Res. Aug. 11, 1993;21(16):3857-65.
Flanagan et al., A cytosine analog that confers enhanced potency to antisense oligonucleotides. Proc Natl Acad Sci U S A. Mar. 30, 1999;96(7):3513-8.
Geisler et al., RNA in unexpected places: long non-coding RNA functions in diverse cellular contexts. Nat Rev Mol Cell Biol. Nov. 2013;14(11):699-712. doi: 10.1038/nrm3679. Epub Oct. 9, 2013. Review. Author manuscript.
Glaser, Oligonucleotide therapies move toward efficacy trials to treav HIV CMV, cancer. Genetic Engineering News. Feb. 1, 2016;16:1-21.
Goodrich et al., Non-coding-RNA regulators of RNA polymerase II transcription. Nat Rev Mol Cell Biol. Aug. 2006;7(8):612-6. Epub May 24, 2006.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Hope et al., Cationic lipids, phosphatidylethanolamine and the intracellular delivery of polymeric, nucleic acid-based drugs (review). Mol Membr Biol. Jan.-Mar. 1998;15(1):1-14.
Hudziak et al., Resistance of morpholino phosphorodiamidate oligomers to enzymatic degradation. Antisense Nucleic Acid Drug Dev. 1996 Winter;6(4):267-72.

(56) References Cited

OTHER PUBLICATIONS

Iyer et al., The landscape of long noncoding RNAs in the human transcriptome. Nat Genet. Mar. 2015;47(3):199-208. doi: 10.1038/ng.3192. Epub Jan. 19, 2015. Author manuscript.

Jackson et al., Position-specific chemical modification of siRNAs reduces "off-target" transcript silencing. RNA. Jul. 2006;12(7):1197-1205. Epub May 8, 2006.

Kamens et al., Novel, chemically modified RNAi compounds with improved potency, stability and specificity. Keystone RNAi Silencing: Mechanism, Biology and Application Conference. Jan. 14-19, 2010. Poster. 1 Page.

Kawasaki et al., Uniformly modified 2'-deoxy-2'-fluoro phosphorothioate oligonucleotides as nuclease-resistant antisense compounds with high affinity and specificity for RNA targets. J Med Chem. Apr. 2, 1993;36(7):831-41.

Kim et al., Systemic and specific delivery of small interfering RNAs to the liver mediated by apolipoprotein A-I. Mol Ther. Jun. 2007;15(6):1145-52. Epub Apr. 17, 2007.

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.

Kubo et al., Modified 27-nt dsRNAs with dramatically enhanced stability in serum and long-term RNAi activity. Oligonucleotides. 2007 Winter;17(4):445-64.

Layzer et al., In vivo activity of nuclease-resistant siRNAs. RNA. May 2004;10(5):766-71.

Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.

Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.

Leuschner et al., Cleavage of the siRNA passenger strand during RISC assembly in human cells. EMBO Reports 2006;7(3):314-20.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Surface-modified LPD nanoparticles for tumor targeting. Ann N Y Acad Sci. Oct. 2006;1082:1-8.

Li et al., Yeast glucan particles activate murine resident macrophages to secrete proinflammatory cytokines via MyD88- and Syk kinase-dependent pathways. Clin Immunol. Aug. 2007;124(2):170-81. Epub Jun. 14, 2007.

Liu et al., Pathogenic role of lncRNA-MALAT1 in endothelial cell dysfunction in diabetes mellitus. Cell Death Dis. Oct. 30, 2014;5:e1506. doi: 10.1038/cddis.2014.466.

Manoharan et al., Chemical modifications to improve uptake and bioavailability of antisense oligonucleotides. Ann N Y Acad Sci. Oct. 28, 1992;660:306-9.

Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.

Martins et al., Sterol side chain length and structure affect the clearance of chylomicron-like lipid emulsions in rats and mice. J Lipid Res. Feb. 1998;39(2):302-12.

Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.

Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.

Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.

Opalinska et al., Nucleic-acid therapeutics: basic principles and recent applications. Nat Rev Drug Discov. Jul. 2002;1(7):503-14.

Ortigão et al., Antisense effect of oligodeoxynucleotides with inverted terminal internucleotidic linkages: a minimal modification protecting against nucleolytic degradation. Antisense Res Dev. 1992 Summer;2(2):129-46.

Overhoff et al., Phosphorothioate-stimulated uptake of short interfering RNA by human cells. EMBO Rep. Dec. 2005;6(12):1176-81.

Parrish et al., Functional anatomy of a dsRNA trigger: differential requirement for the two trigger strands in RNA interference. Mol Cell. Nov. 2000;6(5):1077-87.

Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.

Rajeev et al., 2'-modified-2-thiothymidine oligonucleotides. Org Lett. Aug. 21, 2003;5(17):3005-8.

Reichhart et al., Splice-activated UAS hairpin vector gives complete RNAi knockout of single or double target transcripts in *Drosophila melanogaster*. Genesis. Sep.-Oct. 2002;34(1-2):160-4.

Rozners et al., Expanding functionality of RNA: synthesis and properties of RNA containing imidazole modified tandem G-U wobble base pairs. Chem Commun (Camb). Dec. 14, 2005;(46):5778-80.

Rump et al., Preparation of conjugates of oligodeoxynucleotides and lipid structures and their interaction with low-density lipoprotein. Bioconjug Chem. May-Jun. 1998;9(3):341-9.

Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.

Sato et al., Tumor targeting and imaging of intraperitoneal tumors by use of antisense oligo-DNA complexed with dendrimers and/or avidin in mice. Clin Cancer Res. Nov. 2001;7(11):3606-12.

Seela et al., Oligodeoxyribonucleotides containing 1,3-propanediol as nucleoside substitute. Nucleic Acids Res. Apr. 10, 1987;15(7):3113-29.

Shi, Mammalian RNAi for the masses. Trends Genet. Jan. 2003;19(1):9-12.

Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.

Snead et al., RNA interference trigger variants: getting the most out of RNA for RNA interference-based therapeutics. Nucleic Acid Ther. Jun. 2012;22(3):139-46. doi: 10.1089/nat.2012.0361. Review.

Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.

Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.

Soutschek et al., Therapeutic silencing of an endogenous gene by systemic administration of modified siRNAs. Nature. Nov. 11, 2004;432(7014):173-8.

Stein et al., A specificity comparison of four antisense types: morpholino, 2'-O-methyl RNA, DNA, and phosphorothioate DNA. Antisense Nucleic Acid Drug Dev. Jun. 1997;7(3):151-7.

Sui et al., A DNA vector-based RNAi technology to suppress gene expression in mammalian cells. Proc Natl Acad Sci U S A. Apr. 16, 2002;99(8):5515-20.

Summerton et al., Morpholino and phosphorothioate antisense oligomers compared in cell-free and in-cell systems. Antisense Nucleic Acid Drug Dev. Apr. 1997;7(2):63-70.

(56) References Cited

OTHER PUBLICATIONS

Summerton et al., Morpholino antisense oligomers: design, preparation, and properties. Antisense Nucleic Acid Drug Dev. Jun. 1997;7(3):187-95. Review.

Summerton, Morpholino antisense oligomers: the case for an RNase H-independent structural type. Biochim Biophys Acta. Dec. 1999;1489(1):141-58. Review.

Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.

Tiedge et al., Dendritic location of neural BC1 RNA. Proc Natl Acad Sci U S A. Mar. 15, 1991;88(6):2093-7.

Uhlmann et al., Antisense oligonucleotides: a new therapeutic principle. Chem Rev. 1990;90(4):543-84.

Vaught et al., Expanding the chemistry of DNA for in vitro selection. J Am Chem Soc. Mar. 31, 2010;132(12):4141-51. doi: 10.1021/ja908035g.

Vlassov et al., Transport of oligonucleotides across natural and model membranes. Biochim Biophys Acta. Jun. 29, 1994;1197(2):95-108.

Wagner et al., Transferrin-polycation-DNA complexes: the effect of polycations on the structure of the complex and DNA delivery to cells. Proc Natl Acad Sci U S A. May 15, 1991;88(10):4255-9.

Wolfrum et al., Mechanisms and optimization of in vivo delivery of lipophilic siRNAs. Nat Biotechnol. Oct. 2007;25(10):1149-57. Epub Sep. 16, 2007.

Wutz et al., Chromosomal silencing and localization are mediated by different domains of Xist RNA. Nat Genet. Feb. 2002;30(2):167-74. Epub Jan. 7, 2002.

Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.

Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.

Cardia et al., Self-Delivering RNAi Compounds. Drug Delivery Technology. Sep. 2010;10(7):1-4.

Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.

Chernikov et al., Current Development of siRNA Bioconjugates: From Research to the Clinic. Front Pharmacol. Apr. 26, 2019;10:444. doi: 10.3389/fphar.2019.00444.

Sibley et al. Novel RNA-based strategies for therapeutic gene silencing. Mol Ther. Mar. 2010;18(3):466-76. doi: 10.1038/mt.2009.306. Epub Jan. 19, 2010.

\* cited by examiner

US 11,021,707 B2

REDUCED SIZE SELF-DELIVERING NUCLEIC ACID COMPOUNDS TARGETING LONG NON-CODING RNA

RELATED APPLICATIONS

This application is a national stage filing under 35 U.S.C. § 371 of International Application No. PCT/US2016/057608, filed Oct. 19, 2016, entitled "REDUCED SIZE SELF-DELIVERING NUCLEIC ACID COMPOUNDS TARGETING LONG NON-CODING RNA" which was published under PCT Article 21(2) in English and which claims the benefit under 35 U.S.C. 119(e) of U.S. Provisional Application Ser. No. 62/243,565, filed on Oct. 19, 2015, entitled "REDUCED SIZE SELF-DELIVERING NUCLEIC ACID COMPOUNDS TARGETING LONG NONCODING RNA", the entire contents of each of which are incorporated herein by reference.

FIELD OF THE INVENTION

The invention relates, at least in part, to the use of nucleic acid molecules with improved in vivo delivery properties and their use to reduce the expression of long non-coding RNAs (lncRNAs).

BACKGROUND OF THE INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition or increase of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oligonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds impaired to be inhibited in the presence of biological fluids resulting in highly limited efficacy in gene silencing in vivo, limiting the applicability of these compounds in a clinical setting.

Following the sequencing of the mammalian genome, ~20,000 protein-coding genes were identified; however, 99% of the genome was thought to contain non-functional and repetitive sequences. More recently, researchers utilizing transcriptome profiling approaches have discovered that ~60,000 of these non-functional sequences of the genome are transcribed into long non-coding RNAs (lncRNAs), many of which are functional (Iyer et al. (2015)). Long non-coding RNAs (lncRNAs), containing >200 nucleotides, were found to function in the following biological processes: cell proliferation, differentiation, regulation of transcription, epigenetic regulation, post transcriptional regulation, organization of protein complexes, cell to cell communication and allosteric regulation of proteins (Chen, 2015; Geisler et al. 2013).

lncRNAs can be located throughout the cell; however, a majority of lncRNAs are localized in the nucleus (Cabili, 2015). Considering the machinery for RNAi is located in the cytoplasm and not the nucleus, it is believed that using RNAi compounds to reduce levels of lncRNAs (located in the nucleus) would not work. Indeed, researchers have shown that siRNAs can be used to target cytoplasmic-based lncRNAs; however, they have not been demonstrated to work to target nuclear lncRNAs.

SUMMARY

The present disclosure provides compositions and methods for the silencing of lncRNAs. The invention is based, at least in part, on the surprising discovery that self-delivering RNAi compounds are able to robustly and potently reduce levels of lncRNAs in cells, both in the cytoplasm and nucleus. Silencing of nuclear lncRNAs by the RNAi compounds described herein is particularly surprising since it had previously been demonstrated that siRNAs could be used to target cytoplasmic based lncRNAs, but not nuclear lncRNAs. Furthermore, self-delivering RNAi compounds described herein surprisingly mediate silencing of nuclear targets without the use of delivery vehicles (e.g., lipid-mediated transfection agents).

Accordingly, in some aspects, the disclosure provides an isolated, double stranded nucleic acid molecule comprising a guide strand of 18-23 nucleotides in length that has complementarity to a lncRNA sequence, and a passenger strand of 8-16 nucleotides in length, wherein the molecule comprises a double stranded region and a single stranded region, wherein the single stranded region is the 3' end of the guide strand, is 2-13 nucleotides in length, and comprises at least two phosphorothioate modifications, and wherein at least 50% of the pyrimidines in the nucleic acid molecule are modified.

In some embodiments, the first nucleotide relative to the 5'end of the guide strand has a 2'-O-methyl modification, optionally wherein the 2'-O-methyl modification is a 5P-2'O-methyl U modification, or a 5' vinyl phosphonate 2'-O-methyl U modification.

In some embodiments, at least 60%, at least 80%, at least 90% or wherein 100% of the pyrimidines in the nucleic acid molecule are modified. In some embodiments, the modified pyrimidines are 2'-fluoro or 2'-O-methyl modified.

In some embodiments, at least one U or C includes a hydrophobic modification, optionally wherein a plurality of U's and/or C's include a hydrophobic modification. In some embodiments, the hydrophobic modification is a methyl or ethyl hydrophobic base modification.

In some embodiments, the guide strand comprises 6-8 phosphorothioate modifications. In some embodiments, the guide strand comprises at least eight phosphorothioate modifications located within the first 10 nucleotides relative to the 3'end of the guide strand. In some embodiments, the guide strand includes 4-14 phosphate modifications. In some embodiments, the single stranded region of the guide strand is 6 nucleotides long to 8 nucleotides long.

In some embodiments, the double stranded region is 13 nucleotides long. In some embodiments, the double stranded nucleic acid molecule has one end that is blunt or includes a one nucleotide overhang.

In some embodiments, the passenger strand is linked at the 3' end to a lipophilic group. In some embodiments, the lipophilic group is a sterol, optionally wherein the sterol is cholesterol.

In some embodiments, the isolated double stranded nucleic acid molecule is an sd-rxRNA and wherein the guide strand is complementary to a lncRNA, optionally wherein the lncRNA is selected from the group consisting of ENST00000585065, ENST00000602414, ENST00000607352, ENST00000456581, ENST00000340510, ENST00000605920, ENST00000455699, ENST00000555578, ENST00000565493, ENST00000580048 and MALAT1.

In some embodiments, the isolated double stranded nucleic acid molecule is an sd-rxRNA and wherein the guide strand is complementary to MALAT1.

In some embodiments, the isolated double stranded nucleic acid molecule is a lncRNA inhibitor and wherein the lncRNA sequence to which the guide strand is complementary is an antisense strand of a mature lncRNA. In some embodiments, the guide strand of a double stranded nucleic acid molecule lncRNA inhibitor is at least 50% chemically modified.

In some embodiments, the nucleic acid molecule is directed against at least 12 contiguous nucleotides of a sequence within Table 1 or Table 2.

In some aspects, the disclosure provides a method for modulating lncRNA expression and/or activity in a cell, comprising contacting a cell with a double stranded nucleic acid molecule as described herein (e.g., an sd-rxRNA) in an amount effective to modulate lncRNA expression and/or activity.

In some embodiments of the method, the lncRNA is localized in the nucleus of the cell. In some embodiments, of the method, the lncRNA is localized in the cytoplasm of the cell. In some embodiments of the method, the lncRNA is localized both in the nucleus and the cytoplasm of the cell. In some embodiments, the cell is a bacterial cell or a eukaryotic cell. In some embodiments, the eukaryotic cell is selected from the group consisting of plant cell, arthropod cell, and animal cell). In some embodiments, the eukaryotic cell is a mammalian cell, such as a human cell. In some embodiments, the cell is a stem cell, optionally a human stem cell.

In some embodiments of the method, the cell is contacted with the isolated nucleic acid molecule in vivo or ex vivo.

In some aspects, the disclosure relates to double stranded molecules configured to treat diseases associated with dysregulation of lncRNA expression. Dysregulation or alteration in lncRNAs levels has been shown to be associated with the progression of many diseases including: cancers (lung, breast, prostate, hepatocellular carcinoma, etc.), cardiovascular diseases, neurological disorders, diabetes, and HIV. Therefore in some embodiments, the disclosure provides a method of treating a subject having a disease associated with dysregulation of lncRNA expression, the method comprising administering to the subject a double stranded nucleic acid molecule as described herein in an amount effective to modulate the expression level or activity of a target lncRNA.

Without wishing to be bound by any particular theory, the sense strand of the double stranded molecules described herein (e.g., sd-rxRNA sense strand) is not limited to delivery of the guide strand of the double stranded nucleic acid molecule. Rather, in some embodiments, a passenger strand described herein is joined (e.g., covalently bound, non-covalently bound, conjugated, etc.) to certain molecules (e.g., antisense oligonucleotides, ASO) for the purpose of targeting said other molecule to the nucleus of a cell. Accordingly, in some aspects, the disclosure provides a method of delivering a nucleic acid molecule to a cell, the method comprising administering an isolated nucleic acid molecule to a cell, wherein the isolated nucleic acid comprises a sense strand which is complementary to an antisense oligonucleotide (ASO), wherein the sense strand is between 8-15 nucleotides in length, comprises at least two phosphorothioate modifications, at least 50% of the pyrimidines in the sense strand are modified, and wherein the molecule comprises a hydrophobic conjugate.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

Figure 1:
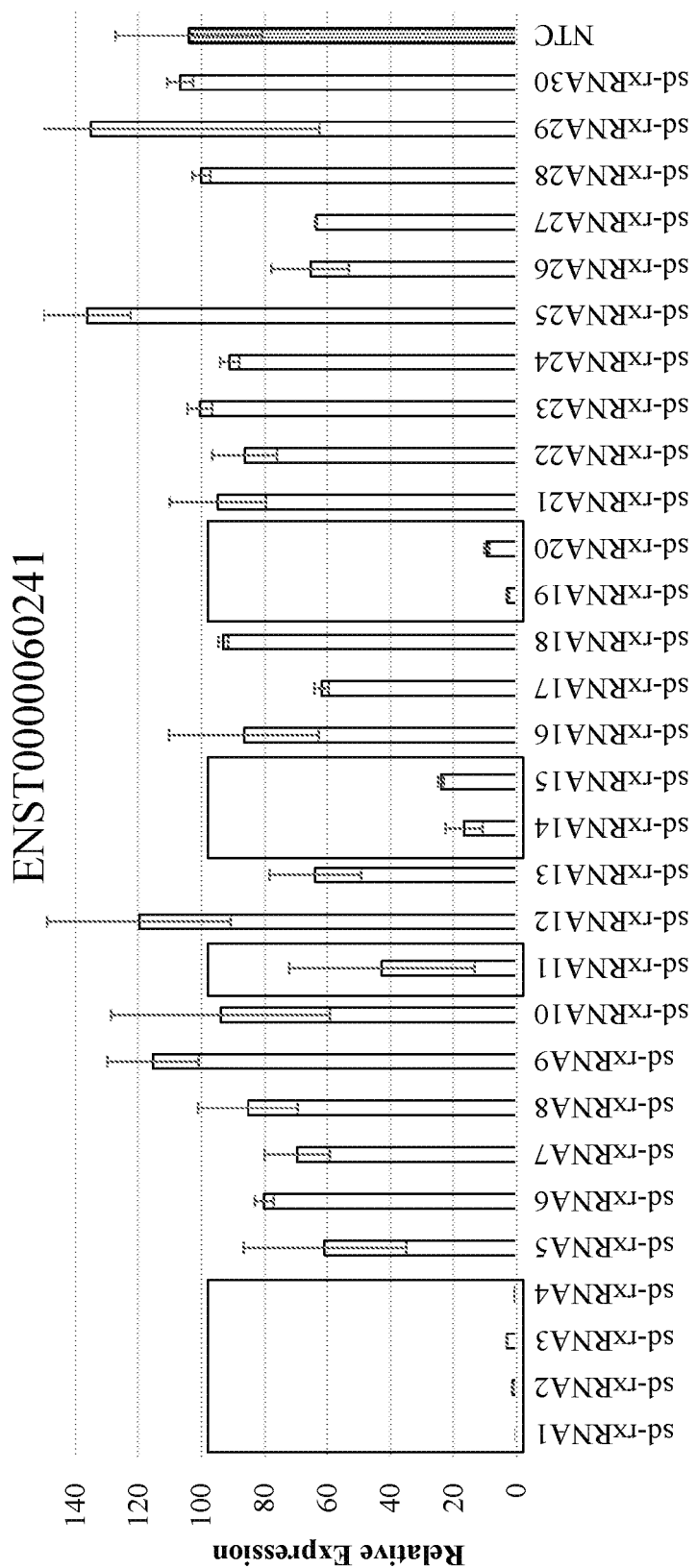
FIG. 1 shows the identification of potent sd-rxRNAs targeting lncRNA (ENST0000060241). sd-rxRNAs were screened against 11 lncRNA targets. Potent sd-rxRNAs (>60% silencing) for 10 out of 11 lncRNAs, with an overall hit rate of 21% were identified. The lncRNA-targeting sd-rxRNAs described in this particular assay significantly reduced target gene lncRNA levels in vitro in a human hepatocarcinoma cell line.

The present disclosure relates, in part, to compositions and methods for the silencing of long non-coding RNAs (lncRNAs) by double stranded nucleic acid molecules.

As used herein, a "long non-coding RNA" or "lncRNA" refers to a transcribed RNA molecule containing greater than 200 nucleotides that do not code for protein. LncRNAs are usually located within intergenic spaces of the genome.

Generally, lncRNAs are a diverse class of molecules that play a variety of roles in modulation of gene function. For example lncRNAs are known to regulate gene transcription (for example, as described by Goodrich et al. *Nature Reviews Molecular Cell Biology*, 7 (8): 612-6, 2006), translation (for example, as described by Tiedge et al. *PNAS* 88:(6): 2093-7, 1991), and epigenetic regulation (for example, as described by Wutz et al. *Nature Genetics*, 30 (2): 167-74, 2002). Examples of lncRNAs include, but are not limited to Kcnq1ot1, Xlsirt, Xist, ANRIL and MALAT1. Further examples of lncRNAs are described, for example, in Amaral et al. *Nucleic Acids Research* 39((Database issue)): D146-D151, (2010).

The disclosure is based, at least in part, on the surprising discovery that the double stranded nucleic acid molecules described herein are able to robustly and potently reduce levels of long non-coding RNAs (lncRNAs) in cells, both in the cytoplasm and nucleus. Silencing of nuclear lncRNAs by the molecules described herein is particularly surprising in light of the fact that the prior art has demonstrated that siRNAs were not effective in targeting nuclear lncRNAs.

Accordingly, in some aspects, the disclosure provides an isolated, double stranded nucleic acid molecule comprising a guide strand of 18-23 nucleotides in length that has complementarity to a lncRNA sequence, and a passenger strand of 8-16 nucleotides in length, wherein the molecule comprises a double stranded region and a single stranded region, wherein the single stranded region is the 3' end of the guide strand, is 2-13 nucleotides in length, and comprises at least two phosphorothioate modifications, and wherein at least 50% of the pyrimidines in the nucleic acid molecule are modified.

As used herein, "nucleic acid molecule" includes but is not limited to: sd-rxRNA, rxRNAori, oligonucleotides, ASO, siRNA, shRNA, miRNA, ncRNA, cp-lasiRNA, aiRNA, BMT-101, RXI-109, EXC-001, single-stranded nucleic acid molecules, double-stranded nucleic acid molecules, RNA and DNA. In some embodiments, the nucleic acid molecule is a chemically modified nucleic acid molecule, such as a chemically modified oligonucleotide. Double stranded nucleic acid molecules of the invention are described in further detail below and in the Examples section.

Without wishing to be bound by any theory, dysregulation or alteration in lncRNAs levels has been shown to be associated with the progression of many diseases including: cancers (lung, breast, prostate, hepatocellular carcinoma, etc.), cardiovascular diseases, neurological disorders, diabetes, and HIV (Chen, 2015). Therefore in some embodiments, the disclosure provides a method of treating a subject having a disease associated with dysregulation of lncRNA expression, the method comprising administering to the subject a double stranded nucleic acid molecule as described herein in an amount effective to modulate the expression level or activity of a target lncRNA.

Sd-rxRNA Molecules

Aspects of the invention relate to sd-rxRNA molecules. As used herein, an "sd-rxRNA" or an "sd-rxRNA molecule" refers to a self-delivering RNA molecule such as those described in, and incorporated by reference from, U.S. Pat. No. 8,796,443, granted on Aug. 5, 2014, entitled "REDUCED SIZE SELF-DELIVERING RNAI COMPOUNDS", U.S. Pat. No. 9,175,289, granted on Nov. 3, 2015, entitled "REDUCED SIZE SELF-DELIVERING RNAI COMPOUNDS", and PCT Publication No. WO2010/033247 (Application No. PCT/US2009/005247), filed on Sep. 22, 2009, and entitled "REDUCED SIZE SELF-DELIVERING RNAI COMPOUNDS." Briefly, an sd-rxRNA, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. sd-rxRNA molecules can be optimized through chemical modification, and in some instances through attachment of hydrophobic conjugates.

In some embodiments, an sd-rxRNA comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

The polynucleotides of the invention are referred to herein as isolated double stranded or duplex nucleic acids, oligonucleotides or polynucleotides, nano molecules, nano RNA, sd-rxRNA$^{nano}$, sd-rxRNA or RNA molecules of the invention.

sd-rxRNAs are much more effectively taken up by cells compared to conventional siRNAs. These molecules are highly efficient in silencing of target gene expression and offer significant advantages over previously described RNAi molecules including high activity in the presence of serum, efficient self-delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. sd-rxRNAs however, although partially double-stranded, are recognized in vivo as single-stranded and, as such, are capable of efficiently being delivered across cell membranes. As a result the polynucleotides of the invention are capable in many instances of self-delivery. Thus, the polynucleotides of the invention may be formulated in a manner similar to conventional RNAi agents or they may be delivered to the cell or subject alone (or with non-delivery type carriers) and allowed to self-deliver. In one embodiment of the present invention, self-delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. In some embodiments, this class of RNAi like compounds have superior efficacy in vitro and in vivo. It is believed that the reduction in the size of the rigid duplex region in combination with phosphorothioate modifications applied to a single stranded region contribute to the observed superior efficacy.

Methods of effectively administering sd-rxRNA to the skin and silencing gene expression have been demonstrated in U.S. Pat. No. 8,664,189, granted on Mar. 4, 2014 and entitled "RNA INTERFERENCE IN SKIN INDICATIONS," US Patent Publication No. US2014/0113950, filed on Apr. 4, 2013 and entitled "RNA INTERFERENCE IN DERMAL AND FIBROTIC INDICATIONS," PCT Publication No. WO 2010/033246, filed on Sep. 22, 2009 and entitled "RNA INTERFERENCE IN SKIN INDICATIONS" and PCT Publication No. WO2011/119887, filed on Mar. 24, 2011 and entitled "RNA INTERFERENCE IN DERMAL AND FIBROTIC INDICATIONS." Each of the above-referenced patents and publications are incorporated by reference herein in their entireties.

It should be appreciated that the sd-rxRNA molecules disclosed herein can be administered to the skin in the same manner as the sd-rxRNA molecules disclosed in US Patent Publication No. US2014/0113950, incorporated by reference in its entirety.

In a preferred embodiment the RNAi compounds of the invention comprise an asymmetric compound comprising a duplex region (required for efficient RISC entry of 8-15 bases long) and single stranded region of 4-12 nucleotides long. In some embodiments, the duplex region is 13 or 14 nucleotides long. A 6 or 7 nucleotide single stranded region is preferred in some embodiments. The single stranded region of the new RNAi compounds also comprises 2-12 phosphorothioate internucleotide linkages (referred to as phosphorothioate modifications). 6-8 phosphorothioate internucleotide linkages are preferred in some embodiments. Additionally, the RNAi compounds of the invention also include a unique chemical modification pattern, which provides stability and is compatible with RISC entry. In some embodiments, the combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes O-methyl modification of C and U nucleotides within the passenger strand or alternatively the passenger strand may be completely O-methyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2'O-methyl modification of position 1 and C/U in positions 11-18 and 5' end chemical phosphorylation. Yet another preferred chemical modification pattern in the guide strand includes 2'O-methyl modification of position 1 and C/U in positions 11-18 and 5' end chemical phosphorylation and 2'F modification of C/U in positions 2-10. In some embodiments the passenger strand and/or the guide strand contains at least one 5-methyl C or U modifications.

In some embodiments, at least 30% of the nucleotides in the sd-rxRNA are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-rxRNA are modified. In some embodiments, 100% of the nucleotides in the sd-rxRNA are modified.

The above-described chemical modification patterns of the oligonucleotides of the invention are well tolerated and actually improved efficacy of asymmetric RNAi compounds. In some embodiments, elimination of any of the described components (Guide strand stabilization, phosphorothioate stretch, sense strand stabilization and hydrophobic conjugate) or increase in size in some instances results in sub-optimal efficacy and in some instances complete loss of efficacy. The combination of elements results in development of a compound, which is fully active following passive delivery to cells such as HeLa cells.

The sd-rxRNA can be further improved in some instances by improving the hydrophobicity of compounds using of novel types of chemistries. For example, one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. A version of sd-rxRNA compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake prosperities in vivo.

dsRNA formulated according to the invention also includes rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF," and US Patent Publication No. 2011/0039914, filed on Nov. 1, 2010, and entitled "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA are modified. In some embodiments, only the passenger strand of the rxRNAori contains modifications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. In some embodiments, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 or 14 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is at least 6 or at least 7 nucleotides long.

RNAi constructs associated with the invention can have a thermodynamic stability ($\Delta G$) of less than $-13$ kkal/mol. In some embodiments, the thermodynamic stability ($\Delta G$) is less than $-20$ kkal/mol. In some embodiments there is a loss of efficacy when ($\Delta G$) goes below $-21$ kkal/mol. In some embodiments a ($\Delta G$) value higher than $-13$ kkal/mol is compatible with aspects of the invention. Without wishing to be bound by any theory, in some embodiments a molecule with a relatively higher ($\Delta G$) value may become active at a relatively higher concentration, while a molecule with a relatively lower ($\Delta G$) value may become active at a relatively lower concentration. In some embodiments, the ($\Delta G$) value may be higher than $-9$ kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. Chemical modification patterns on both the guide and passenger strand can be well tolerated and a combination of chemical modifications can lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. In some embodiments, molecules that have a double stranded region of 8-15 nucleotides can be selected for use in RNAi. In some embodiments, molecules are selected based on their thermodynamic stability ($\Delta G$). In some embodiments, molecules will be selected that have a ($\Delta G$) of less than $-13$ kkal/mol. For example, the ($\Delta G$) value may be $-13, -14, -15, -16, -17, -18, -19, -21, -22$ or less than $-22$ kkal/mol. In other embodiments, the ($\Delta G$) value may be higher than $-13$ kkal/mol. For example, the ($\Delta G$) value may be $-12, -11, -10, -9, -8, -7$ or more than $-7$ kkal/mol. It should be appreciated that $\Delta G$ can be calculated using any method known in the art. In some embodiments $\Delta G$ is calculated using Mfold, available through the Mfold internet site (mfold.bioinfo.rpi.edu/cgi-bin/rna-form1.cgi). Methods for calculating $\Delta G$ are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832;

Wuchty, S., Fontana, W., Hofacker, I. L., and Schuster, P. (1999) Biopolymers 49:145-165.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the sd-rxRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

Certain combinations of modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the sd-rxRNA structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly O-methyl modified with the phosphorothioate content described previously. For these types of compounds the 5' phosphorylation is not necessary in some embodiments. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. Single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the over-expression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

In some embodiments, a pyrimidine may be modified at the 5 position. For example, the 5 position of a pyrimidine may be modified with an alkyl group, an alkynyl group, an alkenyl group, an acyl group, or substituted derivatives thereof. In other examples, the 5 position of a pyrimidine may be modified with a hydroxyl group or an alkoxyl group or substituted derivative thereof. Also, the $N^4$ position of a pyrimidine may be alkylated. In still further examples, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, the $N^7$ position and/or $N^2$ and/or $N^3$ position of a purine may be modified with an alkyl group or substituted derivative thereof. In further examples, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Pat. Nos. 5,591,843, 7,205, 297, 6,432,963, and 6,020,483; non-limiting examples of pyrimidines modified at the $N^4$ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the $N^6$ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include $N^4,N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype.

Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH=CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl (CH$_2$—CH$_2$—CH$_3$), glycol (—O—CH$_2$—CH$_2$—O—) phosphate (PO$_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2, 2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfmyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419, 966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

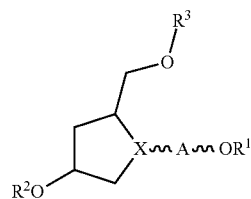

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

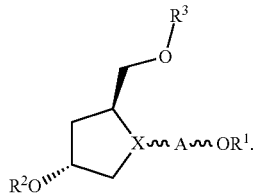

In certain embodiments, the molecule is of the formula:

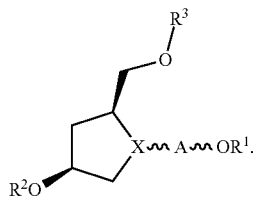

In certain embodiments, the molecule is of the formula:

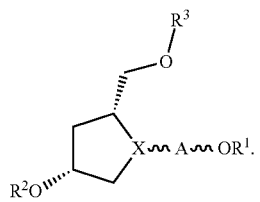

In certain embodiments, the molecule is of the formula:

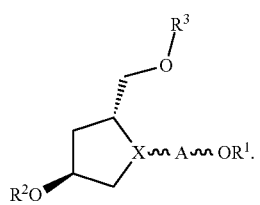

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

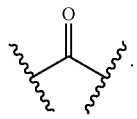 [SMILES: *C(*)=O]

In certain embodiments, A is of one of the formulae:

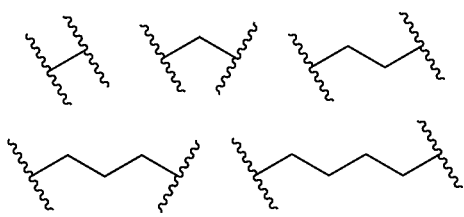

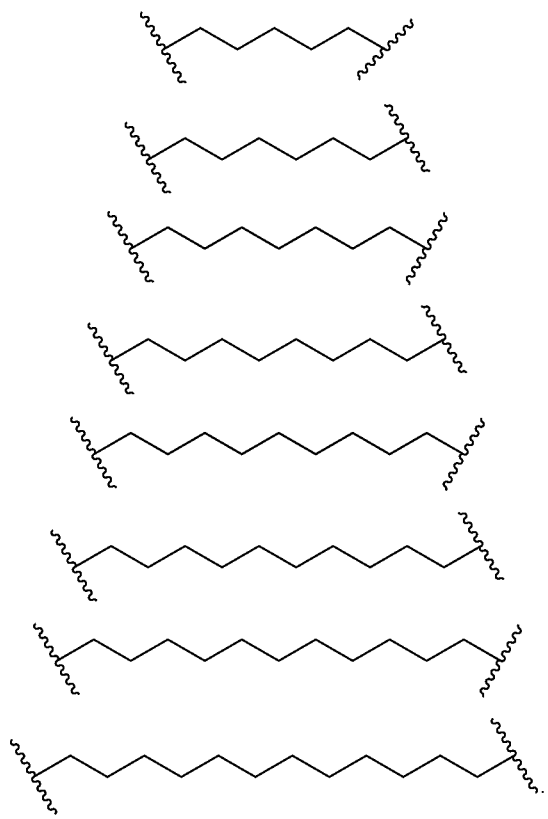

In certain embodiments, A is of one of the formulae:

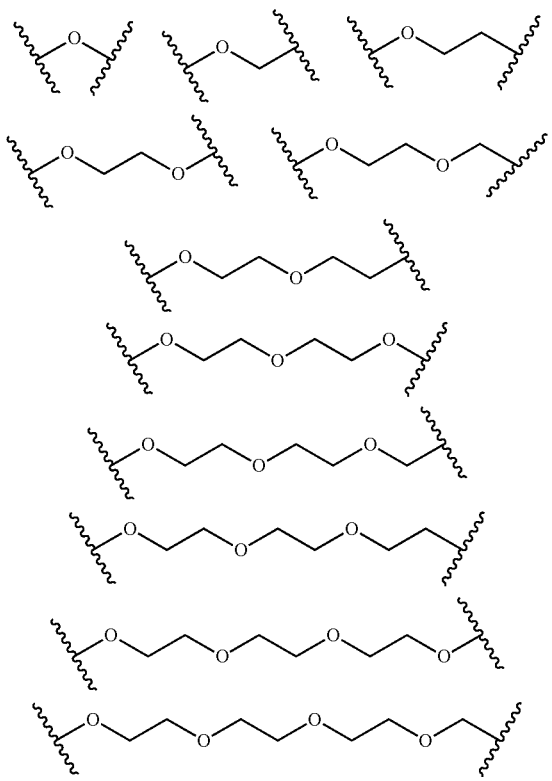

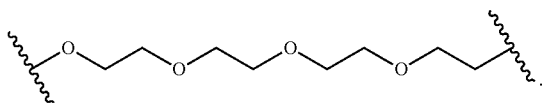

In certain embodiments, A is of one of the formulae:

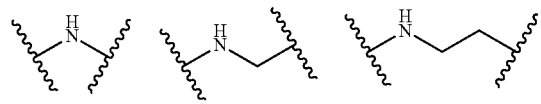

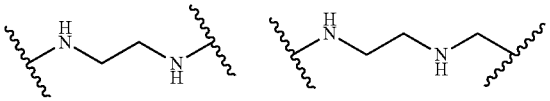

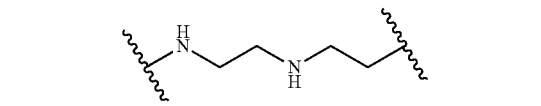

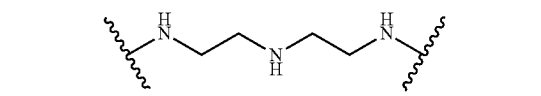

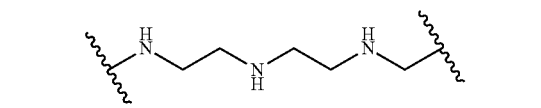

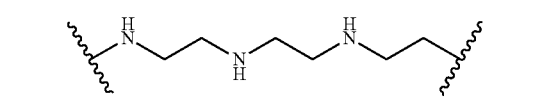

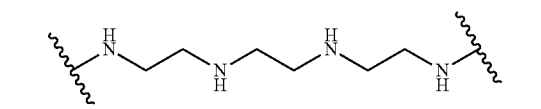

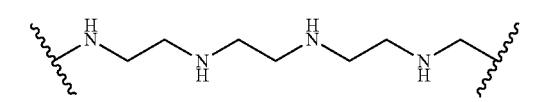

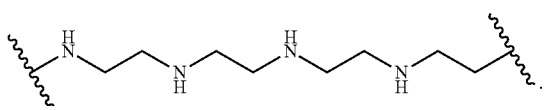

In certain embodiments, A is of the formula:

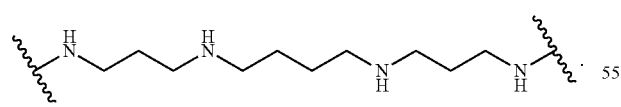

In certain embodiments, A is of the formula:

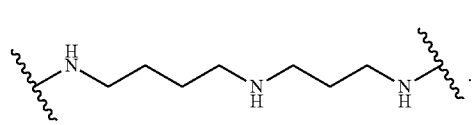 [SMILES: *NCCCCNCCCN*]

In certain embodiments, A is of the formula:

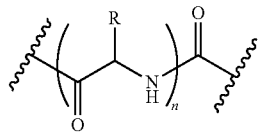

wherein each occurrence of R is independently the side chain of a natural or unnatural amino acid; and n is an integer between 1 and 20, inclusive. In certain embodiments, A is of the formula:

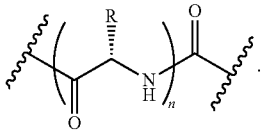

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

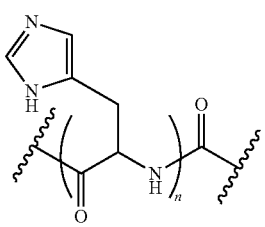

wherein n is an integer between 1 and 20, inclusive. In certain embodiments, A is of the formula:

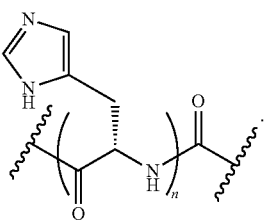

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

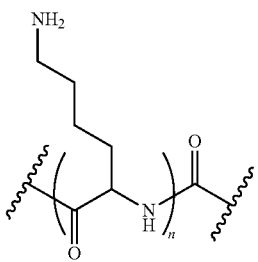

wherein n is an integer between 1 and 20, inclusive. In certain embodiments, A is of the formula:

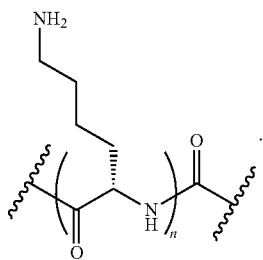

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

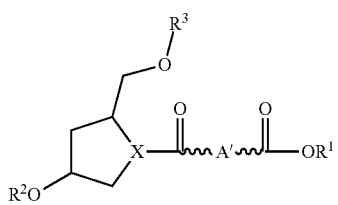

wherein X, $R^1$, $R^2$, and $R^3$ are as defined herein; and

A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

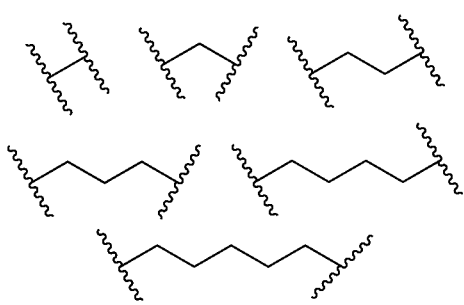

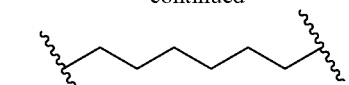
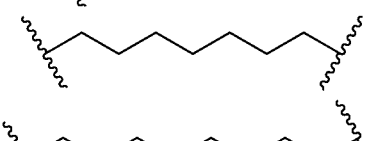
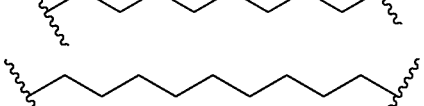
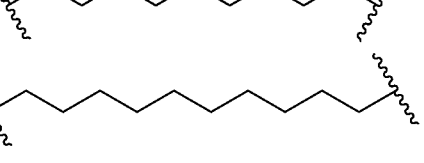
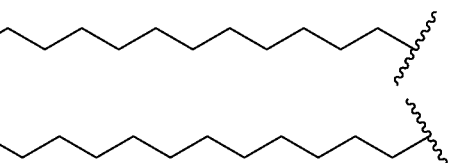

In certain embodiments, A is of one of the formulae:

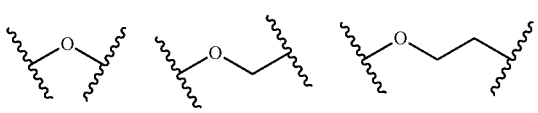
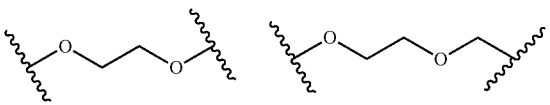
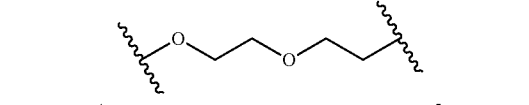
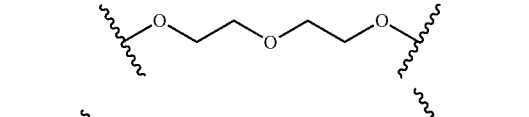
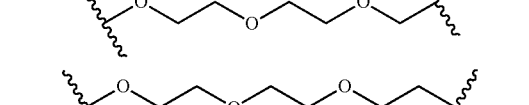
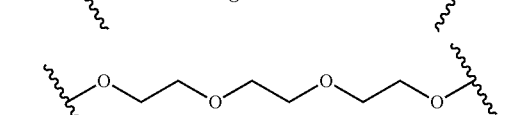
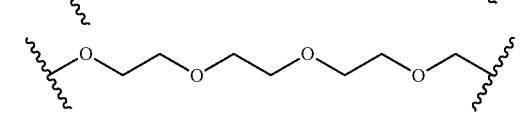
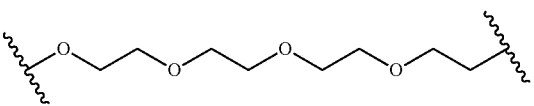

In certain embodiments, A is of one of the formulae:

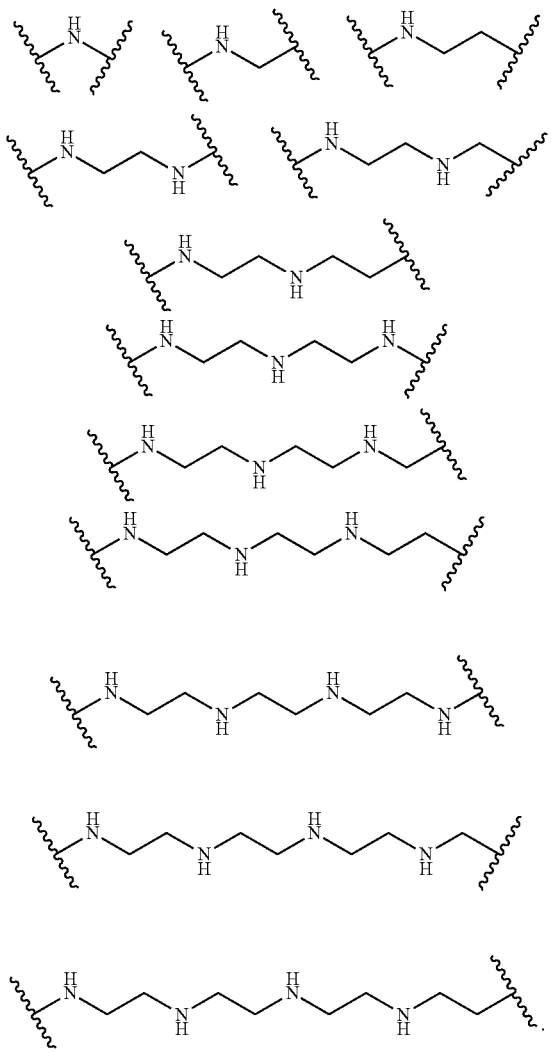

In certain embodiments, A is of the formula:

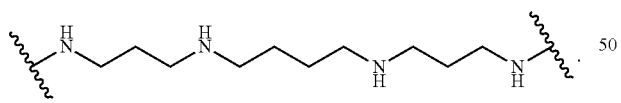

In certain embodiments, A is of the formula:

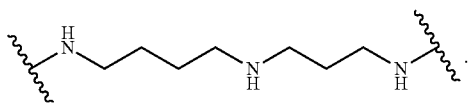 [SMILES: *NCCCCNCCCN*]

In certain embodiments, $R^1$ is a steroid. In certain embodiments, $R^1$ is a cholesterol. In certain embodiments, $R^1$ is a lipophilic vitamin. In certain embodiments, $R^1$ is a vitamin A. In certain embodiments, $R^1$ is a vitamin E.

In certain embodiments, $R^1$ is of the formula:

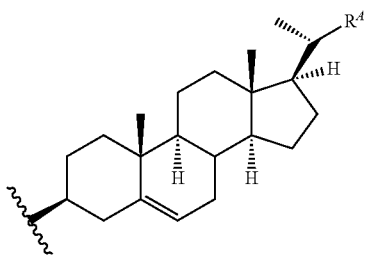

wherein $R^4$ is substituted or unsubstituted, cyclic or acyclic, branched or unbranched aliphatic; or substituted or unsubstituted, cyclic or acyclic, branched or unbranched heteroaliphatic.

In certain embodiments, $R^1$ is of the formula:

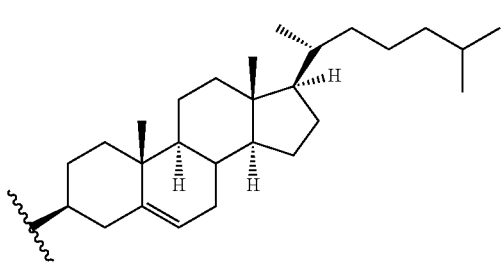

In certain embodiments, $R^1$ is of the formula:

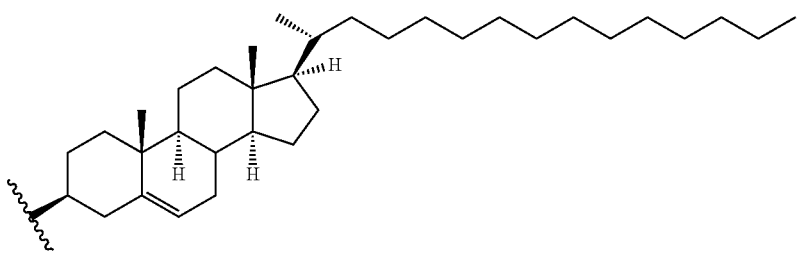

In certain embodiments, R¹ is of the formula:

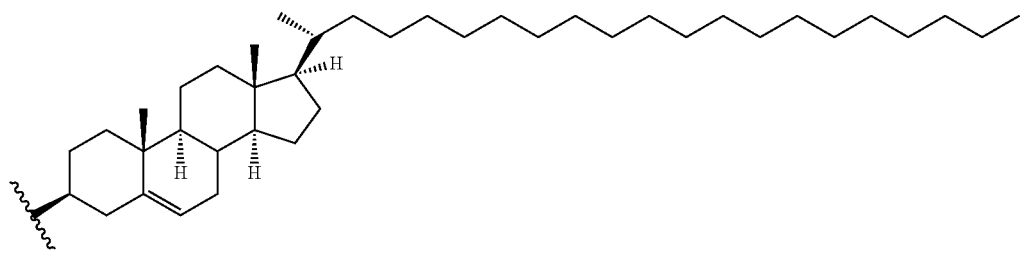

In certain embodiments, R¹ is of the formula:

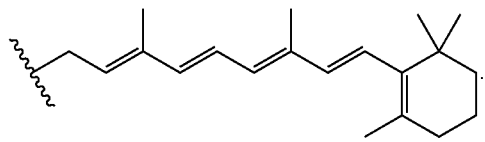 [SMILES: *C/C=C(C)/C=C/C=C(C)/C=C/C1=C(C)CCCC1(C)C]

In certain embodiments, R¹ is of the formula:

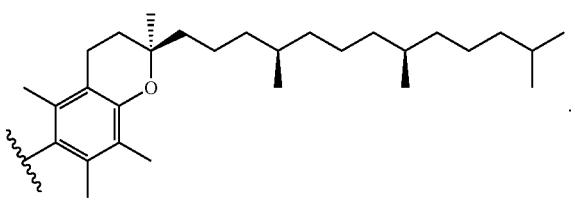 [SMILES: *c1c(C)c(C)c2c(c1C)CC[C@@](C)(CCC[C@H](C)CCC[C@H](C)CCCC(C)C)O2]

In certain embodiments, the nucleic acid molecule is of the formula:

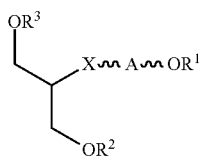

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

R¹ is a hydrophobic moiety;

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid.

In certain embodiments, the nucleic acid molecule is of the formula:

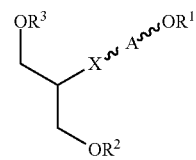

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

R¹ is a hydrophobic moiety;

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid.

In certain embodiments, the nucleic acid molecule is of the formula:

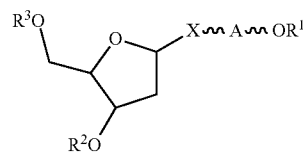

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

R¹ is a hydrophobic moiety;

R² is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and R³ is a nucleic acid. In certain embodiments, the nucleic acid molecule is of the formula:

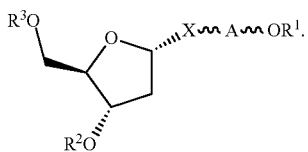

In certain embodiments, the nucleic acid molecule is of the formula:

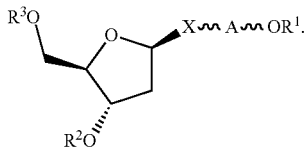

In certain embodiments, the nucleic acid molecule is of the formula:

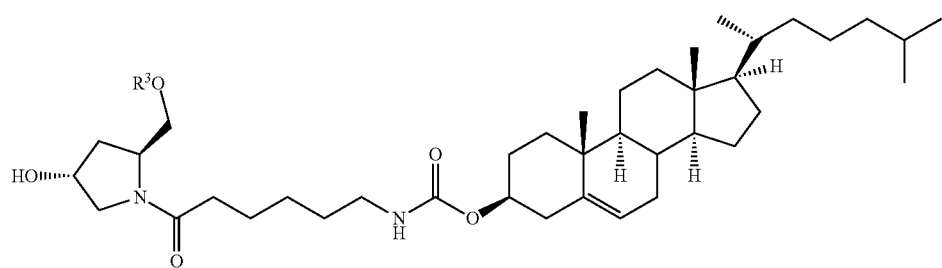

wherein $R^3$ is a nucleic acid.

In certain embodiments, the nucleic acid molecule is of the formula:

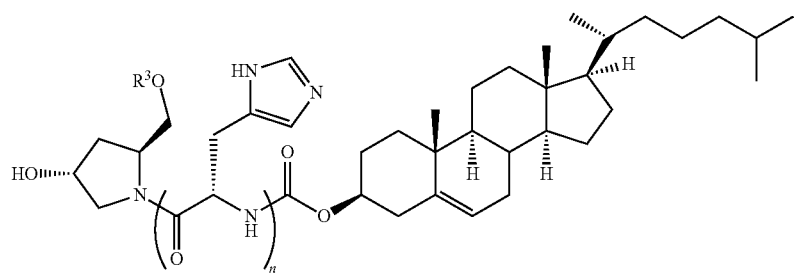

wherein $R^3$ is a nucleic acid; and
n is an integer between 1 and 20, inclusive.

In certain embodiments, the nucleic acid molecule is of the formula:

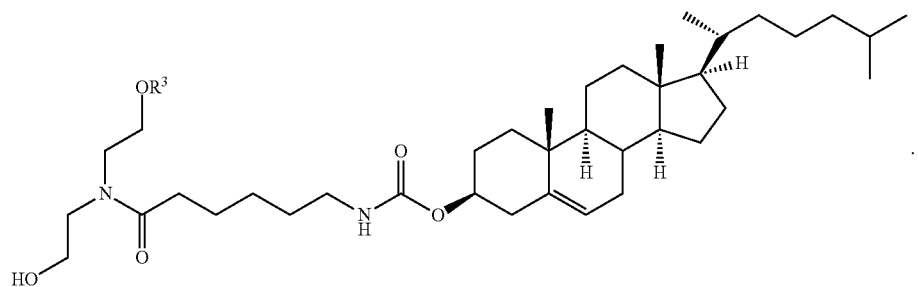

In certain embodiments, the nucleic acid molecule is of the formula:

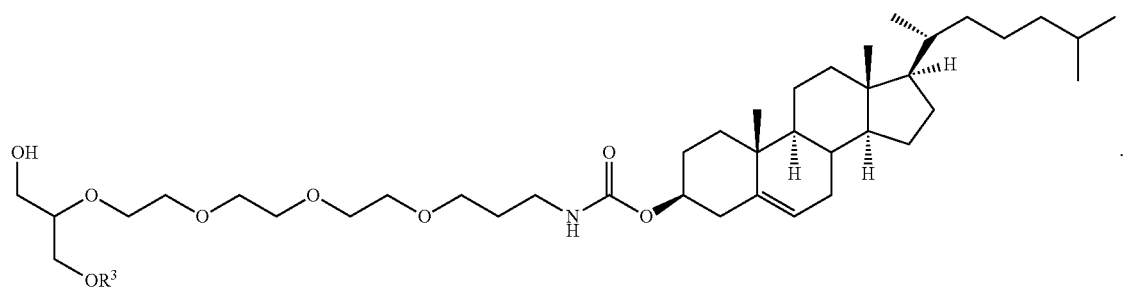

In certain embodiments, the nucleic acid molecule is of the formula:

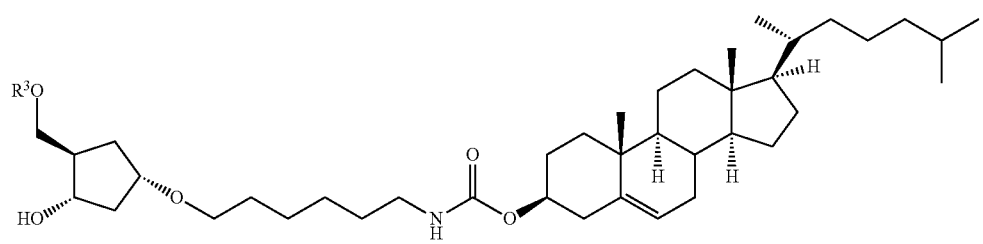

In certain embodiments, the nucleic acid molecule is of the formula:

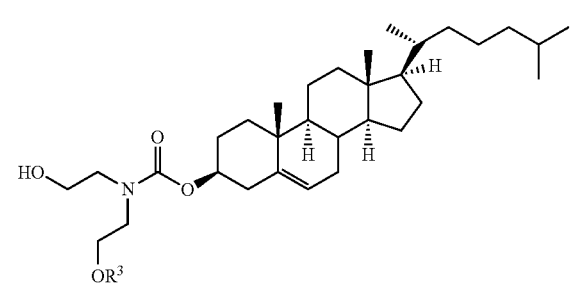

In certain embodiments, the nucleic acid molecule is of the formula:

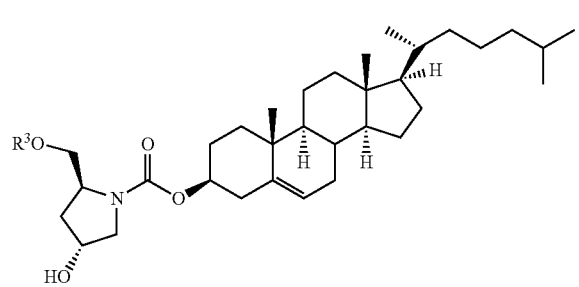

As used herein, the term "linkage" includes a naturally occurring, unmodified phosphodiester moiety (—O—$(PO^{2-})$—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise hydrophobically modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N) CH2CH(NH2)CO), Isobutyl, butyl, aminobenzyl; phenyl; and naphthyl.

Another type of conjugates that can be attached to the end (3' or 5' end), the loop region, or any other parts of the sd-rxRNA might include a sterol, sterol type molecule, peptide, small molecule, protein, etc. In some embodiments, a sd-rxRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC. In some embodiments, high levels of phosphorothioate modification can lead to improved delivery. In some embodiments, the guide and/or passenger strand is completely phosphorothioated.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. The chemical modification patterns may include combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. J. Am. Chem. Soc. 106:6077; Stec et al. 1985. J. Org. Chem. 50:3908; Stec et al. J. Chromatog. 1985. 326:263; LaPlanche et al. 1986. Nucl. Acid. Res. 1986. 14:9081; Fasman G. D., 1989. Practical Handbook of Biochemistry and Molecular Biology. 1989. CRC Press, Boca Raton, Fla.; Lamone. 1993. Biochem. Soc. Trans. 21:1; U.S. Pat. Nos. 5,013,830; 5,214,135; 5,525,719; Kawasaki et al. 1993. J. Med. Chem. 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

The invention is based, in part, on the surprising discovery that the double stranded nucleic acid molecules described herein are able to robustly and potently reduce levels of long non-coding RNAs (lncRNAs) in cells, both in the cytoplasm and nucleus. Without wishing to be bound by any particular theory, the inventors believe that the particular patterns of modifications on the passenger strand and guide strand of the double stranded nucleic acid molecules described herein (e.g., sd-rxRNAs) facilitate entry of the guide strand into the nucleus, where the guide strand mediates gene silencing (e.g., silencing of lncRNAs).

Without wishing to be bound by any theory, several potential mechanisms of action could account for this activity. For example, in some embodiments, the guide strand (e.g., antisense strand) of the nucleic acid molecule (e.g., sd-rxRNA) may dissociate from the passenger strand and enter into the nucleus as a single strand. Once in the nucleus the single stranded guide strand may associate with RNAse H or another ribonuclease and cleave the target (e.g., lncRNA) ("Antisense mechanism of action"). In some embodiments, the guide strand (e.g., antisense strand) of the nucleic acid molecule (e.g., sd-rxRNA) may associate with an Argonaute (Ago) protein in the cytoplasm or outside the nucleus, forming a loaded Ago complex. This loaded Ago complex may translocate into the nucleus and then cleave the target (e.g., lncRNA). In some embodiments, both strands (e.g. a duplex) of the nucleic acid molecule (e.g., sd-rxRNA) may enter the nucleus and the guide strand may associate with RNAse H, an Ago protein or another ribonuclease and cleaves the target (e.g., lncRNA).

The skilled artisan appreciates that the sense strand of the double stranded molecules described herein (e.g., sd-rxRNA sense strand) is not limited to delivery of a guide strand of the double stranded nucleic acid molecule described herein. Rather, in some embodiments, a passenger strand described herein is joined (e.g., covalently bound, non-covalently bound, conjugated, hybridized via a region of complementarity, etc.) to certain molecules (e.g., antisense oligonucleotides, ASO) for the purpose of targeting said other molecule to the nucleus of a cell. In some embodiments, the molecule joined to a sense strand described herein is a synthetic antisense oligonucleotide (ASO). In some embodiments, the sense strand joined to an anti-sense oligonucleotide is between 8-15 nucleotides long, chemically modified, and comprises a hydrophobic conjugate.

Without wishing to be bound by any particular theory, an ASO can be joined to a complementary passenger strand by hydrogen bonding. Accordingly, in some aspects, the disclosure provides a method of delivering a nucleic acid molecule to a cell, the method comprising administering an isolated nucleic acid molecule to a cell, wherein the isolated nucleic acid comprises a sense strand which is complementary to an anti-sense oligonucleotide (ASO), wherein the sense strand is between 8-15 nucleotides in length, comprises at least two phosphorothioate modifications, at least 50% of the pyrimidines in the sense strand are modified, and wherein the molecule comprises a hydrophobic conjugate.

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In some embodiments, the oligonucleotide compositions of the invention are contacted with bacterial cells. In some embodiments, the oligonucleotide compositions of the invention are contacted with eukaryotic cells (e.g., plant cell, mammalian cell, arthropod cell, such as insect cell). In some embodiments, the oligonucleotide compositions of the invention are contacted with stem cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. In some embodiments, Oligonucleotides are administered topically or through electroporation. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the sd-rxRNA of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1, and US 2010/0040656, and in PCT publications WO 2006/007372, and WO 2007/050643. The sd-rxRNA molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of ß-(1,3)-Glucan, ß-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with 1M NaOH/pH 4.0 H2O, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech*, Volume 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In the Examples section, the effectiveness of two glucan particle batches are tested: YGP SAF and YGP SAF+L (containing natural lipids). In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered are complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non-charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is built into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an amino linker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more than 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Thus, sterols useful in the invention, for example, include cholesterols, as well as unique sterols in which position 17 has attached side chain of 2-7 or longer than 9 carbons. In a particular embodiment, the length of the polycarbon tail is varied between 5 and 9 carbons. Such conjugates may have significantly better in vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non-charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. In some embodiments, vitamin A or E is used. Complexes are formed at different oligonucleotide concentrations, with higher concentrations favoring more efficient complex formation.

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more than 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues.

In another embodiment the fat emulsions of the cargo molecule contain more than 70% of Linoleic acid ($C_{18}H_{32}O_2$) and/or cardiolipin.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsons to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propan-aminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine-tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eukaryotic cells. Mannosylated glycoprotein conjugated to poly(L-lysine) in alveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Treatment Indications

In some aspects, the instant disclosure relates to the use of sd-rxRNA to target a lncRNA associated with disease. In some embodiments, the lncRNA associated with disease is associated with a neoplasm (e.g., cancer). Examples of cancers include lung, hepatocellular carcinoma, uterine endometrial stromal sarcoma, cervical cancer, breast cancer, osteosarcoma and colorectal cancer. In some embodiments, the lncRNA associated with disease is associated with alcoholism (see, for example, Eißmann et al. 2012). In some embodiments, the lncRNA associated with disease is associated with viral infections (see, for example, Eißmann et al. 2012). In some embodiments, the lncRNA associated with disease is associated with diabetes (see, for example, Liu et al. Cell Death and Disease 2014, 5).

In some instances, an sd-rxRNA is targeted to a neoplasm or a neoplastic tissue and is used to ameliorate at least one symptom of a condition or disorder associated with neoplasia. Neoplasia refers to the abnormal proliferation of cells, often resulting in an abnormal mass of tissue (i.e., a neoplasm). Neoplasm may be benign, pre-malignant (e.g., a carcinoma in situ), or malignant (cancerous). Benign neoplasms include uterine fibroids and melanocytic nevi (i.e., skin moles) that do not transform into cancer. Potentially malignant, or pre-cancerous, neoplasms include carcinoma in situ, which is an early form of carcinoma that does not invade surrounding tissue, but rather proliferate in their normal environment. Malignant neoplasms are commonly referred to as cancer, and they invade and destroy surrounding tissue, may form metastases, and eventually may be fatal to the host.

In some instances, the sd-rxRNA is targeted to a neoplasm or neoplastic cells of epithelial origin. Epithelial cells reside in one or more layers which cover the entire surface of the body and which line most of the hollow structures of the body, excluding the blood vessels, lymph vessels, and the heart interior, which are lined with endothelium, and the chest and abdominal cavities which are lined with mesothelium.

Epithelial neoplasms include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum.

In other instances, the sd-rxRNA is targeted to a neoplasm or neoplastic cells of mesenchymal origin, for example, neoplastic cells forming a sarcoma. Sarcomas are rare mesenchymal neoplasms that arise in bone and soft tissues. Different types of sarcomas are recognized, including liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extra skeletal [not bone] Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extra skeletal, and chondrosarcoma.

In yet other instances, the sd-rxRNA targets neoplasms or neoplastic cells of melanocytic origin. Melanomas are tumors arising from the melanocytic system of the skin and other organs. Examples of melanoma include lentigo maligna melanoma, superficial spreading melanoma, nodular melanoma, and acral lentiginous melanoma. In still other instances, the sd-rxRNA targets malignant neoplasms or neoplastic cells including, but not limited to, those found in biliary tract cancer, endometrial cancer, esophageal cancer, gastric cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

In other instances, the sd-rxRNA targets neoplasms or neoplastic cells originating in bone, muscle or connective tissue. The neoplastic cells may be found in primary tumors (e.g., sarcomas) of bone and connective tissue.

In some instances, the sd-rxRNA is delivered directly to a neoplasm, for example, by injection using a needle and syringe. Injection into the neoplasm permits large quantities of the sd-rxRNA to be delivered directly to the target cells while minimizing delivery to systemic sites. By direct injection into the neoplasm, an effective amount to promote RNA interference by the sd-rxRNA is distributed throughout at least a substantial volume of the neoplasm. In some instances, delivery of the sd-rxRNA requires a single injection into the neoplasm. In other instances, delivery of the sd-rxRNA requires multiple injections into separate regions of the neoplasm such that the entire mass of the neoplasm is invested with an effective amount to promote RNA interference by the sd-rxRNA. See U.S. Pat. Nos. 5,162,115 and 5,051,257, and Livraghi et al, *Tumori* 72 (1986), pp. 81-87, each of which is incorporated herein by reference.

The total dose, concentration, volume of the sd-rxRNA delivered, and rate of delivery can be optimized for a given neoplasm type, size and architecture. The zone of RNA interference can be controlled by optimizing these parameters. The volume and concentration of the sd-rxRNA delivered into the neoplasm must be sufficient to promote RNA interference throughout the tumor. Depending on the number of injections, and their placement with respect to neoplasm architecture, it can be useful to administer total sd-rxRNA volumes less than the neoplasm volume, greater than the neoplasm volume, or approximately equal to the neoplasm volume.

In some instances, the sd-rxRNA is delivered directly to the neoplasm using an implantable device.

In some instances sd-rxRNA injection into a neoplasm can be accompanied by ultrasound guidance.

In other instances, the sd-rxRNA is administered systemically, for example, intravenously, intraarterially, intramuscularly, or subcutaneously.

The sd-rxRNA that is targeted to a neoplasm, in some instances target a lncRNA that regulates or modulates a proliferative gene or a gene that is expressed at higher levels in a neoplastic tissue than in other tissues. In some embodiments, the sd-rxRNA is targeted to a lncRNA associated with a neoplasm. As used herein, a lncRNA "associated with a neoplasm" is a lncRNA that is dysregulated in a subject having a neoplasm (e.g., overexpressed or under expressed in the subject relative to the expression level in a subject not having a neoplasm).

lncRNAs have been shown to be involved in several different cancer types including: neuroblastoma, acute lymphocytic leukemia, melanoma, prostate cancer, hepatocellular carcinoma, colorectal cancer, breast cancer, ovarian cancer and non-small-cell lung cancer.

For example, the lncRNA MALAT1 is known to be dysregulated in several cancers, such as lung, hepatocellular carcinoma, uterine endometrial stromal sarcoma, cervical cancer, breast cancer, osteosarcoma and colorectal cancer (see, for example, Eiβmann et al. RNA Biology, 2012 Aug. 1; 9(8): 1076-1087).

MALAT1 has also been found to be upregulated in diabetes-induced microvascular dysfunction (Liu et al. 2014). In some embodiments, Malat1 is a target for anti-angiogenic therapy for diabetes-related microvascular complications such as diabetic retinopathy. MALAT1 has also been linked to viral infection and alcoholism. In some embodiments, MALAT1 is a target for treatment of viral infection or alcoholism.

In some aspects, the disorder to be treated according to methods described herein is selected from the group consisting of: cardiovascular diseases, including hypertension, stroke, hypertrophy and heart failure; neurological and psychiatric disorders, including Alzheimer's Disease, schizophrenia, schizoaffective disorder, dipolar disorder, major depression and autistic disorders; metabolic diseases; and diseases associated with immune dysfunction or inflammation.

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

In some embodiments, the disclosure relates to a composition (e.g., pharmaceutical composition) comprising an oligonucleotide (e.g., an isolated double stranded nucleic acid molecule). In some embodiments, the composition comprises an additional therapeutic agent. Non-limiting examples of additional therapeutic agents include but are not limited to nucleic acids (e.g., sd-rxRNA, etc.), small molecules (e.g., small molecules useful for treating cancer, neurodegenerative diseases, infectious diseases, autoimmune diseases, etc.), peptides (e.g., peptides useful for treating cancer, neurodegenerative diseases, infectious diseases, autoimmune diseases, etc.), and polypeptides (e.g., antibodies useful for treating cancer, neurodegenerative diseases, infectious diseases, autoimmune diseases, etc.). Compositions of the disclosure can have, in some embodiments, 2, 3, 4, 5, 6, 7, 8, 9, 10, or more additional therapeutic agents. In some embodiments, a composition comprises more than 10 additional therapeutic agents.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. In preferred embodiments, the sd-rxRNA molecules are administered by intradermal injection or subcutaneously.

With respect to in vivo applications, in some embodiments, the formulations of the present invention can be administered to a patient in a variety of forms adapted to deliver the construct to the eye. In some embodiments, parenteral administration is ocular. Ocular administration can be intravitreal, intracameral, subretinal, subconjunctival, or subtenon.

The sd-rxRNA molecules, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

For administration by inhalation, such as by insufflation, the sd-rxRNA molecules for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the sd-rxRNA molecules. The sd-rxRNA molecule is delivered to the lungs of a mammal while inhaling and traverses across the lung epithelial lining to the blood stream. Other reports of inhaled molecules include Adjei et al., 1990, Pharmaceutical Research, 7:565 569; Adjei et al., 1990, International Journal of Pharmaceutics, 63:135 144 (leuprolide acetate); Braquet et al., 1989, Journal of Cardiovascular Pharmacology, 13(suppl. 5):143 146 (endothelin-1); Hubbard et al., 1989, Annals of Internal Medicine, Vol. III, pp. 206 212 (al antitrypsin); Smith et al., 1989, J. Clin. Invest. 84:1145-1146 (a 1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482 3488 (interferon g and tumor necrosis factor alpha) and Platz et al., U.S. Pat. No. 5,284,656 (granulocyte colony stimulating factor). A method and composition for pulmonary delivery of drugs for systemic effect is described in, and incorporated by reference from, U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide (or derivative) dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered dose inhaler device will generally comprise a finely divided powder, such as a dry powder formulation, containing the sd-rxRNA molecule suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2 tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide (or derivative) and may also include a bulking agent, such as lactose, sorbitol, sucrose, or mannitol in amounts which facilitate dispersal of the powder from the device, e.g., 50 to 90% by weight of the formulation. The sd-rxRNA molecule can be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. In some embodiments, preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 μm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Ocular administration of sd-rxRNAs, including intravitreal, intracameral, subretinal, subconjunctival, and subtenon administration, can be optimized through testing of dosing regimens. In some embodiments, a single administration is sufficient. To further prolong the effect of the administered sd-rxRNA, the sd-rxRNA can be administered in a slow-release formulation or device, as would be familiar to one of ordinary skill in the art. The hydrophobic nature of sd-rxRNA compounds can enable use of a wide variety of polymers, some of which are not compatible with conventional oligonucleotide delivery.

Intravenous administration of sd-rxRNAs can be optimized through testing of dosing regimens. In some instances, intravenous administration is achieved through infusion, for example through the use of an infusion pump to infuse molecules into the circulatory system of a subject. The infusion can be continuous or intermittent. In some instances, it is preferred if the dosing regimen involves repetitive administration of a short-term continuous infusion. For example, the continuous infusion can last for approximately 5 min, 10 min, 20 min, 30 min, 40 min, 50 min, 1.0 hour, 1.1 hours, 1.2 hours, 1.3 hours, 1.4 hours, 1.5 hours, 1.6 hours, 1.7 hours, 1.8 hours, 1.9 hours, 2.0 hours, 2.1 hours, 2.2 hours, 2.3 hours, 2.4 hours, 2.5 hours, 2.6 hours, 2.7 hours, 2.8 hours, 2.9 hours, 3.0 hours, 3.1 hours, 3.2 hours, 3.3 hours, 3.4 hours. 3.5 hours, 3.6 hours, 3.7 hours, 3.8 hours, 3.9 hours, 4.0 hours, 4.1 hours, 4.2 hours, 4.3 hours, 4.4 hours, 4.5 hours, 4.6 hours, 4.7 hours, 4.8 hours, 4.9 hours, 5.0 hours, 5.1 hours, 5.2 hours, 5.3 hours, 5.4 hours, 5.5 hours, 5.6 hours, 5.7 hours, 5.8 hours, 5.9 hours, 6.0 hours, or more than 6.0 hours, including any intermediate values.

The infusion can be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Administration of sd-rxRNAs, such as through intradermal injection or subcutaneous delivery, can be optimized through testing of dosing regimens. In some embodiments, a single administration is sufficient. To further prolong the effect of the administered sd-rxRNA, the sd-rxRNA can be administered in a slow-release formulation or device, as would be familiar to one of ordinary skill in the art. The hydrophobic nature of sd-rxRNA compounds can enable use of a wide variety of polymers, some of which are not compatible with conventional oligonucleotide delivery.

In other embodiments, the sd-rxRNA is administered multiple times. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Aspects of the invention relate to administering sd-rxRNA molecules to a subject. In some instances the subject is a patient and administering the sd-rxRNA molecule involves administering the sd-rxRNA molecule in a doctor's office. Without wishing to be bound by any theory, a continuous infusion may saturate the normal clearance mechanism and maintain relatively high compound levels in the blood to ensure tissue distribution. sd-rxRNA are well suited to such an approach due to their low levels of toxicity.

In some instances, the effective amount of sd-rxRNA that is delivered through ocular administration is at least approximately 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 µg including any intermediate values.

sd-rxRNA molecules administered through methods described herein are effectively targeted to all the cell types in the eye.

In some embodiments, more than one sd-rxRNA molecule is administered simultaneously. For example a composition may be administered that contains 1, 2, 3, 4, 5, 6, 7, 8, 9, 10 or more than 10 different sd-rxRNA molecules. In certain embodiments, a composition comprises 2 or 3 different sd-rxRNA molecules. When a composition comprises more than one sd-rxRNA, the sd-rxRNA molecules within the composition can be directed to the same gene or to different genes.

In some instances, the effective amount of sd-rxRNA that is delivered by subcutaneous administration is at least approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

Subcutaneous administration can also be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

In some instances, sd-rxRNA is administered through insufflation. In some instances, the effective amount of sd-rxRNA that is delivered by insufflation is at least approximately 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

Administration by insufflation can also be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

sd-rxRNA molecules administered by methods described herein including intravenous, subcutaneous and insufflation, can be targeted to a variety of remote tissues in the body including liver, heart, lung, kidney, spleen and skin.

In some instances, the effective amount of sd-rxRNA that is delivered through intradermal injection is at least approximately 1, 5, 10, 15, 20, 25, 30, 35, 40, 45, 50, 55, 60, 65, 70, 75, 80, 85, 90, 95, 100, 125, 150, 200, 250, 300, 350, 400, 450, 500, 550, 600, 650, 700, 750, 800, 850, 900, 950 or more than 950 µg including any intermediate values.

sd-rxRNA molecules administered through methods described herein are effectively targeted to all the cell types in the skin.

Various modalities of introducing nucleic acids into a subject (e.g., a cell of a subject) are contemplated by the disclosure. For example, nucleic acids (e.g., a solution containing the nucleic acids) can be injected into a subject (e.g., injected into a cell) or a subject (e.g., a cell) can be bombarded by particles covered by the nucleic acids. In some embodiments, the cell or organism is soaked in a solution of the nucleic acid. In some embodiments, a nucleic acid is introduced into an organism or cell by electroporation of cell membranes in the presence of the nucleic acid. In some embodiments, a viral construct comprising the nucleic acid is packaged into a viral particle and accomplishes introduction of the nucleic acid into the cell and transcription of nucleic acid. Further examples of modalities for introducing nucleic acids into a subject (e.g., a cell of a subject) include but are not limited to lipid-mediated carrier transport, chemical-mediated transport (e.g., calcium phosphate), etc.

Nucleic acids can be introduced with additional components. For example, in some embodiments, the nucleic acid is introduced with a component that enhances nucleic acid uptake by the cell. In some embodiments, the nucleic acid is introduced with a component that inhibits annealing of single strands. In some embodiments, the nucleic acid is introduced with a component that stabilizes the nucleic acid molecule, or other-wise increases inhibition of the target gene.

Nucleic acid may be directly introduced into the cell (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

In some embodiments, the cell with the target gene may be derived from any organism. In some embodiments, the cell with the target gene may be contained in (e.g., housed by, or present within) any organism. For example, the organism may a plant, animal, protozoan, bacterium, arthropod, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

A further preferred use for the agents of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable priming agent/RNAi agent which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Therapeutic Use

By inhibiting the expression of a gene (e.g., a lncRNA), the oligonucleotide compositions of the present invention can be used to treat any disease involving the expression of a lncRNA. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for preventing in a subject, a disease or condition associated with an aberrant or unwanted target gene expression or activity, by administering to the subject a therapeutic agent (e.g., a RNAi agent or vector or transgene encoding same). If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the modulatory method of the invention involves contacting a cell capable of expressing target gene with a therapeutic agent of the invention that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. Typically, subjects are first treated with a priming agent so as to be more responsive to the subsequent RNAi therapy. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The therapeutic agents of the invention can be administered to individuals to treat (prophylactically or therapeutically) disorders associated with aberrant or unwanted target gene (e.g., lncRNA) activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10-11): 983-985 and Linder, M. W. et al. (1997) Clin. Chem. 43(2):254-266

RNAi in Skin Indications

Nucleic acid molecules, or compositions comprising nucleic acid molecules, described herein may in some embodiments be administered to pre-treat, treat or prevent compromised skin. As used herein "compromised skin" refers to skin which exhibits characteristics distinct from normal skin. Compromised skin may occur in association with a dermatological condition. Several non-limiting examples of dermatological conditions include rosacea, common acne, seborrheic dermatitis, perioral dermatitis, acneform rashes, transient acantholytic dermatosis, and acne necrotica miliaris. In some instances, compromised skin may comprise a wound and/or scar tissue. In some instances, methods and compositions associated with the invention may be used to promote wound healing, prevention, reduction or inhibition of scarring, and/or promotion of re-epithelialisation of wounds.

A subject can be pre-treated or treated prophylactically with a molecule associated with the invention, prior to the skin of the subject becoming compromised. As used herein "pre-treatment" or "prophylactic treatment" refers to administering a nucleic acid to the skin prior to the skin becoming compromised. For example, a subject could be pre-treated 15 minutes, 30 minutes, 1 hour, 2 hours, 3 hours, 4 hours, 5 hours, 6 hours, 7 hours, 8 hours, 9 hours, 10 hours, 11 hours, 12 hours, 24 hours, 48 hours, 3 days, 4 days, 5 days, 6 days, 7 days, 8 days or more than 8 days prior to the skin becoming compromised. In other embodiments, a subject can be treated with a molecule associated with the invention immediately before the skin becomes compromised and/or simultaneous to the skin becoming compromised and/or after the skin has been compromised. In some embodiments, the skin is compromised through a medical procedure such as surgery, including elective surgery. In certain embodiments methods and compositions may be applied to areas of the skin that are believed to be at risk of becoming compromised. It should be appreciated that one of ordinary skill in the art would be able to optimize timing of administration using no more than routine experimentation.

In some aspects, methods associated with the invention can be applied to promote healing of compromised skin. Administration can occur at any time up until the compromised skin has healed, even if the compromised skin has already partially healed. The timing of administration can depend on several factors including the nature of the compromised skin, the degree of damage within the compromised skin, and the size of the compromised area. In some embodiments administration may occur immediately after the skin is compromised, or 30 minutes, 1 hour, 2 hours, 4 hours, 6 hours, 8 hours, 12 hours, 24 hours, 48 hours, or more than 48 hours after the skin has been compromised. Methods and compositions of the invention may be administered one or more times as necessary. For example, in some embodiments, compositions may be administered daily or twice daily. In some instances, compositions may be administered both before and after formation of compromised skin.

Compositions associated with the invention may be administered by any suitable route. In some embodiments, administration occurs locally at an area of compromised skin. For example, compositions may be administered by intradermal injection. Compositions for intradermal injection may include injectable solutions. Intradermal injection may in some embodiments occur around the area of compromised skin or at a site where the skin is likely to become compromised. In some embodiments, compositions may also be administered in a topical form, such as in a cream or ointment. In some embodiments, administration of compositions described herein comprises part of an initial treatment or pre-treatment of compromised skin, while in other embodiments, administration of such compositions comprises follow-up care for an area of compromised skin.

The appropriate amount of a composition or medicament to be applied can depend on many different factors and can be determined by one of ordinary skill in the art through routine experimentation. Several non-limiting factors that might be considered include biological activity and bioavailability of the agent, nature of the agent, mode of administration, half-life, and characteristics of the subject to be treated.

In some aspects, nucleic acid molecules associated with the invention may also be used in treatment and/or prevention of fibrotic disorders, including pulmonary fibrosis, liver cirrhosis, scleroderma and glomerulonephritis, lung fibrosis, liver fibrosis, skin fibrosis, muscle fibrosis, radiation fibrosis, kidney fibrosis, proliferative vitreoretinopathy and uterine fibrosis.

A therapeutically effective amount of a nucleic acid molecule described herein may in some embodiments be an amount sufficient to prevent the formation of compromised skin and/or improve the condition of compromised skin. In some embodiments, improvement of the condition of compromised skin may correspond to promotion of wound healing and/or inhibition of scarring and/or promotion of epithelial regeneration. The extent of prevention of formation of compromised skin and/or improvement to the condition of compromised skin may in some instances be determined by, for example, a doctor or clinician.

The ability of nucleic acid molecules associated with the invention to prevent the formation of compromised skin and/or improve the condition of compromised skin may in some instances be measured with reference to properties exhibited by the skin. In some instances, these properties may include rate of epithelialisation and/or decreased size of an area of compromised skin compared to control skin at comparable time points.

As used herein, prevention of formation of compromised skin, for example prior to a surgical procedure, and/or improvement of the condition of compromised skin, for example after a surgical procedure, can encompass any increase in the rate of healing in the compromised skin as compared with the rate of healing occurring in a control sample. In some instances, the condition of compromised skin may be assessed with respect to either comparison of the rate of re-epithelialisation achieved in treated and control skin, or comparison of the relative areas of treated and control areas of compromised skin at comparable time points. In some aspects, a molecule that prevents formation of compromised skin or promotes healing of compromised skin may be a molecule that, upon administration, causes the area of compromised skin to exhibit an increased rate of re-epithelialisation and/or a reduction of the size of compromised skin compared to a control at comparable time points. In some embodiments, the healing of compromised skin may give rise to a rate of healing that is 5%, 10%, 20%, 30%, 40%, 50%, 60%, 70%, 80%, 90% or 100% greater than the rate occurring in controls.

In some aspects, subjects to be treated by methods and compositions associated with the invention may be subjects who will undergo, are undergoing or have undergone a medical procedure such as a surgery. In some embodiments, the subject may be prone to defective, delayed or otherwise impaired re-epithelialisation, such as dermal wounds in the aged. Other non-limiting examples of conditions or disorders in which wound healing is associated with delayed or otherwise impaired re-epithelialisation include patients suffering from diabetes, patients with polypharmacy, postmenopausal women, patients susceptible to pressure injuries, patients with venous disease, clinically obese patients, patients receiving chemotherapy, patients receiving radiotherapy, patients receiving steroid treatment, and immunocompromised patients. In some instances, defective re-epithelialisation response can contributes to infections at the wound site, and to the formation of chronic wounds such as ulcers.

In some embodiments, methods associated with the invention may promote the re-epithelialisation of compromised skin in chronic wounds, such as ulcers, and may also inhibit scarring associated with wound healing. In other embodiments, methods associated with the invention are applied to prevention or treatment of compromised skin in acute wounds in patients predisposed to impaired wound healing developing into chronic wounds. In other aspects, methods associated with the invention are applied to promote accelerated healing of compromised skin while preventing, reducing or inhibiting scarring for use in general clinical contexts. In some aspects, this can involve the treatment of surgical incisions and application of such methods may result in the prevention, reduction or inhibition of scarring that may otherwise occur on such healing. Such treatment may result in the scars being less noticeable and exhibiting regeneration of a more normal skin structure. In other embodiments, the compromised skin that is treated is not compromised skin that is caused by a surgical incision. The compromised skin may be subject to continued care and continued application of medicaments to encourage re-epithelialisation and healing.

In some aspects, methods associated with the invention may also be used in the treatment of compromised skin associated with grafting procedures. This can involve treatment at a graft donor site and/or at a graft recipient site. Grafts can in some embodiments involve skin, artificial skin, or skin substitutes. Methods associated with the invention can also be used for promoting epithelial regeneration. As used herein, promotion of epithelial regeneration encompasses any increase in the rate of epithelial regeneration as compared to the regeneration occurring in a control-treated or untreated epithelium. The rate of epithelial regeneration attained can in some instances be compared with that taking place in control-treated or untreated epithelia using any suitable model of epithelial regeneration known in the art. Promotion of epithelial regeneration may be of use to induce effective re-epithelialisation in contexts in which the re-epithelialisation response is impaired, inhibited, retarded or otherwise defective. Promotion of epithelial regeneration may be also effected to accelerate the rate of defective or normal epithelial regeneration responses in patients suffering from epithelial damage.

Some instances where re-epithelialisation response may be defective include conditions such as pemphigus, Hailey-Hailey disease (familial benign pemphigus), toxic epidermal necrolysis (TEN)/Lyell's syndrome, epidermolysis bullosa, cutaneous leishmaniasis and actinic keratosis. Defective re-epithelialisation of the lungs may be associated with idiopathic pulmonary fibrosis (IPF) or interstitial lung disease. Defective re-epithelialisation of the eye may be associated with conditions such as partial limbal stem cell deficiency or corneal erosions. Defective re-epithelialisation of the gastrointestinal tract or colon may be associated with conditions such as chronic anal fissures (fissure in ano), ulcerative colitis or Crohn's disease, and other inflammatory bowel disorders.

In some aspects, methods associated with the invention are used to prevent, reduce or otherwise inhibit compromised skin associated with scarring. This can be applied to any site within the body and any tissue or organ, including the skin, eye, nerves, tendons, ligaments, muscle, and oral cavity (including the lips and palate), as well as internal organs (such as the liver, heart, brain, abdominal cavity, pelvic cavity, thoracic cavity, guts and reproductive tissue). In the skin, treatment may change the morphology and organization of collagen fibers and may result in making the scars less visible and blend in with the surrounding skin. As used herein, prevention, reduction or inhibition of scarring encompasses any degree of prevention, reduction or inhibition in scarring as compared to the level of scarring occurring in a control-treated or untreated wound.

Prevention, reduction or inhibition of compromised skin, such as compromised skin associated with dermal scarring, can be assessed and/or measured with reference to microscopic and/or macroscopic characteristics. Macroscopic characteristics may include color, height, surface texture and stiffness of the skin. In some instances, prevention, reduction or inhibition of compromised skin may be demonstrated when the color, height, surface texture and stiffness of the skin resembles that of normal skin more closely after treatment than does a control that is untreated. Microscopic assessment of compromised skin may involve examining characteristics such as thickness and/or orientation and/or composition of the extracellular matrix (ECM) fibers, and cellularity of the compromised skin. In some instances, prevention, reduction or inhibition of compromised skin may be demonstrated when the thickness and/or orientation and/or composition of the extracellular matrix (ECM) fibers, and/or cellularity of the compromised skin resembles that of normal skin more closely after treatment than does a control that is untreated.

In some aspects, methods associated with the invention are used for cosmetic purposes, at least in part to contribute to improving the cosmetic appearance of compromised skin. In some embodiments, methods associated with the invention may be used to prevent, reduce or inhibit compromised skin such as scarring of wounds covering joints of the body. In other embodiments, methods associated with the invention may be used to promote accelerated wound healing and/or prevent, reduce or inhibit scarring of wounds at increased risk of forming a contractile scar, and/or of wounds located at sites of high skin tension.

In some embodiments, methods associated with the invention can be applied to promoting healing of compromised skin in instances where there is an increased risk of pathological scar formation, such as hypertrophic scars and keloids, which may have more pronounced deleterious effects than normal scarring. In some embodiments, methods described herein for promoting accelerated healing of compromised skin and/or preventing, reducing or inhibiting scarring are applied to compromised skin produced by surgical revision of pathological scars.

Aspects of the invention can be applied to compromised skin caused by burn injuries. Healing in response to burn injuries can lead to adverse scarring, including the formation of hypertrophic scars. Methods associated with the invention can be applied to treatment of all injuries involving damage to an epithelial layer, such as injuries to the skin in which the epidermis is damaged. Other non-limiting examples of injuries to epithelial tissue include injuries involving the respiratory epithelia, digestive epithelia or epithelia surrounding internal tissues or organs.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Identification of Potent Sd-rxRNAs Targeting lncRNA ENST00000602414 sd-rxRNAs targeting lncRNA ENST00000602414 were designed, synthesized and screened in vitro to determine the ability of the sd-rxRNAs to reduce target lncRNA levels. The sd-rxRNAs were tested for activity in a human hepatocellular carcinoma cell line (40,000 cells/well, 96 well plate). The cells were treated with a panel of ENST00000602414 lncRNA-targeting sd-rxRNAs or non-targeting control (#26247) in media containing 10% FCS. The concentration of sd-rxRNA tested was 5 µM. The non-targeting control sd-rxRNA (#26247) is of similar structure to the lncRNA-targeting sd-rxRNAs and contains similar stabilizing modifications throughout both strands. Forty eight hours post-administration, cells were lysed and lncRNA levels determined with lncRNA-specific SYBR Green I qPCR assays and SsoAdvanced Universal SYBR Green Supermix (Bio-Rad) according to the manufacturer's protocol. FIG. 1 demonstrates the lncRNA-targeting sd-rxRNAs, comprising sense strands and antisense strands found in Tables 1 and 2, respectively, significantly reduce target gene lncRNA levels in vitro in a human hepatocarcinoma cell line. All sense sequences in Table 1 have the following modification: TEG-Chl, wherein Chl stands for cholesterol and TEG is a linker. Data were normalized, using geometric average to a panel of 4 house-keeping genes and graphed with respect to the mock (non-transfected) control. Samples were run in biological duplicates.

The human lncRNA sequence is represented by Ensembl transcript ID: ENST00000602414 (SEQ ID NO: 1), as shown below.

```
GGAATAGCGTCATCAGTTCTATAAGAGAGCGTGTGCCGAAGGCCTCGGCC
TTTCACATTCGGGAAGCGTCGGGATTAGGTGAAAGTACGTAGTTGTCTTT
CGTAAGTTAAAATGATAATTGGGCCGAAACTTACTGCCTTACCTAAAAGG
```

```
CAGCGCAGTCAGGATATTGGTAGGTCGGGGGCGGCTTTGGAAACCCTTAA

GTTTACAAGCATGCGCGGACTTGAGTGCTCATTAGGTCGCCGGGCGTCCA

CGTGCAGCCCTGGACCCTGAACCCCGGCGTGCGTGGGCCGTGGGCCCTCG

GGGAAAGGTTCCGTGCACTCGGGGACTCCGGTGAAGCCTGTTCAGCCGTC

TGTGTCATGTGGCCATCTTGAGTCTACTCTGTCGCTCTTGTGCCCTAGCA

CCCCGAGAACCGTCAGTTTGAGCCAGATGGAAGCTGAGCTGAACACATTA

CGATGGATGATGGAAACATAAGACTATCAAGAAATCCAAGTGGTAATGGG

CGAAGTTTATTCAGCATCCGGCAATGGACTTATCGTAGTTGGGGAAACGG

GTGTTCCGAATAATATCCTGGAAGTTATCAGGACACCTATTTTAAATATA

GGCCTGAATTTTGTAAAGTAATATTTAAGGTGGTCCGTGATAATTAAATA

AAATGCTTAATTCATGTGGCTA
```

Figure 2:
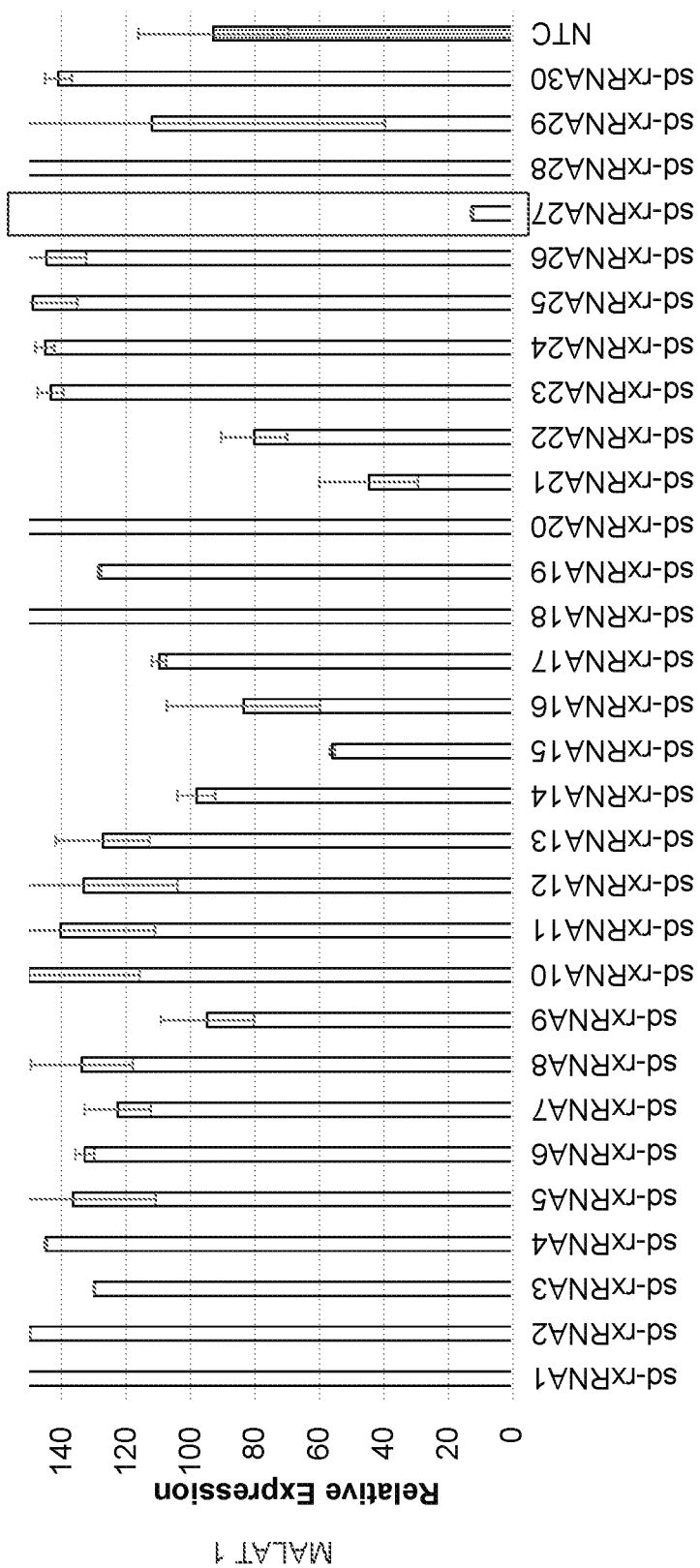
FIG. 2 shows the identification of potent sd-rxRNAs targeting MALAT1 in a human colorectal carcinoma cell line. The MALAT1-targeting sd-rxRNAs described in this particular assay significantly reduced target gene lncRNA levels in vitro in a human hepatocarcinoma cell line.

Example 2: Identification of Potent Sd-rxRNAs Targeting lncRNA MALAT1 sd-rxRNAs targeting lncRNA MALAT1 were designed, synthesized and screened in vitro to determine the ability of the sd-rxRNAs to reduce target lncRNA levels. The sd-rxRNAs were tested for activity in a human hepatocellular carcinoma cell line (40,000 cells/well, 96 well plate) and a human colorectal carcinoma cell line (40,000 cells/well). Cells were treated with a panel of MALAT1-targeting sd-rxRNAs or non-targeting control (#26247) in media containing 10% FCS. The concentration of sd-rxRNA tested was 5 µM. The non-targeting control sd-rxRNA (#26247) is of similar structure to the MALAT1-targeting sd-rxRNAs and contains similar stabilizing modifications throughout both strands. Forty eight hours post-administration, cells were lysed and MALAT1 levels determined with MALAT1-specific SYBR Green I qPCR assays and SsoAdvanced Universal SYBR Green Supermix (Bio-Rad) according to manufacturer's protocols. FIG. 2 demonstrates the MALAT1-targeting sd-rxRNAs, comprising sense and antisense sequences found in Tables 1 and 2, respectively, significantly reduce target gene lncRNA levels in vitro in a human hepatocellular carcinoma cell line. All sense sequences in Table 1 have the following modification: TEG-Chl, wherein Chl stands for cholesterol and TEG is a linker. Data were normalized, using geometric average, to a panel of 4 house-keeping genes and graphed with respect to the mock (non-transfected) control. Samples were run in biological duplicates.

The human MALAT1 sequence is represented by GenBank accession number EF177381 (SEQ ID NO: 2), as shown below.

```
GTAAAGGACTGGGGCCCCGCAACTGGCCTCTCCTGCCCTCTTAAGCGCAG

CGCCATTTTAGCAACGCAGAAGCCCGGCGCCGGGAAGCCTCAGCTCGCCT

GAAGGCAGGTCCCCTCTGACGCCTCCGGGAGCCCAGGTTTCCCAGAGTCC

TTGGGACGCAGCGACGAGTTGTGCTGCTATCTTAGCTGTCCTTATAGGCT

GGCCATTCCAGGTGGTGGTATTTAGATAAAACCACTCAAACTCTGCAGTT

TGGTCTTGGGGTTTGGAGGAAAGCTTTTATTTTTCTTCCTGCTCCGGTTC

AGAAGGTCTGAAGCTCATACCTAACCAGGCATAACACAGAATCTGCAAAA

CAAAAACCCCTAAAAAAGCAGACCCAGAGCAGTGTAAACACTTCTGGGTG

TGTCCCTGACTGGCTGCCCAAGGTCTCTGTGTCTTCGGAGACAAAGCCAT

TCGCTTAGTTGGTCTACTTTAAAAGGCCACTTGAACTCGCTTTCCATGGC

GATTTGCCTTGTGAGCACTTTCAGGAGAGCCTGGAAGCTGAAAAACGGTA

GAAAAATTTCCGTGCGGGCCGTGGGGGGCTGGCGGCAACTGGGGGGCCGC

AGATCAGAGTGGGCCACTGGCAGCCAACGGCCCCGGGGCTCAGGCGGGG

AGCAGCTCTGTGGTGTGGGATTGAGGCGTTTTCCAAGAGTGGGTTTTCAC

GTTTCTAAGATTTCCCAAGCAGACAGCCCGTGCTGCTCCGATTTCTCGAA

CAAAAAAGCAAAACGTGTGGCTGTCTTGGGAGCAAGTCGCAGGACTGCAA

GCAGTTGGGGGAGAAAGTCCGCCATTTTGCCCACTTCTCAACCGTCCCTGC

AAGGCTGGGGCTCAGTTGCGTAATGGAAAGTAAAGCCCTGAACTATCACA

CTTTAATCTTCCTTCAAAAGGTGGTAAACTATACCTACTGTCCCTCAAGA

GAACACAAGAAGTGCTTTAAGAGGTATTTTAAAAGTTCCGGGGGTTTTGT

GAGGTGTTTGATGACCCGTTTAAAATATGATTTCCATGTTTCTTTTGTCT

AAAGTTTGCAGCTCAAATCTTTCCACACGCTAGTAATTTAAGTATTTCTG

CATGTGTAGTTTGCATTCAAGTTCCATAAGCTGTTAAGAAAAATCTAGAA

AAGTAAAACTAGAACCTATTTTTAACCGAAGAACTACTTTTTGCCTCCCT

CACAAAGGCGGCGGAAGGTGATCGAATTCCGGTGATGCGAGTTGTTCTCC

GTCTATAAATACGCCTCGCCCGAGCTGTGCGGTAGGCATTGAGGCAGCCA

GCGCAGGGGCTTCTGCTGAGGGGGCAGGCGGAGCTTGAGGAAACCGCAGA

TAAGTTTTTTTCTCTTTGAAAGATAGAGATTAATACAACTACTTAAAAAA

TATAGTCAATAGGTTACTAAGATATTGCTTAGCGTTAAGTTTTTAACGTA

ATTTTAATAGCTTAAGATTTTAAGAGAAAATATGAAGACTTAGAAGAGTA

GCATGAGGAAGGAAAAGATAAAAGGTTTCTAAAACATGACGGAGGTTGAG

ATGAAGCTTCTTCATGGAGTAAAAAATGTATTTAAAAGAAAATTGAGAGA

AAGGACTACAGAGCCCCGAATTAATACCAATAGAAGGGCAATGCTTTTAG

ATTAAAATGAAGGTGACTTAAACAGCTTAAAGTTTAGTTTAAAAGTTGTA

GGTGATTAAAATAATTTGAAGGCGATCTTTTAAAAAGAGATTAAACCGAA

GGTGATTAAAAGACCTTGAAATCCATGACGCAGGGAGAATTGCGTCATTT

AAAGCCTAGTTAACGCATTTACTAAACGCAGACGAAAATGGAAAGATTAA

TTGGGAGTGGTAGGATGAAACAATTTGGAGAAGATAGAAGTTTGAAGTGG

AAAACTGGAAGACAGAAGTACGGGAAGGCGAAGAAAAGAATAGAGAAGAT

AGGGAAATTAGAAGATAAAAACATACTTTTAGAAGAAAAAAGATAAATTT

AAACCTGAAAAGTAGGAAGCAGAAGAAAAAAGACAAGCTAGGAAACAAAA

AGCTAAGGGCAAAATGTACAAACTTAGAAGAAAATTGGAAGATAGAAACA

AGATAGAAAATGAAATATTGTCAAGAGTTTCAGATAGAAAATGAAAAAC

AAGCTAAGACAAGTATTGGAGAAGTATAGAAGATAGAAAAATATAAAGCC

AAAAATTGGATAAAATAGCACTGAAAAAATGAGGAAATTATTGGTAACCA

ATTTATTTTAAAAGCCCATCAATTTAATTTCTGGTGGTGCAGAAGTTAGA

AGGTAAAGCTTGAGAAGATGAGGGTGTTTACGTAGACCAGAACCAATTTA

GAAGAATACTTGAAGCTAGAAGGGGAAGTTGGTTAAAAATCACATCAAAA
```

AGCTACTAAAAGGACTGGTGTAATTTAAAAAAAACTAAGGCAGAAGGCTT
TTGGAAGAGTTAGAAGAATTTGGAAGGCCTTAAATATAGTAGCTTAGTTT
GAAAAATGTGAAGGACTTTCGTAACGGAAGTAATTCAAGATCAAGAGTAA
TTACCAACTTAATGTTTTTGCATTGGACTTTGAGTTAAGATTATTTTTTA
AATCCTGAGGACTAGCATTAATTGACAGCTGACCCAGGTGCTACACAGAA
GTGGATTCAGTGAATCTAGGAAGACAGCAGCAGACAGGATTCCAGGAACC
AGTGTTTGATGAAGCTAGGACTGAGGAGCAAGCGAGCAAGCAGCAGTTCG
TGGTGAAGATAGGAAAAGAGTCCAGGAGCCAGTGCGATTTGGTGAAGGAA
GCTAGGAAGAAGGAAGGAGCGCTAACGATTTGGTGGTGAAGCTAGGAAAA
AGGATTCCAGGAAGGAGCGAGTGCAATTTGGTGATGAAGGTAGCAGGCGG
CTTGGCTTGGCAACCACACGGAGGAGGCGAGCAGGCGTTGTGCGTAGAGG
ATCCTAGACCAGCATGCCAGTGTGCCAAGGCCACAGGGAAAGCGAGTGGT
TGGTAAAAATCCGTGAGGTCGGCAATATGTTGTTTTTCTGGAACTTACTT
ATGGTAACCTTTTATTTATTTTCTAATATAATGGGGGAGTTTCGTACTGA
GGTGTAAAGGGATTTATATGGGACGTAGGCCGATTTCCGGGTGTTGTAG
GTTTCTCTTTTTCAGGCTTATACTCATGAATCTTGTCTGAAGCTTTTGAG
GGCAGACTGCCAAGTCCTGGAGAAATAGTAGATGGCAAGTTTGTGGGTTT
TTTTTTTTTTACACGAATTTGAGGAAAACCAAATGAATTTGATAGCCAAAT
TGAGACAATTTCAGCAAATCTGTAAGCAGTTTGTATGTTTAGTTGGGGTA
ATGAAGTATTTCAGTTTTGTGAATAGATGACCTGTTTTTACTTCCTCACC
CTGAATTCGTTTTGTAAATGTAGAGTTTGGATGTGTAACTGAGGCGGGGG
GGAGTTTTCAGTATTTTTTTTGTGGGGGTGGGGCAAAATATGTTTTCA
GTTCTTTTTCCCTTAGGTCTGTCTAGAATCCTAAAGGCAAATGACTCAAG
GTGTAACAGAAAACAAGAAAATCCAATATCAGGATAATCAGACCACCACA
GGTTTACAGTTTATAGAAACTAGAGCAGTTCTCACGTTGAGGTCTGTGGA
AGAGATGTCCATTGGAGAAATGGCTGGTAGTTACTCTTTTTTCCCCCCAC
CCCCTTAATCAGACTTTAAAAGTGCTTAACCCCTTAAACTTGTTATTTTT
TACTTGAAGCATTTTGGGATGGTCTTAACAGGGAAGAGAGAGGGTGGGGG
AGAAAATGTTTTTTTCTAAGATTTTCCACAGATGCTATAGTACTATTGAC
AAACTGGGTTAGAGAAGGAGTGTACCGCTGTGCTGTTGGCACGAACACCT
TCAGGGACTGGAGCTGCTTTTATCCTTGGAAGAGTATTCCCAGTTGAAGC
TGAAAAGTACAGCACAGTGCAGCTTTGGTTCATATTCAGTCATCTCAGGA
GAACTTCAGAAGAGCTTGAGTAGGCCAAATGTTGAAGTTAAGTTTTCCAA
TAATGTGACTTCTTAAAAGTTTTATTAAAGGGGAGGGGCAAATATTGGCA
ATTAGTTGGCAGTGGCCTGTTACGGTTGGGATTGTGGGGTGGGTTTAGG
TAATTGTTTAGTTTATGATTGCAGATAAACTCATGCCAGAGAACTTAAAG
TCTTAGAATGGAAAAGTAAAGAAATATCAACTTCCAAGTTGGCAAGTAA
CTCCCAATGATTTAGTTTTTTTCCCCCCAGTTTGAATTGGGAAGCTGGGG
GAAGTTAAATATGAGCCACTGGGTGTACCAGTGCATTAATTTGGGCAAGG
AAAGTGTCATAATTTGATACTGTATCTGTTTTCCTTCAAAGTATAGAGCT

TTTGGGGAAGGAAAGTATTGAACTGGGGGTTGGTCTGGCCTACTGGGCTG
ACATTAACTACAATTATGGGAAATGCAAAAGTTGTTTGGATATGGTAGTG
TGTGGTTCTCTTTTGGAATTTTTTTCAGGTGATTTAATAATAATTTAAAA
CTACTATAGAAACTGCAGAGCAAAGGAAGTGGCTTAATGATCCTGAAGGG
ATTTCTTCTGATGGTAGCTTTTGTATTATCAAGTAAGATTCTATTTTCAG
TTGTGTGTAAGCAAGTTTTTTTTAGTGTAGGAGAAATACTTTTCCATTG
TTTAACTGCAAAACAAGATGTTAAGGTATGCTTCAAAAATTTTGTAAATT
GTTTATTTTAAACTTATCTGTTTGTAAATTGTAACTGATTAAGAATTGTG
ATAGTTCAGCTTGAATGTCTCTTAGAGGGTGGGCTTTTGTTGATGAGGGA
GGGGAAACTTTTTTTTTTTCTATAGACTTTTTTCAGATAACATCTTCTGA
GTCATAACCAGCCTGGCAGTATGATGGCCTAGATGCAGAGAAAACAGCTC
CTTGGTGAATTGATAAGTAAAGGCAGAAAAGATTATATGTCATACCTCCA
TTGGGGAATAAGCATAACCCTGAGATTCTTACTACTGATGAGAACATTAT
CTGCATATGCCAAAAAATTTTAAGCAAATGAAAGCTACCAATTTAAAGTT
ACGGAATCTACCATTTTAAAGTTAATTGCTTGTCAAGCTATAACCACAAA
AATAATGAATTGATGAGAAATACAATGAAGAGGCAATGTCCATCTCAAAA
TACTGCTTTTACAAAAGCAGAATAAAAGCGAAAAGAAATGAAAATGTTAC
ACTACATTAATCCTGGAATAAAAGAAGCCGAAATAAATGAGAGATGAGTT
GGGATCAAGTGGATTGAGGAGGCTGTGCTGTGTGCCAATGTTTCGTTTGC
CTCAGACAGGTATCTCTTCGTTATCAGAAGAGTTGCTTCATTTCATCTGG
GAGCAGAAAACAGCAGGCAGCTGTTAACAGATAAGTTTAACTTGCATCTG
CAGTATTGCATGTTAGGGATAAGTGCTTATTTTTAAGAGCTGTGGAGTTC
TTAAATATCAACCATGGCACTTTCTCCTGACCCCTTCCCTAGGGGATTTC
AGGATTGAGAAATTTTTCCATCGAGCCTTTTTAAAATTGTAGGACTTGTT
CCTGTGGGCTTCAGTGATGGGATAGTACACTTCACTCAGAGGCATTTGCA
TCTTTAAATAATTTCTTAAAAGCCTCTAAAGTGATCAGTGCCTTGATGCC
AACTAAGGAAATTTGTTTAGCATTGAATCTCTGAAGGCTCTATGAAAGGA
ATAGCATGATGTGCTGTTAGAATCAGATGTTACTGCTAAAATTTACATGT
TGTGATGTAAATTGTGTAGAAAACCATTAAATCATTCAAAATAATAAACT
ATTTTTATTAGAGAATGTATACTTTTAGAAAGCTGTCTCCTTATTTAAAT
AAAATAGTGTTTGTCTGTAGTTCAGTGTTGGGGCAATCTTGGGGGGGATT
CTTCTCTAATCTTTCAGAAACTTTGTCTGCGAACACTCTTTAATGGACCA
GATCAGGATTTGAGCGGAAGAACGAATGTAACTTTAAGGCAGGAAAGACA
AATTTTATTCTTCATAAAGTGATGAGCATATAATAATTCCAGGCACATGG
CAATAGAGGCCCTCTAAATAAGGAATAAATAACCTCTTAGACAGGTGGGA
GATTATGATCAGAGTAAAAGGTAATTACACATTTTATTTCCAGAAAGTCA
GGGGTCTATAAATTGACAGTGATTAGAGTAATACTTTTTCACATTTCCAA
AGTTTGCATGTTAACTTTAAATGCTTACAATCTTAGAGTGGTAGGCAATG
TTTTACACTATTGACCTTATATAGGGAAGGGAGGGGGTGCCTGTGGGGTT
TTAAAGAATTTTCCTTTGCAGAGGCATTTCATCCTTCATGAAGCCATTCA
GGATTTTGAATTGCATATGAGTGCTTGGCTCTTCCTTCTGTTCTAGTGAG

TGTATGAGACCTTGCAGTGAGTTTATCAGCATACTCAAAATTTTTTCCT

GGAATTTGGAGGGATGGGAGGAGGGGGTGGGGCTTACTTGTTGTAGCTTT

TTTTTTTTTTACAGACTTCACAGAGAATGCAGTTGTCTTGACTTCAGGTC

TGTCTGTTCTGTTGGCAAGTAAATGCAGTACTGTTCTGATCCCGCTGCTA

TTAGAATGCATTGTGAAACGACTGGAGTATGATTAAAAGTTGTGTTCCCC

AATGCTTGGAGTAGTGATTGTTGAAGGAAAAAATCCAGCTGAGTGATAAA

GGCTGAGTGTTGAGGAAATTTCTGCAGTTTTAAGCAGTCGTATTTGTGAT

TGAAGCTGAGTACATTTTGCTGGTGTATTTTTAGGTAAAATGCTTTTTGT

TCATTTCTGGTGGTGGGAGGGGACTGAAGCCTTTAGTCTTTTCCAGATGC

AACCTTAAAATCAGTGACAAGAAACATTCCAAACAAGCAACAGTCTTCAA

GAAATTAAACTGGCAAGTGGAAATGTTTAAACAGTTCAGTGATCTTTAGT

GCATTGTTTATGTGTGGGTTTCTCTCTCCCCTCCCTTGGTCTTAATTCTT

ACATGCAGGAACACTCAGCAGACACACGTATGCGAAGGGCCAGAGAAGCC

AGACCCAGTAAGAAAAAATAGCCTATTTACTTTAAATAAACCAAACATTC

CATTTTAAATGTGGGGATTGGGAACCACTAGTTCTTTCAGATGGTATTCT

TCAGACTATAGAAGGAGCTTCCAGTTGAATTCACCAGTGGACAAAATGAG

GAAAACAGGTGAACAAGCTTTTTCTGTATTTACATACAAAGTCAGATCAG

TTATGGGACAATAGTATTGAATAGATTTCAGCTTTATGCTGGAGTAACTG

GCATGTGAGCAAACTGTGTTGGCGTGGGGGTGGAGGGGTGAGGTGGGCGC

TAAGCCTTTTTTTAAGATTTTTCAGGTACCCCTCACTAAAGGCACCGAAG

GCTTAAAGTAGGACAACCATGGAGCCTTCCTGTGGCAGGAGAGACAACAA

AGCGCTATTATCCTAAGGTCAAGAGAAGTGTCAGCCTCACCTGATTTTTA

TTAGTAATGAGGACTTGCCTCAACTCCCTCTTTCTGGAGTGAAGCATCCG

AAGGAATGCTTGAAGTACCCCTGGGCTTCTCTTAACATTTAAGCAAGCTG

TTTTTATAGCAGCTCTTAATAATAAAGCCCAAATCTCAAGCGGTGCTTGA

AGGGGAGGGAAAGGGGGAAAGCGGGCAACCACTTTTCCCTAGCTTTTCCA

GAAGCCTGTTAAAAGCAAGGTCTCCCCACAAGCAACTTCTCTGCCACATC

GCCACCCCGTGCCTTTTGATCTAGCACAGACCCTTCACCCCTCACCTCGA

TGCAGCCAGTAGCTTGGATCCTTGTGGGCATGATCCATAATCGGTTTCAA

GGTAACGATGGTGTCGAGGTCTTTGGTGGGTTGAACTATGTTAGAAAAGG

CCATTAATTTGCCTGCAAATTGTTAACAGAAGGGTATTAAAACCACAGCT

AAGTAGCTCTATTATAATACTTATCCAGTGACTAAAACCAACTTAAACCA

GTAAGTGGAGAAATAACATGTTCAAGAACTGTAATGCTGGGTGGGAACAT

GTAACTTGTAGACTGGAGAAGATAGGCATTTGAGTGGCTGAGAGGGCTTT

TGGGTGGGAATGCAAAAATTCTCTGCTAAGACTTTTTCAGGTGAACATAA

CAGACTTGGCCAAGCTAGCATCTTAGCGGAAGCTGATCTCCAATGCTCTT

CAGTAGGGTCATGAAGGTTTTTCTTTTCCTGAGAAAACAACACGTATTGT

TTTCTCAGGTTTTGCTTTTTGGCCTTTTTCTAGCTTAAAAAAAAAAAAAG

CAAAAGATGCTGGTGGTTGGCACTCCTGGTTTCCAGGACGGGGTTCAAAT

CCCTGCGGCGTCTTTGCTTTGACTACTAATCTGTCTTCAGGACTCTTTCT

GTATTTCTCCTTTTCTCTGCAGGTGCTAGTTCTTGGAGTTTTGGGGAGGT

GGGAGGTAACAGCACAATATCTTTGAACTATATACATCCTTGATGTATAA

TTTGTCAGGAGCTTGACTTGATTGTATATTCATATTTACACGAGAACCTA

ATATAACTGCCTTGTCTTTTTCAGGTAATAGCCTGCAGCTGGTGTTTTGA

GAAGCCCTACTGCTGAAAACTTAACAATTTTGTGTAATAAAAATGGAGAA

GCTCTAAA

Figure 3:
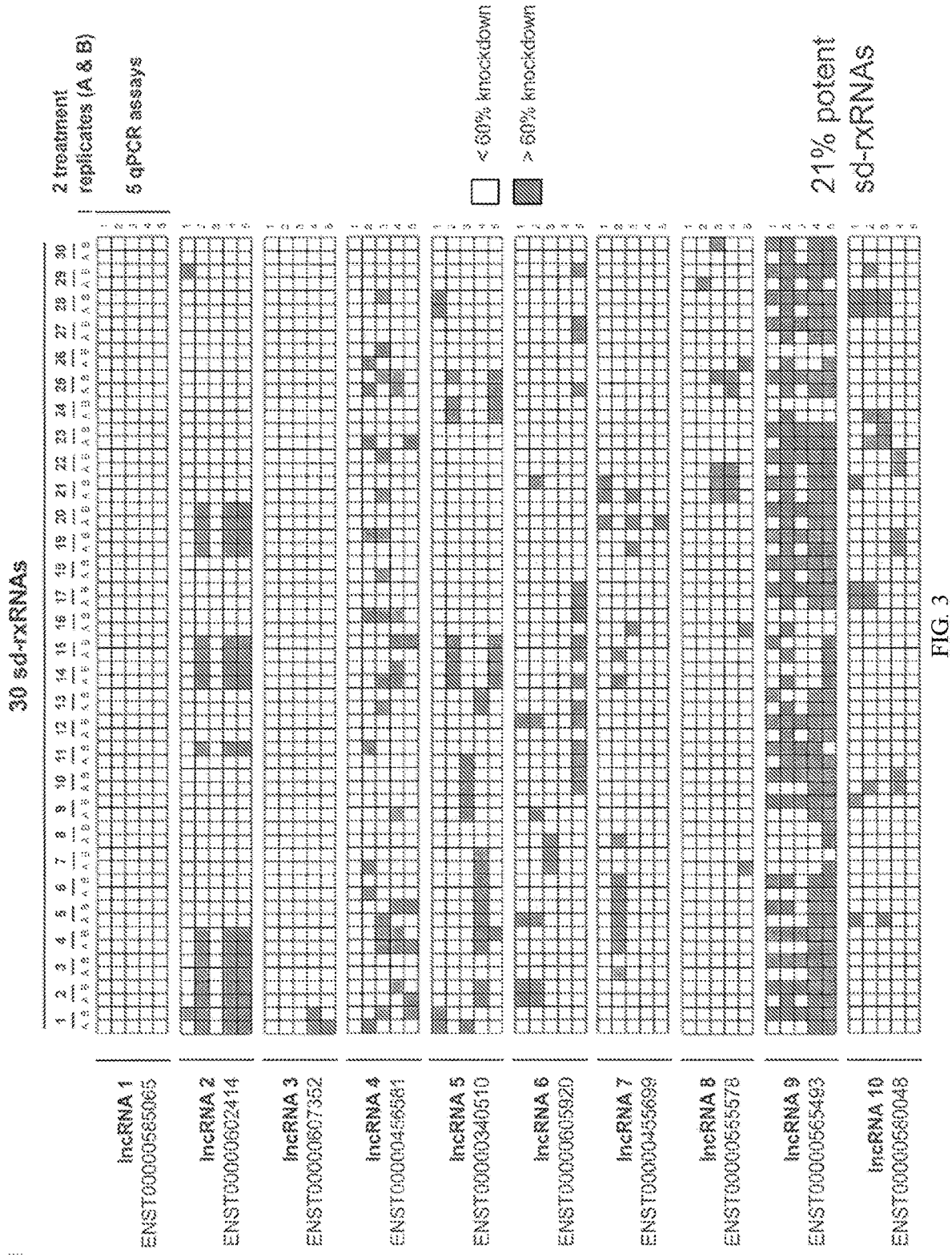
FIG. 3 shows identification of potent sd-rxRNAs targeting lncRNAs. The lncRNA-targeting sd-rxRNAs described in this particular assay significantly reduced target gene lncRNA levels in vitro in a human hepatocarcinoma cell line or a human colorectal carcinoma cell line.

Example 3: Identification of Sd-rxRNAs Targeting lncRNAs sd-rxRNAs targeting the following lncRNAs; ENST00000585065, ENST00000607352, ENST00000456581, ENST00000340510, ENST00000605920, ENST00000455699, ENST00000555578, ENST00000565493, 580048 were designed, synthesized and screened in vitro to determine the ability of the sd-rxRNAs to reduce target lncRNA levels. The sd-rxRNAs were tested for activity in a human hepatocellular carcinoma cell line (40,000 cells/well, 96 well plate) or a human colorectal carcinoma cell line (40,000 cells/well, 96 well plate). Cells were treated with a panel of lncRNA-targeting sd-rxRNAs or non-targeting control (#26247) in media containing 10% FCS. The concentration of sd-rxRNA tested was 5 µM. The non-targeting control sd-rxRNA (#26247) is of similar structure to the lncRNA-targeting sd-rxRNAs and contains similar stabilizing modifications throughout both strands. Forty eight hours post-administration, cells were lysed and lncRNA levels determined with lncRNA-specific SYBR Green I qPCR assays and SsoAdvanced Universal SYBR Green Supermix (Bio-Rad) according to manufacturer's protocol. FIG. 3 demonstrates the lncRNA-targeting sd-rxRNAs, comprising sense and antisense sequences found in Tables 1 and 2, respectively, significantly reduce target gene lncRNA levels in vitro in a human hepatocellular carcinoma cell line or a human colorectal carcinoma cell line. All sense sequences in Table 1 have the following modification: TEG-Chl, wherein Chl stands for cholesterol and TEG is a linker. Data were normalized, using geometric average, to a panel of 4 housekeeping genes and graphed with respect to the mock (non-transfected) control. Samples were run in biological duplicates.

TABLE 1

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncRala1 1 | LNC Rala1 | ENST00000 340510 | 140 | 3 | CCGCUUCAGA AUCA | mm0mmmm00m 0mmm | oooooooo oosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncRala1 2 | LNC Rala1 | ENST00000340510 | 296 | 4 | UGAUCCCGAGCCUA | mm0mmmm000mmmm | oooooooooosso |
| lncRala1 3 | LNC Rala1 | ENST00000340510 | 366 | 5 | UUUUUCCGCUGUAA | mmmmmmm0mm0mmm | oooooooooosso |
| lncRala1 4 | LNC Rala1 | ENST00000340510 | 367 | 6 | UUUUCCGCUGUAAA | mmmmmm0mm0mm | oooooooooosso |
| lncRala1 5 | LNC Rala1 | ENST00000340510 | 368 | 7 | UUUCCGCUGUAAAA | mmmmm0mm0m00mm | oooooooooosso |
| lncRala1 6 | LNC Rala1 | ENST00000340510 | 369 | 8 | UUCCGCUGUAAUA | mmmm0mm0m00mm | oooooooooosso |
| lncRala1 7 | LNC Rala1 | ENST00000340510 | 370 | 9 | UCCGCUGUAAAUAA | mmm0mm0m000mmm | oooooooooosso |
| lncRala1 8 | LNC Rala1 | ENST00000340510 | 487 | 10 | GCCAAGCGGAAUUA | mmm000m0m0mmm | oooooooooosso |
| lncRala1 9 | LNC Rala1 | ENST00000340510 | 488 | 11 | CCAAGCGGAAUUUA | mm000m0000mmmm | oooooooooosso |
| lncRala1 10 | LNC Rala1 | ENST00000340510 | 489 | 12 | CAAGCGGAAUUUAA | mm00m00m0mmmmmm | oooooooooosso |
| lncRala1 11 | LNC Rala1 | ENST00000340510 | 490 | 13 | AAGCGGAAUUUAAA | mm0m00m0mmm0mm | oooooooooosso |
| lncRala1 12 | LNC Rala1 | ENST00000340510 | 491 | 14 | AGCGGAAUUUAAAA | mmm00m0mmm00mm | oooooooooosso |
| lncRala1 13 | LNC Rala1 | ENST00000340510 | 492 | 15 | GCGGAAUUUAAAUA | mm00m0mmm000mm | oooooooooosso |
| lncRala1 14 | LNC Rala1 | ENST00000340510 | 620 | 16 | UGAGCCGCAGAGAA | mm00mm0m00m0mm | oooooooooosso |
| lncRala1 15 | LNC Rala1 | ENST00000340510 | 622 | 17 | AGCCGCAGAGAUCA | mmmm0m00m00mmm | oooooooooosso |
| lncRala1 16 | LNC Rala1 | ENST00000340510 | 852 | 18 | UACCACGUCAGUCA | mmmm0m0mm00mmm | oooooooooosso |
| lncRala1 17 | LNC Rala1 | ENST00000340510 | 853 | 19 | ACCACGUCAGUCUA | mmm0m0mm00mmmm | oooooooooosso |
| lncRala1 18 | LNC Rala1 | ENST00000340510 | 1662 | 20 | ACGAGCUUAACACA | mm000mmm00m0mm | oooooooooosso |
| lncRala1 19 | LNC Rala1 | ENST00000340510 | 1663 | 21 | CGAGCUUAACACGA | mmm0mmm00m0mmm | oooooooooosso |
| lncRala1 20 | LNC Rala1 | ENST00000340510 | 1664 | 22 | GAGCUUAACACGCA | mm0mmm00m0m0mm | oooooooooosso |
| lncRala1 21 | LNC Rala1 | ENST00000340510 | 1205 | 23 | CCUUUCGAAUGCAA | mmmmmm000m0mmm | oooooooooosso |
| lncRala1 22 | LNC Rala1 | ENST00000340510 | 1208 | 24 | UUCGAAUGCACUUA | mmm000m0m0mmmm | oooooooooosso |
| lncRala1 23 | LNC Rala1 | ENST00000340510 | 1926 | 25 | UCAAGUCGACGUCA | mm000mm00m0mmm | oooooooooosso |
| lncRala1 24 | LNC Rala1 | ENST00000340510 | 2933 | 26 | AGGCCCCGAACUUA | mm0mmmm000mmmm | oooooooooosso |
| lncRala1 25 | LNC Rala1 | ENST00000340510 | 1857 | 27 | CCAUCGUUACAAUA | mm0mm0mm0m00mm | oooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncRala1 26 | LNC Rala1 | ENST00000340510 | 1203 | 28 | AUCCUUUCGAAUGA | mmmmmmmm00 0mm | oooooooo oosso |
| lncRala1 27 | LNC Rala1 | ENST00000340510 | 1784 | 29 | GGCCCAUACCCUAA | mmmmm0m0mm mmmm | oooooooo oosso |
| lncRala1 28 | LNC Rala1 | ENST00000340510 | 99 | 30 | UAUAGACCCUGAAA | mmm000mmmm 00mm | oooooooo oosso |
| lncRala1 29 | LNC Rala1 | ENST00000340510 | 1480 | 31 | UAGUGCUAUCACAA | mm0m0mm0mm 0mm | oooooooo oosso |
| lncRala1 30 | LNC Rala1 | ENST00000340510 | 1154 | 32 | GUUGACCACUGCAA | mmm00mm0mm 0mm | oooooooo oosso |
| lncZBTB42 1 | LNC ZBTB42 | ENST00000555578 | 588 | 33 | UCUGCCCGAAUCUA | mmm0mmm000 mmm | oooooooo oosso |
| lncZBTB42 2 | LNC ZBTB42 | ENST00000555578 | 590 | 34 | UGCCCGAAUCUUCA | mmmmm000mm mmmm | oooooooo oosso |
| lncZBTB42 3 | LNC ZBTB42 | ENST00000555578 | 593 | 35 | CCGAAUCUUCACAA | mm000mmmmm 0mm | oooooooo oosso |
| lncZBTB42 4 | LNC ZBTB42 | ENST00000555578 | 801 | 36 | AAUUCGACCCGUAA | mmmmm00mmm 0mm | oooooooo oosso |
| lncZBTB42 5 | LNC ZBTB42 | ENST00000555578 | 804 | 37 | UCGACCCGUAACAA | mm00mmm0m00 mmm | oooooooo oosso |
| lncZBTB42 6 | LNC ZBTB42 | ENST00000555578 | 807 | 38 | ACCCGUAACAGCUA | mmmm0m0m00 mmm | oooooooo oosso |
| lncZBTB42 7 | LNC ZBTB42 | ENST00000555578 | 836 | 39 | UCCGAUGUGCUUCA | mmm00m0m0m mmmm | oooooooo oosso |
| lncZBTB42 8 | LNC ZBTB42 | ENST00000555578 | 960 | 40 | ACGGACCUUUAUUA | mm000mmmmm 0mm | oooooooo oosso |
| lncZBTB42 9 | LNC ZBTB42 | ENST00000555578 | 1073 | 41 | UCUCCGAAGAGAUA | mmmmm000m00 0mm | oooooooo oosso |
| lncZBTB42 10 | LNC ZBTB42 | ENST00000555578 | 1075 | 42 | UCCGAAGAGAUUCA | mmm000mm000m mmm | oooooooo oosso |
| lncZBTB42 11 | LNC ZBTB42 | ENST00000555578 | 1076 | 43 | CCGAAGAGAUUCCA | mm000m000mm mmm | oooooooo oosso |
| lncZBTB42 12 | LNC ZBTB42 | ENST00000555578 | 1281 | 44 | AGCCGAUUAGCUGA | mmmm00mm00 mmmm | oooooooo oosso |
| lncZBTB42 13 | LNC ZBTB42 | ENST00000555578 | 1581 | 45 | CUUAUCGCCACACA | mmm0mm0mm0 m0mm | oooooooo oosso |
| lncZBTB42 14 | LNC ZBTB42 | ENST00000555578 | 2212 | 46 | UGGACGUUUGAAAA | mm00m0mmm00 0mm | oooooooo oosso |
| lncZBTB42 15 | LNC ZBTB42 | ENST00000555578 | 2213 | 47 | GGACGUUUGAAAAA | mm0m0mmm00 m0mm | oooooooo oosso |
| lncZBTB42 16 | LNC ZBTB42 | ENST00000555578 | 2137 | 48 | UAGGCCUAAUCAAA | mm00mmm00m m0mm | oooooooo oosso |
| lncZBTB42 17 | LNC ZBTB42 | ENST00000555578 | 2141 | 49 | CCUAAUCAACGUAA | mmm00mm00m0 mmm | oooooooo oosso |
| lncZBTB42 18 | LNC ZBTB42 | ENST00000555578 | 636 | 50 | UUCCCGUCUUUAUA | mmmmm0mmm mm0mm | oooooooo oosso |
| lncZBTB42 19 | LNC ZBTB42 | ENST00000555578 | 1574 | 51 | ACACAAGCUUAUCA | mm0m000mmm0 mmm | oooooooo oosso |
| lncZBTB42 20 | LNC ZBTB42 | ENST00000555578 | 1575 | 52 | CACAAGCUUAUCGA | mmm000mmm0 mmmm | oooooooo oosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncZBTB42 21 | LNC ZBTB42 | ENST00000 555578 | 694 | 53 | CUCACCCUAA CUUA | mmm0mmmm00 mmmm | oooooooo oosso |
| lncZBTB42 22 | LNC ZBTB42 | ENST00000 555578 | 699 | 54 | CCUAACUUGA UGGA | mmm00mmm00 m0mm | oooooooo oosso |
| lncZBTB42 23 | LNC ZBTB42 | ENST00000 555578 | 2145 | 55 | AUCAACGUAA AUCA | mmm00m0m000 mmm | oooooooo oosso |
| lncZBTB42 24 | LNC ZBTB42 | ENST00000 555578 | 2149 | 56 | ACGUAAAUCU GUCA | mm0m000mmm0 mmm | oooooooo oosso |
| lncZBTB42 25 | LNC ZBTB42 | ENST00000 555578 | 700 | 57 | CUAACUUGAU GGAA | mm00mmm00m0 0mm | oooooooo oosso |
| lncZBTB42 26 | LNC ZBTB42 | ENST00000 555578 | 2134 | 58 | AGUUAGGCCU AAUA | mmmm000mmm 00mm | oooooooo oosso |
| lncZBTB42 27 | LNC ZBTB42 | ENST00000 555578 | 1307 | 59 | GUGUAAGGAC UGCA | mm0m00m0mm 0mm | oooooooo oosso |
| lncZBTB42 28 | LNC ZBTB42 | ENST00000 555578 | 640 | 60 | CGUCUUUAUA AGGA | mmmmmmm0m0 00mm | oooooooo oosso |
| lncZBTB42 29 | LNC ZBTB42 | ENST00000 555578 | 1616 | 61 | CCUGGAUUAC AAGA | mmm000mm0m0 0mm | oooooooo oosso |
| lncZBTB42 30 | LNC ZBTB42 | ENST00000 555578 | 2133 | 62 | GAGUUAGGCC UAAA | mm0mm000mmm m0mm | oooooooo oosso |
| lncPANK1 1 | LNC PANK1 | ENST00000 455699 | 174 | 63 | AUUGGAGCUC AACA | mmm00m0mmm 00mm | oooooooo oosso |
| lncPANK1 2 | LNC PANK1 | ENST00000 455699 | 176 | 64 | UGGAGCUCAA CUAA | mm000mmm00m mmm | oooooooo oosso |
| lncPANK1 3 | LNC PANK1 | ENST00000 455699 | 179 | 65 | AGCUCAACUA CCGA | mmmmm00mm0 mmmm | oooooooo oosso |
| lncPANK1 4 | LNC PANK1 | ENST00000 455699 | 188 | 66 | ACCGACUGUG UCAA | mmm00mm0m0 mmmm | oooooooo oosso |
| lncPANK1 5 | LNC PANK1 | ENST00000 455699 | 191 | 67 | GACUGUGUCA AUCA | mmmm0m0m0 0mmm | oooooooo oosso |
| lncPANK1 6 | LNC PANK1 | ENST00000 455699 | 211 | 68 | AGUAUCAGGU UCCA | mmm0mm000m mmmm | oooooooo oosso |
| lncPANK1 7 | LNC PANK1 | ENST00000 455699 | 419 | 69 | GGUCUAUAGU CUUA | mmmmm0m00m mmmm | oooooooo oosso |
| lncPANK1 8 | LNC PANK1 | ENST00000 455699 | 565 | 70 | CUUGUAUCCG UAAA | mmm0m0mmm0 m0mm | oooooooo oosso |
| lncPANK1 9 | LNC PANK1 | ENST00000 455699 | 568 | 71 | GUAUCCGUAA GUCA | mm0mmm0m000 mmm | oooooooo oosso |
| lncPANK1 10 | LNC PANK1 | ENST00000 455699 | 571 | 72 | UCCGUAAGUC ACAA | mmm0m000mm0 mmm | oooooooo oosso |
| lncPANK1 11 | LNC PANK1 | ENST00000 455699 | 573 | 73 | CGUAAGUCAC ACAA | mmm000mm0m mmm | oooooooo oosso |
| lncPANK1 12 | LNC PANK1 | ENST00000 455699 | 636 | 74 | AAAUGUCGAA AAGA | mm0m0mm000m 0mm | oooooooo oosso |
| lncPANK1 13 | LNC PANK1 | ENST00000 455699 | 415 | 75 | UGCAGGUCUA UAGA | mmm000mmm0 m0mm | oooooooo oosso |
| lncPANK1 14 | LNC PANK1 | ENST00000 455699 | 418 | 76 | AGGUCUAUAG UCUA | mm0mmm0m00 mmmm | oooooooo oosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncPANK1 15 | LNC PANK1 | ENST00000 455699 | 505 | 77 | AGGAUUAUA UGCCA | mm00mm0m0m0 mmm | ooooooooo oosso |
| lncPANK1 16 | LNC PANK1 | ENST00000 455699 | 259 | 78 | AGACAAUACC AGAA | mm0m00m0mm0 0mm | ooooooooo oosso |
| lncPANK1 17 | LNC PANK1 | ENST00000 455699 | 421 | 79 | UCUAUAGUCU UUAA | mmm0m00mmm mmmm | ooooooooo oosso |
| lncPANK1 18 | LNC PANK1 | ENST00000 455699 | 502 | 80 | ACCAGGAUUA UAUA | mmm00m0mm0 m0mm | ooooooooo oosso |
| lncPANK1 19 | LNC PANK1 | ENST00000 455699 | 341 | 81 | AGUAAUAGCU GCAA | mmm00m00mm0 mmm | ooooooooo oosso |
| lncPANK1 20 | LNC PANK1 | ENST00000 455699 | 351 | 82 | GCAUAACCUU GAGA | mm0m00mmmm 00mm | ooooooooo oosso |
| lncPANK1 21 | LNC PANK1 | ENST00000 455699 | 257 | 83 | GCAGACAAUA CCAA | mm000m00m0m mmm | ooooooooo oosso |
| lncPANK1 22 | LNC PANK1 | ENST00000 455699 | 367 | 84 | GAUACUGACU GAGA | mmm0mm00mm 00mm | ooooooooo oosso |
| lncPANK1 23 | LNC PANK1 | ENST00000 455699 | 55 | 85 | UGAGUCUUAU GUCA | mm00mmmm0m 0mmm | ooooooooo oosso |
| lncPANK1 24 | LNC PANK1 | ENST00000 455699 | 424 | 86 | AUAGUCUUUA CUCA | mm00mmmmm0 mmmm | ooooooooo oosso |
| lncPANK1 25 | LNC PANK1 | ENST00000 455699 | 253 | 87 | CUUGGCAGAC AAUA | mmm00m000m0 0mm | ooooooooo oosso |
| lncPANK1 26 | LNC PANK1 | ENST00000 455699 | 217 | 88 | AGGUUCCUGU GCUA | mm0mmmmm0m 0mmm | ooooooooo oosso |
| lncPANK1 27 | LNC PANK1 | ENST00000 455699 | 545 | 89 | AAGCCUCUAU UGUA | mm0mmmmm0m m0mmm | ooooooooo oosso |
| lncPANK1 28 | LNC PANK1 | ENST00000 455699 | 304 | 90 | CCAAAUGUUA GGAA | mm000m0mm00 0mm | ooooooooo oosso |
| lncPANK1 29 | LNC PANK1 | ENST00000 455699 | 115 | 91 | AGGAUGUAG AAGUA | mm00m0m00m0 0mm | ooooooooo oosso |
| lncPANK1 30 | LNC PANK1 | ENST00000 455699 | 150 | 92 | CAAAGCAUCU CCAA | mm000m0mmm mmmm | ooooooooo oosso |
| lncEBF3 1 | LNC EBF3 | ENST00000 456581 | 744 | 93 | UGGCGACUUU UGUA | mm0m00mmmm m0mm | ooooooooo oosso |
| lncEBF3 2 | LNC EBF3 | ENST00000 456581 | 746 | 94 | GCGACUUUUG UAUA | mm00mmmmm0 m0mm | ooooooooo oosso |
| lncEBF3 3 | LNC EBF3 | ENST00000 456581 | 1506 | 95 | UAAAGACGGA UGAA | mm0m00m000m 0mm | ooooooooo oosso |
| lncEBF3 4 | LNC EBF3 | ENST00000 456581 | 1593 | 96 | UAAAGACGAA UAUA | mm0000m000m0 mm | ooooooooo oosso |
| lncEBF3 5 | LNC EBF3 | ENST00000 456581 | 1596 | 97 | AGACGAAUAU GCUA | mm0m000m0m0 mmm | ooooooooo oosso |
| lncEBF3 6 | LNC EBF3 | ENST00000 456581 | 1652 | 98 | AGGAAUCGUC AACA | mm000mm0m0 0mm | ooooooooo oosso |
| lncEBF3 7 | LNC EBF3 | ENST00000 456581 | 1655 | 99 | AAUCGUCAAC AUCA | mmmm0mm00m 0mmm | ooooooooo oosso |
| lncEBF3 8 | LNC EBF3 | ENST00000 456581 | 1656 | 100 | AUCGUCAACA UCUA | mmm0mm00m0 mmmm | ooooooooo oosso |
| lncEBF3 9 | LNC EBF3 | ENST00000 456581 | 1657 | 101 | UCGUCAACAU CUUA | mm0mm00m0m mmmm | ooooooooo oosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncEBF3_10 | LNC_EBF3 | ENST00000456581 | 2032 | 102 | GAAGCCGUUGCAGA | mm00mm0mm0m0mm | ooooooooooosso |
| lncEBF3_11 | LNC_EBF3 | ENST00000456581 | 2209 | 103 | CCGUGGAAUUGUGA | mm0m00m0mm0mmm | ooooooooooosso |
| lncEBF3_12 | LNC_EBF3 | ENST00000456581 | 2593 | 104 | CAAUUUCGAAAGGA | mm0mmmm000m0mm | ooooooooooosso |
| lncEBF3_13 | LNC_EBF3 | ENST00000456581 | 2595 | 105 | AUUUCGAAAGGUUA | mmmmm000m00mmm | ooooooooooosso |
| lncEBF3_14 | LNC_EBF3 | ENST00000456581 | 2597 | 106 | UUCGAAAGGUUCCA | mmm000m00mmmmm | ooooooooooosso |
| lncEBF3_15 | LNC_EBF3 | ENST00000456581 | 240 | 107 | UGCUCGGCUUUUUA | mmmmm00mmmmmm | ooooooooooosso |
| lncEBF3_16 | LNC_EBF3 | ENST00000456581 | 2193 | 108 | ACAUCGUUCUCUUA | mm0m00mmmmmmmm | ooooooooooosso |
| lncEBF3_17 | LNC_EBF3 | ENST00000456581 | 1878 | 109 | CGUAAUGGUCCCAA | mmm00m00mmmmmm | ooooooooooosso |
| lncEBF3_18 | LNC_EBF3 | ENST00000456581 | 2205 | 110 | UGCUCCGUGGAAUA | mmmmmm0m00m0mm | ooooooooooosso |
| lncEBF3_19 | LNC_EBF3 | ENST00000456581 | 1511 | 111 | ACGGAUGAUUGUCA | mm000m00mm0mmm | ooooooooooosso |
| lncEBF3_20 | LNC_EBF3 | ENST00000456581 | 1843 | 112 | GUACCAGAGGUGAA | mm0mm00m0m0mm | ooooooooooosso |
| lncEBF3_21 | LNC_EBF3 | ENST00000456581 | 1879 | 113 | GUAAUGGUCCCAGA | mm00m00mmm0mm | ooooooooooosso |
| lncEBF3_22 | LNC_EBF3 | ENST00000456581 | 1354 | 114 | UGACUGGUACAGAA | mm0mm00m0m00mm | ooooooooooosso |
| lncEBF3_23 | LNC_EBF3 | ENST00000456581 | 2317 | 115 | AGUAAGACUCACAA | mmm00m0mmm0mmm | ooooooooooosso |
| lncEBF3_24 | LNC_EBF3 | ENST00000456581 | 1527 | 116 | GAGGUCCAAGCUUA | mm00mmm000mmmm | ooooooooooosso |
| lncEBF3_25 | LNC_EBF3 | ENST00000456581 | 1544 | 117 | UGUAGGCCUUUGUA | mmm000mmmm0mm | ooooooooooosso |
| lncEBF3_26 | LNC_EBF3 | ENST00000456581 | 1325 | 118 | GCCCAUGUAUCUGA | mmmm0m0mmmmmm | ooooooooooosso |
| lncEBF3_27 | LNC_EBF3 | ENST00000456581 | 2409 | 119 | CUGAUGACUUGAGA | mm00m00mmm00mm | ooooooooooosso |
| lncEBF3_28 | LNC_EBF3 | ENST00000456581 | 933 | 120 | UCUGGUAAGUUCAA | mmm00m000mmmmm | ooooooooooosso |
| lncEBF3_29 | LNC_EBF3 | ENST00000456581 | 1296 | 121 | UAAUAACCCCUUUA | mm0m00mmmmmmmm | ooooooooooosso |
| lncEBF3_30 | LNC_EBF3 | ENST00000456581 | 1297 | 122 | AAUAACCCCUUUGA | mmm00mmmmmmmmm | ooooooooooosso |
| lncScand1_1 | LNC_Scand1 | ENST00000565493 | 849 | 123 | GCCGACGUAUGAUA | mmm00m0m0m0mm | ooooooooooosso |
| lncScand1_2 | LNC_Scand1 | ENST00000565493 | 851 | 124 | CGACGUAUGAUAAA | mm0m0m0m00m0mm | ooooooooooosso |
| lncScand1_3 | LNC_Scand1 | ENST00000565493 | 985 | 125 | AUACGUCCACGUUA | mm0m0mmm0m0mmm | ooooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncScand1 4 | LNC Scand 1 | ENST00000565493 | 2663 | 126 | UAGUCCCGAUUUUA | mm0mmmm00mmmm | oooooooooosso |
| lncScand1 5 | LNC Scand 1 | ENST00000565493 | 2971 | 127 | UAUAGCGGACAAAA | m0m00m000m00mm | oooooooooosso |
| lncScand1 6 | LNC Scand 1 | ENST00000565493 | 2973 | 128 | UAGCGGACAAACUA | mm0m000m000mmm | oooooooooosso |
| lncScand1 7 | LNC Scand 1 | ENST00000565493 | 3283 | 129 | UAUAAGCGGACAUA | mmm000m000m0mm | oooooooooosso |
| lncScand1 8 | LNC Scand 1 | ENST00000565493 | 3285 | 130 | UAAGCGGACAUAGA | mm00m000m0m0mm | oooooooooosso |
| lncScand1 9 | LNC Scand 1 | ENST00000565493 | 3288 | 131 | GCGGACAUAGGAGA | mm000m0m00m0mm | oooooooooosso |
| lncScand1 10 | LNC Scand 1 | ENST00000565493 | 3312 | 132 | GUCUAGUCGAUGUA | mmmm00mm00m0mm | oooooooooosso |
| lncScand1 11 | LNC Scand 1 | ENST00000565493 | 3313 | 133 | UCUAGUCGAUGUUA | mmm00mm00m0mmm | oooooooooosso |
| lncScand1 12 | LNC Scand 1 | ENST00000565493 | 3314 | 134 | CUAGUCGAUGUUAA | mm00mm00m0mmmm | oooooooooosso |
| lncScand1 13 | LNC Scand 1 | ENST00000565493 | 4972 | 135 | UAGAGGCGUGUUGA | mm00m0m0m0mmmm | oooooooooosso |
| lncScand1 14 | LNC Scand 1 | ENST00000565493 | 654 | 136 | GCUGUCGGAAGAGA | mmm0mm000m00mm | oooooooooosso |
| lncScand1 15 | LNC Scand 1 | ENST00000565493 | 656 | 137 | UGUCGGAAGAGAGA | mmmm000m0m0mm | oooooooooosso |
| lncScand1 16 | LNC Scand 1 | ENST00000565493 | 733 | 138 | ACUGGCCGUUUAUA | mmm00mm0mmm0mm | oooooooooosso |
| lncScand1 17 | LNC Scand 1 | ENST00000565493 | 736 | 139 | GGCCGUUUAUGGAA | mmmm0mmm0m00mm | oooooooooosso |
| lncScand1 18 | LNC Scand 1 | ENST00000565493 | 991 | 140 | CCACGUUUGUUAAA | mm0m0mmm0mm0mm | oooooooooosso |
| lncScand1 19 | LNC Scand 1 | ENST00000565493 | 1057 | 141 | UAUGCUAGACUGGA | mmm0mm000mm0mm | oooooooooosso |
| lncScand1 20 | LNC Scand 1 | ENST00000565493 | 1386 | 142 | CAGCGAGGCAAGAA | mm0m00m0m000mm | oooooooooosso |
| lncScand1 21 | LNC Scand 1 | ENST00000565493 | 1459 | 143 | CAGACGAGUCCUAA | mm00m000mmmmm | oooooooooosso |
| lncScand1 22 | LNC Scand 1 | ENST00000565493 | 1778 | 144 | UGCCCGAUGUAUGA | mmmmm00m00mmm | oooooooooosso |
| lncScand1 23 | LNC Scand 1 | ENST00000565493 | 2158 | 145 | AAUUCGUAGGAAAA | mmmmm0m00m00mm | oooooooooosso |
| lncScand1 24 | LNC Scand 1 | ENST00000565493 | 3981 | 146 | AACACCCCUCUAAA | mmm0mmmmmm00m | oooooooooosso |
| lncScand1 25 | LNC Scand 1 | ENST00000565493 | 4064 | 147 | AGCGAAUGCAGACA | mmm000m0m000mm | oooooooooosso |
| lncScand1 26 | LNC Scand 1 | ENST00000565493 | 4168 | 148 | GGUCUAACCAUUGA | mmmmm00mm0mmmm | oooooooooosso |
| lncScand1 27 | LNC Scand 1 | ENST00000565493 | 4435 | 149 | UCUAGACGAUGGUA | mmm000m0m0m0mm | oooooooooosso |
| lncScand1 28 | LNC Scand 1 | ENST00000565493 | 4440 | 150 | ACGAUGGUUUAGA | mm00m00mmmm0mm | oooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncScand1 29 | LNC Scand 1 | ENST00000565493 | 4474 | 151 | GAGCGUUUUUAGUA | mm0m0mmmm00mm | oooooooooosso |
| lncScand1 30 | LNC Scand 1 | ENST00000565493 | 4535 | 152 | AGCUUUACGAAUGA | mmmmmm0m000mm | oooooooooosso |
| lncFAM69C2 1 | LNC FAM69C2 | ENST00000580048 | 166 | 153 | CCGCUAAGAGAUAA | mm0m000m00mmm | oooooooooosso |
| lncFAM69C2 2 | LNC FAM69C2 | ENST00000580048 | 240 | 154 | AAUUCGAUGAGCGA | mmmmm00m000mmm | oooooooooosso |
| lncFAM69C2 3 | LNC FAM69C2 | ENST00000580048 | 241 | 155 | AUUCGAUGAGCGCA | mmmm00m000m0mm | oooooooooosso |
| lncFAM69C2 4 | LNC FAM69C2 | ENST00000580048 | 242 | 156 | UUCGAUGAGCGCGA | mmm00m000m0mmm | oooooooooosso |
| lncFAM69C2 5 | LNC FAM69C2 | ENST00000580048 | 764 | 157 | AACGUUCGACAAGA | mmm0mmm00m00mm | oooooooooosso |
| lncFAM69C2 6 | LNC FAM69C2 | ENST00000580048 | 766 | 158 | CGUUCGACAAGGAA | mmmmm00m00m0mm | oooooooooosso |
| lncFAM69C2 7 | LNC FAM69C2 | ENST00000580048 | 768 | 159 | UUCGACAAGGACUA | mmm00m00m00mmm | oooooooooosso |
| lncFAM69C2 8 | LNC FAM69C2 | ENST00000580048 | 790 | 160 | ACGUUAACGGCACA | mm0m00m00m0m0mm | oooooooooosso |
| lncFAM69C2 9 | LNC FAM69C2 | ENST00000580048 | 795 | 161 | AACGGCACAGCAUA | mmm00m00m00m0mm | oooooooooosso |
| lncFAM69C2 10 | LNC FAM69C2 | ENST00000580048 | 932 | 162 | UGUAGACGAAUAAA | mmm000m000m0mm | oooooooooosso |
| lncFAM69C2 11 | LNC FAM69C2 | ENST00000580048 | 1391 | 163 | UUCCAACGAGUGGA | mmmm00m000m0mm | oooooooooosso |
| lncFAM69C2 12 | LNC FAM69C2 | ENST00000580048 | 1999 | 164 | UUAUAACGACAUUA | mm0m00m00m0mmm | oooooooooosso |
| lncFAM69C2 13 | LNC FAM69C2 | ENST00000580048 | 2001 | 165 | AUAACGACAUUGCA | mm00m00m0mm0mm | oooooooooosso |
| lncFAM69C2 14 | LNC FAM69C2 | ENST00000580048 | 531 | 166 | CGAUUUCGAGAAAA | mm0mmmm000m0mm | oooooooooosso |
| lncFAM69C2 15 | LNC FAM69C2 | ENST00000580048 | 535 | 167 | UUCGAGAAAUGACA | mmm000m00m0mm | oooooooooosso |
| lncFAM69C2 16 | LNC FAM69C2 | ENST00000580048 | 597 | 168 | UCUCGAAUGGCUCA | mmmm000m00mmmm | oooooooooosso |
| lncFAM69C2 17 | LNC FAM69C2 | ENST00000580048 | 876 | 169 | GAACCUCGAGUUAA | mm0mmmm000mmmm | oooooooooosso |
| lncFAM69C2 18 | LNC FAM69C2 | ENST00000580048 | 879 | 170 | CCUCGAGUUAGAGA | mmmm000mm00mm | oooooooooosso |
| lncFAM69C2 19 | LNC FAM69C2 | ENST00000580048 | 1573 | 171 | CUGCGAAGAUGCAA | mm0m000m0m0mmm | oooooooooosso |
| lncFAM69C2 20 | LNC FAM69C2 | ENST00000580048 | 1575 | 172 | GCGAAGAUGCAAAA | mm000m0m0m0mm | oooooooooosso |
| lncFAM69C2 21 | LNC FAM69C2 | ENST00000580048 | 1927 | 173 | UUAUGCUUAGUGGA | mm0m0mmm00m0mm | oooooooooosso |
| lncFAM69C2 22 | LNC FAM69C2 | ENST00000580048 | 2019 | 174 | GCUACACUCCAUGA | mmm0m0mmmm0mmm | oooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncFAM69C2 23 | LNC FAM69C2 | ENST00000 580048 | 2674 | 175 | GUAUCAAGGA CCUA | mm0mm00m00m mmm | ooooooooo oosso |
| lncFAM69C2 24 | LNC FAM69C2 | ENST00000 580048 | 2721 | 176 | AUGCCCUAUU GAAA | mm0mmmm0mm 00mm | ooooooooo oosso |
| lncFAM69C2 25 | LNC FAM69C2 | ENST00000 580048 | 3316 | 177 | AUCCCAACUU GUAA | mmmmm00mmm 0mm | ooooooooo oosso |
| lncFAM69C2 26 | LNC FAM69C2 | ENST00000 580048 | 1749 | 178 | ACUAUCGAAA UAAA | mmm0mm00m0 m0mm | ooooooooo oosso |
| lncFAM69C2 27 | LNC FAM69C2 | ENST00000 580048 | 2532 | 179 | CUUAUACCAG GAGA | mmm0m0mm00 m0mm | ooooooooo oosso |
| lncFAM69C2 28 | LNC FAM69C2 | ENST00000 580048 | 2724 | 180 | CCCUAUUGAA CAUA | mmmm0mm000 m0mm | ooooooooo oosso |
| lncFAM69C2 29 | LNC FAM69C2 | ENST00000 580048 | 2744 | 181 | UAGUAAGAU GGCUA | mm0m00m0m00 mmm | ooooooooo oosso |
| lncFAM69C2 30 | LNC FAM69C2 | ENST00000 580048 | 3321 | 182 | AACUUGUAGC UGCA | mmmmm0m00m m0mm | ooooooooo oosso |
| lncVEZF1 1 | LNC VEZF1 | ENST00000 585065 | 239 | 183 | AUAUCGAGUA CUGA | mm0mm000m0m m0m | ooooooooo oosso |
| lncVEZF1 2 | LNC VEZF1 | ENST00000 585065 | 2307 | 184 | UGUACUCGAG AAAA | mmm0mmm00m 00mm | ooooooooo oosso |
| lncVEZF1 3 | LNC VEZF1 | ENST00000 585065 | 2637 | 185 | UGCGAUUUGU UGGA | mmm00mmm0m m0m | ooooooooo oosso |
| lncVEZF1 4 | LNC VEZF1 | ENST00000 585065 | 2638 | 186 | GCGAUUUGUU GGAA | mm00mmm0mm 00mm | ooooooooo oosso |
| lncVEZF1 5 | LNC VEZF1 | ENST00000 585065 | 2863 | 187 | GCCCUCGACU ACCA | mmmmmm00mm 0mm | ooooooooo oosso |
| lncVEZF1 6 | LNC VEZF1 | ENST00000 585065 | 3477 | 188 | UGACAACGGC AGAA | mm0m00m00m0 0mm | ooooooooo oosso |
| lncVEZF1 7 | LNC VEZF1 | ENST00000 585065 | 3478 | 189 | GACAACGGCA GAGA | mmm00m00m00 0mm | ooooooooo oosso |
| lncVEZF1 8 | LNC VEZF1 | ENST00000 585065 | 3675 | 190 | CGUUUACCUU AGA | mmmmm0mmm m0mm | ooooooooo oosso |
| lncVEZF1 9 | LNC VEZF1 | ENST00000 585065 | 3804 | 191 | CCACUCGAUA ACAA | mm0mmm00m00 mmm | ooooooooo oosso |
| lncVEZF1 10 | LNC VEZF1 | ENST00000 585065 | 3805 | 192 | CACUCGAUAA CACA | mmmmm00m00 m0mm | ooooooooo oosso |
| lncVEZF1 11 | LNC VEZF1 | ENST00000 585065 | 3806 | 193 | ACUCGAUAAC ACCA | mmmm00m00m0 mmm | ooooooooo oosso |
| lncVEZF1 12 | LNC VEZF1 | ENST00000 585065 | 3808 | 194 | UCGAUAACAC CAAA | mm00m0m0mm 0mm | ooooooooo oosso |
| lncVEZF1 13 | LNC VEZF1 | ENST00000 585065 | 4348 | 195 | AAUGCGUCCA UCUA | mmm0m0mmm0 mmmm | ooooooooo oosso |
| lncVEZF1 14 | LNC VEZF1 | ENST00000 585065 | 4349 | 196 | AUGCGUCCAU CUGA | mm0m0mmm0m mmmm | ooooooooo oosso |
| lncVEZF1 15 | LNC VEZF1 | ENST00000 585065 | 4350 | 197 | UGCGUCCAUC UGAA | m0m0mmm0mm m0mm | ooooooooo oosso |
| lncVEZF1 16 | LNC VEZF1 | ENST00000 585065 | 4351 | 198 | GCGUCCAUCU GAAA | mm0mmm0mmm 00mm | ooooooooo oosso |
| lncVEZF1 17 | LNC VEZF1 | ENST00000 585065 | 2309 | 199 | UACUCGAGAA ACUA | mmmmm000m00 mmm | ooooooooo oosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncVEZF1 18 | LNC VEZF1 | ENST00000585065 | 2312 | 200 | UCGAGAAACUUUGA | mm000m00mmmmmm | ooooooooooosso |
| lncVEZF1 19 | LNC VEZF1 | ENST00000585065 | 2449 | 201 | ACCCAUUACCUACA | mmmm0mmm0mmm0mm | ooooooooooosso |
| lncVEZF1 20 | LNC VEZF1 | ENST00000585065 | 2539 | 202 | GGUGCCUAUGAGUA | mmm0mmm0m000mm | ooooooooooosso |
| lncVEZF1 21 | LNC VEZF1 | ENST00000585065 | 2541 | 203 | UGCCUAUGAGUAUA | mmmmm0m000m0mm | ooooooooooosso |
| lncVEZF1 22 | LNC VEZF1 | ENST00000585065 | 3674 | 204 | CCCGUUUACCUUAA | mmm0mmm0mmmmm | ooooooooooosso |
| lncVEZF1 23 | LNC VEZF1 | ENST00000585065 | 3727 | 205 | CUUGGCGAAAGUAA | mmm00m00m00mmm | ooooooooooosso |
| lncVEZF1 24 | LNC VEZF1 | ENST00000585065 | 3730 | 206 | GGCGAAAGUAAAAA | mmm00000m000mm | ooooooooooosso |
| lncVEZF1 25 | LNC VEZF1 | ENST00000585065 | 4441 | 207 | UCUUGGACUAGAGA | mmmm000mm000mm | ooooooooooosso |
| lncVEZF1 26 | LNC VEZF1 | ENST00000585065 | 4444 | 208 | UGGACUAGAGACAA | mm00mm00m00mmm | ooooooooooosso |
| lncVEZF1 27 | LNC VEZF1 | ENST00000585065 | 4650 | 209 | AAGUUCGAUUUUUA | mm0mmm00mmmmmm | ooooooooooosso |
| lncVEZF1 28 | LNC VEZF1 | ENST00000585065 | 2723 | 210 | UGAUAGGUUUAGCA | mm0m000mmm00mm | ooooooooooosso |
| lncVEZF1 29 | LNC VEZF1 | ENST00000585065 | 3116 | 211 | CCUUAGUGUGCUUA | mmmm00m0m0mmmm | ooooooooooosso |
| lncVEZF1 30 | LNC VEZF1 | ENST00000585065 | 3369 | 212 | AGUUGGUCCAUUAA | mmmm00mmm0mmmm | ooooooooooosso |
| lncFBXO 1 | LNC FBXO 256 | ENST00000607352 | 198 | 213 | UUUAUAUGUCGUCA | mmm0m0m0mm0mm | ooooooooooosso |
| lncFBXO 2 | LNC FBXO 256 | ENST00000607352 | 199 | 214 | UUAUAUGUCGUCUA | mm0m0m0m0mmmm | ooooooooooosso |
| lncFBXO 3 | LNC FBXO 256 | ENST00000607352 | 886 | 215 | CUUUGUCGUAAGUA | mmmm0mm0m000mm | ooooooooooosso |
| lncFBXO 4 | LNC FBXO 256 | ENST00000607352 | 887 | 216 | UUUGUCGUAAGUUA | mmm0mm0m000mmm | ooooooooooosso |
| lncFBXO 5 | LNC FBXO 256 | ENST00000607352 | 888 | 217 | UUGUCGUAAGUUAA | mm0mm0m000mmmm | ooooooooooosso |
| lncFBXO 6 | LNC FBXO 256 | ENST00000607352 | 889 | 218 | UGUCGUAAGUUAUA | mmmm0m000mm0mm | ooooooooooosso |
| lncFBXO 7 | LNC FBXO 256 | ENST00000607352 | 890 | 219 | GUCGUAAGUUAUGA | mmm0m000mm0mmm | ooooooooooosso |
| lncFBXO 8 | LNC FBXO 256 | ENST00000607352 | 2596 | 220 | UGAGAGCGUUGUUA | mm00m0m0m0mmm | ooooooooooosso |
| lncFBXO 9 | LNC FBXO 256 | ENST00000607352 | 2598 | 221 | AGAGCGUUGUUUAA | mm00m0mm0mmmmm | ooooooooooosso |
| lncFBXO 10 | LNC FBXO 256 | ENST00000607352 | 2842 | 222 | GUCUUGCGACUGAA | mmmmm0m00mm0mm | ooooooooooosso |
| lncFBXO 11 | LNC FBXO 256 | ENST00000607352 | 2844 | 223 | CUUGCGACUGAUCA | mmm0m00mm00mmm | ooooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncFBXO 12 | LNC FBXO 256 | ENST00000 607352 | 2846 | 224 | UGCGACUGAU CUUA | mmm00mm00m mmmm | oooooooo oosso |
| lncFBXO 13 | LNC FBXO 256 | ENST00000 607352 | 2845 | 225 | UUGCGACUGA UCUA | mm0m00mm00m mmm | oooooooo oosso |
| lncFBXO 14 | LNC FBXO 256 | ENST00000 607352 | 2847 | 226 | GCGACUGAUC UUCA | mm00mm00mm mmmm | oooooooo oosso |
| lncFBXO 15 | LNC FBXO 256 | ENST00000 607352 | 2871 | 227 | CCUAUCCGUU ACUA | mmm0mmm0mm 0mm | oooooooo oosso |
| lncFBXO 16 | LNC FBXO 256 | ENST00000 607352 | 2873 | 228 | UAUCCGUUAC UGAA | mmmmm0mm0m m0mm | oooooooo oosso |
| lncFBXO 17 | LNC FBXO 256 | ENST00000 607352 | 3806 | 229 | ACUCGAUAAC ACCA | mmmm00mm0m0 mmm | oooooooo oosso |
| lncFBXO 18 | LNC FBXO 256 | ENST00000 607352 | 685 | 230 | GGUAGAUCUA GCUA | mmm000mmm00 mmm | oooooooo oosso |
| lncFBXO 19 | LNC FBXO 256 | ENST00000 607352 | 687 | 231 | UAGAUCUAGC UUCA | mm00mmm00m mmmm | oooooooo oosso |
| lncFBXO 20 | LNC FBXO 256 | ENST00000 607352 | 689 | 232 | GAUCUAGCUU CAUA | mmmmm00mm m0mm | oooooooo oosso |
| lncFBXO 21 | LNC FBXO 256 | ENST00000 607352 | 1073 | 233 | AGGUAUCCAA UCCA | mm0m0mmm00 mmmm | oooooooo oosso |
| lncFBXO 22 | LNC FBXO 256 | ENST00000 607352 | 1071 | 234 | UAAGGUAUCC AAUA | mm000m0mmm0 0mm | oooooooo oosso |
| lncFBXO 23 | LNC FBXO 256 | ENST00000 607352 | 2071 | 235 | GACUAGCAUA GGUA | mmmm00m0m00 0mm | oooooooo oosso |
| lncFBXO 24 | LNC FBXO 256 | ENST00000 607352 | 2074 | 236 | UAGCAUAGGU CUGA | mm0m0m000mm mmm | oooooooo oosso |
| lncFBXO 25 | LNC FBXO 256 | ENST00000 607352 | 2076 | 237 | GCAUAGGUCU GUUA | mm0m000mmm0 mmm | oooooooo oosso |
| lncFBXO 26 | LNC FBXO 256 | ENST00000 607352 | 2600 | 238 | AGCGUUGUUU AAUA | mmm0mm0mmm 00mm | oooooooo oosso |
| lncFBXO 27 | LNC FBXO 256 | ENST00000 607352 | 2870 | 239 | UCCUAUCCGU UACA | mmmm0mm0m m0mm | oooooooo oosso |
| lncFBXO 28 | LNC FBXO 256 | ENST00000 607352 | 2874 | 240 | AUCCGUUACU GAAA | mmmm0mm0mm 00mm | oooooooo oosso |
| lncFBXO 29 | LNC FBXO 256 | ENST00000 607352 | 2876 | 241 | CCGUUACUGA AAGA | mm0mm0mm000 0mm | oooooooo oosso |
| lncFBXO 30 | LNC FBXO 256 | ENST00000 607352 | 200 | 242 | UAUAUGUCGU CUUA | mmm0m0mm0m mmmm | oooooooo oosso |
| lncNDST3 1 | LNC NDST3 | ENST00000 602414 | 77 | 243 | AAAGUACGUA GUUA | mm00m0m0m00 mmm | oooooooo osso |
| lncNDST3 2 | LNC NDST3 | ENST00000 602414 | 78 | 244 | AAGUACGUAG UUGA | mm0m0m0m00m mmm | oooooooo osso |
| lncNDST3 3 | LNC NDST3 | ENST00000 602414 | 79 | 245 | AGUACGUAGU UGUA | mmm0m00m0m m0mm | oooooooo osso |
| lncNDST3 4 | LNC NDST3 | ENST00000 602414 | 81 | 246 | UACGUAGUUG UCUA | mmm0m00mm0 mmmm | oooooooo osso |
| lncNDST3 5 | LNC NDST3 | ENST00000 602414 | 440 | 247 | ACAUUACGAU GGAA | mm0mm0m00m0 0mm | oooooooo osso |
| lncNDST3 6 | LNC NDST3 | ENST00000 602414 | 441 | 248 | CAUUACGAUG GAUA | mmmm0m00m00 0mm | oooooooo osso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncNDST3 7 | LNC NDST3 | ENST00000 602414 | 442 | 249 | AUUACGAUGG AUGA | mmm0m00m000 mmm | ooooooooo osso |
| lncNDST3 8 | LNC NDST3 | ENST00000 602414 | 443 | 250 | UUACGAUGGA UGAA | mm0m00m000m 0mm | ooooooooo osso |
| lncNDST3 9 | LNC NDST3 | ENST00000 602414 | 444 | 251 | UACGAUGGAU GAUA | mmm0m000m0 0mm | ooooooooo osso |
| lncNDST3 10 | LNC NDST3 | ENST00000 602414 | 445 | 252 | ACGAUGGAUG AUGA | mm00m000m00 mmm | ooooooooo osso |
| lncNDST3 11 | LNC NDST3 | ENST00000 602414 | 508 | 253 | AGCAUCCGGC AAUA | mmm0mmm00m 00mm | ooooooooo osso |
| lncNDST3 12 | LNC NDST3 | ENST00000 602414 | 523 | 254 | ACUUAUCGUA GUUA | mmmm0mm0 0mmm | ooooooooo osso |
| lncNDST3 13 | LNC NDST3 | ENST00000 602414 | 524 | 255 | CUUAUCGUAG UUGA | mmm0mm0m00 mmmm | ooooooooo osso |
| lncNDST3 14 | LNC NDST3 | ENST00000 602414 | 625 | 256 | GUGGUCCGUG AUAA | mm00mmm0m00 mmm | ooooooooo osso |
| lncNDST3 15 | LNC NDST3 | ENST00000 602414 | 626 | 257 | UGGUCCGUGA UAAA | mm0mmm0m00 m0mm | ooooooooo osso |
| lncNDST3 16 | LNC NDST3 | ENST00000 602414 | 627 | 258 | GGUCCGUGAU AAUA | mmmmm0m00m 00mm | ooooooooo osso |
| lncNDST3 17 | LNC NDST3 | ENST00000 602414 | 628 | 259 | GUCCGUGAUA AUUA | mmmm0m00m00 mmm | ooooooooo osso |
| lncNDST3 18 | LNC NDST3 | ENST00000 602414 | 629 | 260 | UCCGUGAUAA UUAA | mmm0m00m0m mmm | ooooooooo osso |
| lncNDST3 19 | LNC NDST3 | ENST00000 602414 | 91 | 261 | UCUUUCGUAA GUUA | mmmmm0m00 0mmm | ooooooooo osso |
| lncNDST3 20 | LNC NDST3 | ENST00000 602414 | 92 | 262 | CUUUCGUAAG UUAA | mmmm00m00m mmm | ooooooooo osso |
| lncNDST3 21 | LNC NDST3 | ENST00000 602414 | 515 | 263 | GGCAAUGGAC UUAA | mmm0m0m000mm mmm | ooooooooo osso |
| lncNDST3 22 | LNC NDST3 | ENST00000 602414 | 550 | 264 | UCCGAAUAAU AUCA | mmm000m00m0 mmm | ooooooooo osso |
| lncNDST3 23 | LNC NDST3 | ENST00000 602414 | 551 | 265 | CCGAAUAAUA UCCA | mm000m00m0m mmm | ooooooooo osso |
| lncNDST3 24 | LNC NDST3 | ENST00000 602414 | 623 | 266 | AGGUGGUCCG UGAA | mm0m00mmm0 m0mm | ooooooooo osso |
| lncNDST3 25 | LNC NDST3 | ENST00000 602414 | 624 | 267 | GGUGGUCCGU GAUA | mmm00mmm0m 00mm | ooooooooo osso |
| lncNDST3 26 | LNC NDST3 | ENST00000 602414 | 630 | 268 | CCGUGAUAAU UAAA | mm0m00m00mm 0mm | ooooooooo osso |
| lncNDST3 27 | LNC NDST3 | ENST00000 602414 | 130 | 269 | UGCCUUACCU AAAA | mmmmmm0mm m00mm | ooooooooo osso |
| lncNDST3 28 | LNC NDST3 | ENST00000 602414 | 131 | 270 | GCCUUACCUA AAAA | mmmmm0mmm0 00mm | ooooooooo osso |
| lncNDST3 29 | LNC NDST3 | ENST00000 602414 | 516 | 271 | GCAAUGGACU AUA | mm00m000mmm 0mm | ooooooooo osso |
| lncNDST3 30 | LNC NDST3 | ENST00000 602414 | 519 | 272 | AUGGACUUAU CGUA | mm000mmm0m m0mm | ooooooooo osso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncMALAT1 1 | LNC Malat1 | MALAT1 | 445 | 273 | UUCGCUUAGUUGGA | mmm0mmm00mm0mm | ooooooooooosso |
| lncMALAT1 2 | LNC Malat1 | MALAT1 | 860 | 274 | GUUGCGUAAUGGAA | mmm0m0m00m00mm | ooooooooooosso |
| lncMALAT1 3 | LNC Malat1 | MALAT1 | 1006 | 275 | AUGACCCGUUUAAA | mm00mmm0mmm0mm | ooooooooooosso |
| lncMALAT1 4 | LNC Malat1 | MALAT1 | 1007 | 276 | UGACCCGUUUAAAA | mm0mmm0mmm00mm | ooooooooooosso |
| lncMALAT1 5 | LNC Malat1 | MALAT1 | 1818 | 277 | UAAACGCAGACGAA | mm00m0m000m0mm | ooooooooooosso |
| lncMALAT1 6 | LNC Malat1 | MALAT1 | 1821 | 278 | ACGCAGACGAAAAA | mm0m000m000m0mm | ooooooooooosso |
| lncMALAT1 7 | LNC Malat1 | MALAT1 | 2513 | 279 | UUCGUAACGGAAGA | mmm0m0m00m00mm | ooooooooooosso |
| lncMALAT1 8 | LNC Malat1 | MALAT1 | 2813 | 280 | AGCGCUAACGAUUA | mmm0mm0mm00mmm | ooooooooooosso |
| lncMALAT1 9 | LNC Malat1 | MALAT1 | 3087 | 281 | UCGUACUGAGGUGA | mm0m0mm00m0mmm | ooooooooooosso |
| lncMALAT1 10 | LNC Malat1 | MALAT1 | 7883 | 282 | UAAUCGGUUUCAAA | mm0mm00mmm0mm | ooooooooooosso |
| lncMALAT1 11 | LNC Malat1 | MALAT1 | 8585 | 283 | ACGAGAACCUAAUA | mm000m0mmm00mm | ooooooooooosso |
| lncMALAT1 12 | LNC Malat1 | MALAT1 | 1218 | 284 | CGAAUUCCGGUGAA | mm00mmmm00m0mm | ooooooooooosso |
| lncMALAT1 13 | LNC Malat1 | MALAT1 | 1251 | 285 | UAAAUACGCCUCGA | mm00m0m0mmmmmm | ooooooooooosso |
| lncMALAT1 14 | LNC Malat1 | MALAT1 | 3014 | 286 | UCGGCAAUAUGUUA | mm00m0m0m0mmmm | ooooooooooosso |
| lncMALAT1 15 | LNC Malat1 | MALAT1 | 5094 | 287 | UUACGGAAUCUACA | mm0m00m0mm0mm | ooooooooooosso |
| lncMALAT1 16 | LNC Malat1 | MALAT1 | 5338 | 288 | UCGUUUGCCUCAGA | mm0mmm0mmm0mm | ooooooooooosso |
| lncMALAT1 17 | LNC Malat1 | MALAT1 | 5970 | 289 | GUCUGCGAACACUA | mmmm0m000m0mmm | ooooooooooosso |
| lncMALAT1 18 | LNC Malat1 | MALAT1 | 6008 | 290 | AGCGGAAGAACGAA | mmm000m00mm0mm | ooooooooooosso |
| lncMALAT1 19 | LNC Malat1 | MALAT1 | 6634 | 291 | AUCCCGCUGCUAUA | mmmmm0m0m0mm | ooooooooooosso |
| lncMALAT1 20 | LNC Malat1 | MALAT1 | 6662 | 292 | AACGACUGGAGUAA | mmm00mm00m0mmm | ooooooooooosso |
| lncMALAT1 21 | LNC Malat1 | MALAT1 | 6782 | 293 | GUCGUAUUUGUGAA | mmm0m0mmm0m0mm | ooooooooooosso |
| lncMALAT1 22 | LNC Malat1 | MALAT1 | 7439 | 294 | ACCGAAGGCUUAAA | mmm000mm0m0mm | ooooooooooosso |
| lncMALAT1 23 | LNC Malat1 | MALAT1 | 7681 | 295 | UCAAGCGGUGCUUA | mm000m00m0mmmm | ooooooooooosso |
| lncMALAT1 24 | LNC Malat1 | MALAT1 | 8219 | 296 | UAGCGGAAGCUGAA | mm0m00m0mm0mm | ooooooooooosso |
| lncMALAT1 25 | LNC Malat1 | MALAT1 | 4012 | 297 | UGAGUAGGCCAAAA | mm00m000mm00mm | ooooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncMALAT1 26 | LNC Malat1 | MALAT1 | 2325 | 298 | ACGUAGACCA GAAA | mm0m000mm000mm | oooooooooosso |
| lncMALAT1 27 | LNC Malat1 | MALAT1 | 2742 | 299 | UUCGUGGUGA AGAA | mmm0m00m0000mm | oooooooooosso |
| lncMALAT1 28 | LNC Malat1 | MALAT1 | 1423 | 300 | CUUAGCGUUA AGUA | mmm00m0mm000mm | oooooooooosso |
| lncMALAT1 29 | LNC Malat1 | MALAT1 | 1610 | 301 | CCCGAAUUAA UACA | mmm000mm00m0mm | oooooooooosso |
| lncMALAT1 30 | LNC Malat1 | MALAT1 | 810 | 302 | AAGUCCGCCA UUUA | mm0mmm0mm0mmmm | oooooooooosso |
| lncFAM22E1 1 | LNC FAM22E1 | ENST00000 605920 | 509 | 303 | UAGAGGUAU UCCCA | mm00m0m0mm mmmm | oooooooooosso |
| lncFAM22E1 2 | LNC FAM22E1 | ENST00000 605920 | 716 | 304 | CCGUGCGCUU UAUA | mm0m0m0mm m0mm | oooooooooosso |
| lncFAM22E1 3 | LNC FAM22E1 | ENST00000 605920 | 1139 | 305 | CCAGCCUUAA AUCA | mm00mmmm000 mmm | oooooooooosso |
| lncFAM22E1 4 | LNC FAM22E1 | ENST00000 605920 | 1148 | 306 | AAUCGAGCCG ACUA | mmmm000mm00 mmm | oooooooooosso |
| lncFAM22E1 5 | LNC FAM22E1 | ENST00000 605920 | 1149 | 307 | AUCGAGCCGA CUAA | mmm000mm00m mmm | oooooooooosso |
| lncFAM22E1 6 | LNC FAM22E1 | ENST00000 605920 | 1150 | 30 | UCGAGCCGAC UACA | mm000mm00mm 0mm | oooooooooosso |
| lncFAM22E1 7 | LNC FAM22E1 | ENST00000 605920 | 1328 | 309 | GCUUCAGCGG AAUA | mmmmm00m00 m0mm | oooooooooosso |
| lncFAM22E1 8 | LNC FAM22E1 | ENST00000 605920 | 1334 | 310 | GCGGAAUACC UACA | mm00m0m0mm m0mm | oooooooooosso |
| lncFAM22E1 9 | LNC FAM22E1 | ENST00000 605920 | 1335 | 311 | CGGAAUACCU ACUA | mm000m0mm0 mmm | oooooooooosso |
| lncFAM22E1 10 | LNC FAM22E1 | ENST00000 605920 | 1362 | 312 | AACAAGCCGA UUGA | mmm000mm00m mmm | oooooooooosso |
| lncFAM22E1 11 | LNC FAM22E1 | ENST00000 605920 | 1363 | 313 | ACAAGCCGAU UGAA | mm000mm00mm 0mm | oooooooooosso |
| lncFAM22E1 12 | LNC FAM22E1 | ENST00000 605920 | 1364 | 314 | CAAGCCGAUU GAUA | mm00mm00mm0 0mm | oooooooooosso |
| lncFAM22E1 13 | LNC FAM22E1 | ENST00000 605920 | 1365 | 315 | AAGCCGAUUG AUCA | mm0mm00mm00 mmm | oooooooooosso |
| lncFAM22E1 14 | LNC FAM22E1 | ENST00000 605920 | 1366 | 316 | AGCCGAUUGA UCAA | mmmm00mm00 mmmm | oooooooooosso |
| lncFAM22E1 15 | LNC FAM22E1 | ENST00000 605920 | 1367 | 317 | GCCGAUUGAU CACA | mmm00mm00m m0mm | oooooooooosso |
| lncFAM22E1 16 | LNC FAM22E1 | ENST00000 605920 | 1368 | 318 | CCGAUUGAUC ACAA | mm00mm00mm0 mmm | oooooooooosso |
| lncFAM22E1 17 | LNC FAM22E1 | ENST00000 605920 | 1369 | 319 | CGAUUGAUCA CAUA | mm0mm00mm0 m0mm | oooooooooosso |
| lncFAM22E1 18 | LNC FAM22E1 | ENST00000 605920 | 1562 | 320 | UACCCUUAUG GCUA | mmmmmmm0m 0mm | oooooooooosso |
| lncFAM22E1 19 | LNC FAM22E1 | ENST00000 605920 | 1563 | 321 | ACCCUUAUGG CUAA | mmmmmm0m00 mmmm | oooooooooosso |

TABLE 1-continued

Sense Strand Oligonucleotides

| Oligo ID | Gene Name | Accession number | Start Site | SEQ ID NO: | Sense sequence | Sense Chemistry | Sense Backbone |
|---|---|---|---|---|---|---|---|
| lncFAM22E1 20 | LNC FAM22E1 | ENST00000 605920 | 1564 | 322 | CCCUUAUGGC UAAA | mmmmm0m00m m0mm | oooooooo oosso |
| lncFAM22E1 21 | LNC FAM22E1 | ENST00000 605920 | 1140 | 323 | CAGCCUUAAA UCGA | mm0mmmm000 mmmm | oooooooo oosso |
| lncFAM22E1 22 | LNC FAM22E1 | ENST00000 605920 | 1565 | 324 | CCUUAUGGCU AAAA | mmmm0m00mm 00mm | oooooooo oosso |
| lncFAM22E1 23 | LNC FAM22E1 | ENST00000 605920 | 507 | 325 | ACUAGAGGUA UUCA | mmm000m0m0m mmm | oooooooo oosso |
| lncFAM22E1 24 | LNC FAM22E1 | ENST00000 605920 | 508 | 326 | CUAGAGGUAU UCCA | mm00m0m0mm mmm | oooooooo oosso |
| lncFAM22E1 25 | LNC FAM22E1 | ENST00000 605920 | 1141 | 327 | AGCCUUAAAU CGAA | mmmmmm000m m0mm | oooooooo oosso |
| lncFAM22E1 26 | LNC FAM22E1 | ENST00000 605920 | 1142 | 328 | GCCUUAAAUC GAGA | mmmmm00mm 00mm | oooooooo oosso |
| lncFAM22E1 27 | LNC FAM22E1 | ENST00000 605920 | 1370 | 329 | GAUUGAUCAC AUUA | mmmm00mm0m 0mmm | oooooooo oosso |
| lncFAM22E1 28 | LNC FAM22E1 | ENST00000 605920 | 1389 | 330 | CUCUAGCAGU GCAA | mmmm00m00m0 mmm | oooooooo oosso |
| lncFAM22E1 29 | LNC FAM22E1 | ENST00000 605920 | 1390 | 331 | UCUAGCAGUG CAAA | mmm00m00m0m 0mm | oooooooo oosso |
| lncFAM22E1 30 | LNC FAM22E1 | ENST00000 605920 | 1492 | 332 | UCUUAUGACA GCAA | mmmm0m00m00 mmm | oooooooo oosso |

FIG. 1 Legend:
o: phosphodiester
s: phosphorothioate
P: 5' phosphorylation
0: 2'-OH
f: 2'-fluoro
m: 2' O-methyl

TABLE 2

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncRala1 1 | LNC Rala1 | ENST00000 340510 | 140 | 333 | UGAUUCUGAAG CGGAACCU | Pm00ffff00m0f 00m0ff0 | oooooooo ooosssssso |
| lncRala1 2 | LNC Rala1 | ENST00000 340510 | 296 | 334 | UAGGCUCGGGA UCAUGUAA | Pm000fff0m00 ff0f0f00 | oooooooo ooosssssso |
| lncRala1 3 | LNC Rala1 | ENST00000 340510 | 366 | 335 | UUACAGCGGAA AAAGGCAG | Pmf0f00f00m0 0m000f00 | oooooooo ooosssssso |
| lncRala1 4 | LNC Rala1 | ENST00000 340510 | 367 | 336 | UUUACAGCGGA AAAGGCA | Pmff0f00f000 m000m0f0 | oooooooo ooosssssso |
| lncRala1 5 | LNC Rala1 | ENST00000 340510 | 368 | 337 | UUUUACAGCGG AAAAGGC | Pmfff0f00f000 m00m000 | oooooooo ooosssssso |
| lncRala1 6 | LNC Rala1 | ENST00000 340510 | 369 | 338 | UAUUUACAGCG GAAAAGG | Pm0fff0f00f00 m00m0m0 | oooooooo ooosssssso |
| lncRala1 7 | LNC Rala1 | ENST00000 340510 | 370 | 339 | UUAUUUACAGC GGAAAAG | Pmf0fff0f00f00 0m0m00 | oooooooo ooosssssso |
| lncRala1 8 | LNC Rala1 | ENST00000 340510 | 487 | 340 | UAAUUCCGCUU GGCAAGAA | Pm00ffff0fff00 f00m00 | oooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncRala1 9 | LNC Rala1 | ENST00000340510 | 488 | 341 | UAAAUUCCGCUUGGCAAGA | Pm000ffff0fff0 0f0000 | ooooooooo ooossssso |
| lncRala1 10 | LNC Rala1 | ENST00000340510 | 489 | 342 | UUAAAUUCCGCUUGGCAAG | Pmf000ffff0fff 00f000 | ooooooooo ooossssso |
| lncRala1 11 | LNC Rala1 | ENST00000340510 | 490 | 343 | UUUAAAUUCCGCUUGGCAA | Pmff000ffff0ff 00f00 | ooooooooo ooossssso |
| lncRala1 12 | LNC Rala1 | ENST00000340510 | 491 | 344 | UUUUAAAUUCCGCUUGGCA | Pmfff000ffff0ff f00f0 | ooooooooo ooossssso |
| lncRala1 13 | LNC Rala1 | ENST00000340510 | 492 | 345 | UAUUUAAAUUCCGCUUGGC | Pm0fff000ffff0 fff000 | ooooooooo ooossssso |
| lncRala1 14 | LNC Rala1 | ENST00000340510 | 620 | 346 | UUCUCUGCGGCUCAAAUGU | Pmfffff0f00fff0 00f00 | ooooooooo ooossssso |
| lncRala1 15 | LNC Rala1 | ENST00000340510 | 622 | 347 | UGAUCUCUGCGGCUCAAAU | Pm00fffff0f00f ff00m0 | ooooooooo ooossssso |
| lncRala1 16 | LNC Rala1 | ENST00000340510 | 852 | 348 | UGACUGACGUGGUAGGAUU | Pm00ff00f0f00 f00m0f0 | ooooooooo ooossssso |
| lncRala1 17 | LNC Rala1 | ENST00000340510 | 853 | 349 | UAGACUGACGUGGUAGGAU | Pm000ff00f0f0 0f00m00 | ooooooooo ooossssso |
| lncRala1 18 | LNC Rala1 | ENST00000340510 | 1662 | 350 | UGUGUUAAGCUCGUUUUCC | Pm0f0ff000fff0 fffff0 | ooooooooo ooossssso |
| lncRala1 19 | LNC Rala1 | ENST00000340510 | 1663 | 351 | UCGUGUUAAGCUCGUUUUC | Pmf0f0ff000fff 0fff f0 | ooooooooo ooossssso |
| lncRala1 20 | LNC Rala1 | ENST00000340510 | 1664 | 352 | UGCGUGUUAAGCUCGUUUU | Pm0f0f0ff000ff f0fff0 | ooooooooo ooossssso |
| lncRala1 21 | LNC Rala1 | ENST00000340510 | 1205 | 353 | UUGCAUUCGAAAGGAUCCA | Pmf0f0fff0m00 m00fff0 | ooooooooo ooossssso |
| lncRala1 22 | LNC Rala1 | ENST00000340510 | 1208 | 354 | UAAGUGCAUUCGAAAGGAU | Pm000f0f0fff0 00m00m0 | ooooooooo ooossssso |
| lncRala1 23 | LNC Rala1 | ENST00000340510 | 1926 | 355 | UGACGUCGACUUGAGAAAG | Pm00f0ff00fff0 00m0m0 | ooooooooo ooossssso |
| lncRala1 24 | LNC Rala1 | ENST00000340510 | 2933 | 356 | UAAGUUCGGGGCCUACAAA | Pm000fff0000f ff0f000 | ooooooooo ooossssso |
| lncRala1 25 | LNC Rala1 | ENST00000340510 | 1857 | 357 | UAUUGUAACGAUGGAGCUG | Pm0ff0f00f00f 0000ff0 | ooooooooo ooossssso |
| lncRala1 26 | LNC Rala1 | ENST00000340510 | 1203 | 358 | UCAUUCGAAAGGAUCCAUC | Pmf0ff000m0 00fff0f0 | ooooooooo ooossssso |
| lncRala1 27 | LNC Rala1 | ENST00000340510 | 1784 | 359 | UUAGGGUAUGGGCCUAAAU | Pmf00m0f0f00 0fff0000 | ooooooooo ooossssso |
| lncRala1 28 | LNC Rala1 | ENST00000340510 | 99 | 360 | UUUCAGGGUCUAUAUAAGA | Pmfff0000fff0f 0f00m0 | ooooooooo ooossssso |
| lncRala1 29 | LNC Rala1 | ENST00000340510 | 1480 | 361 | UUGUGAUAGCACUACUACA | Pmf0f00f00f0ff 0ff0f0 | ooooooooo ooossssso |
| lncRala1 30 | LNC Rala1 | ENST00000340510 | 1154 | 362 | UUGCAGUGGUCAACUUGUA | Pmf0f00f00ff0 0fff0f0 | ooooooooo ooossssso |
| lncZBTB42 1 | LNC ZBTB42 | ENST00000555578 | 588 | 363 | UAGAUUCGGGCAGAGAUUG | Pm000fff000f0 m000ff0 | ooooooooo ooossssso |
| lncZBTB42 2 | LNC ZBTB42 | ENST00000555578 | 590 | 364 | UGAAGAUUCGGGCAGAGAU | Pm00m00fff00 0f000m00 | ooooooooo ooossssso |
| lncZBTB42 3 | LNC ZBTB42 | ENST00000555578 | 593 | 365 | UUGUGAAGAUUCGGGCAGA | Pmf0f0m000fff 000f000 | ooooooooo ooossssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncZBTB42 4 | LNC ZBTB42 | ENST00000 555578 | 801 | 366 | UUACGGGUCGA AUUGUGUC | Pmf0f000ff000 ff0f0f0 | oooooooo ooosssssso |
| lncZBTB42 5 | LNC ZBTB42 | ENST00000 555578 | 804 | 367 | UUGUUACGGGU CGAAUUGU | Pmf0ff0f000ff0 00ff00 | oooooooo ooosssssso |
| lncZBTB42 6 | LNC ZBTB42 | ENST00000 555578 | 807 | 368 | UAGCUGUUACG GGUCGAAU | Pm00ff0ff0f00 0ff0000 | oooooooo ooosssssso |
| lncZBTB42 7 | LNC ZBTB42 | ENST00000 555578 | 836 | 369 | UGAAGCACAUC GGAUGUGU | Pmm000f0f0ff 000f0f00 | oooooooo ooosssssso |
| lncZBTB42 8 | LNC ZBTB42 | ENST00000 555578 | 960 | 370 | UAAUAAAGGUC CGUGGAAA | Pm00f000m0ff f0f000m0 | oooooooo ooosssssso |
| lncZBTB42 9 | LNC ZBTB42 | ENST00000 555578 | 1073 | 371 | UAUCUCUUCGG AGAGAUCC | Pm0ffffffff000 m000ff0 | oooooooo ooosssssso |
| lncZBTB42 10 | LNC ZBTB42 | ENST00000 555578 | 1075 | 372 | UGAAUCUCUUC GGAGAGAU | Pm000fffffff00 000m00 | oooooooo ooosssssso |
| lncZBTB42 11 | LNC ZBTB42 | ENST00000 555578 | 1076 | 373 | UGGAAUCUCUU CGGAGAGA | Pmm000ffffffff 0000m00 | oooooooo ooosssssso |
| lncZBTB42 12 | LNC ZBTB42 | ENST00000 555578 | 1281 | 374 | UCAGCUAAUCG GCUAUGGA | Pmf00ff00ff00f f0f000 | oooooooo ooosssssso |
| lncZBTB42 13 | LNC ZBTB42 | ENST00000 555578 | 1581 | 375 | UGUGUGGCGAU AAGCUUGU | Pm0f0f00f00f0 00fff00 | oooooooo ooosssssso |
| lncZBTB42 14 | LNC ZBTB42 | ENST00000 555578 | 2212 | 376 | UUUUCAAACGU CCAGCAGC | Pmffff000f0fff 00f000 | oooooooo ooosssssso |
| lncZBTB42 15 | LNC ZBTB42 | ENST00000 555578 | 2213 | 377 | UUUUUCAAACG UCCAGCAG | Pmfffff000f0fff 00f00 | oooooooo ooosssssso |
| lncZBTB42 16 | LNC ZBTB42 | ENST00000 555578 | 2137 | 378 | UUUGAUUAGGC CUAACUCA | Pmff00ff000fff 00fff0 | oooooooo ooosssssso |
| lncZBTB42 17 | LNC ZBTB42 | ENST00000 555578 | 2141 | 379 | UUACGUUGAUU AGGCCUAA | Pmf0f0ff00ff00 0fff00 | oooooooo ooosssssso |
| lncZBTB42 18 | LNC ZBTB42 | ENST00000 555578 | 636 | 380 | UAUAAAGACGG GAAAUUUG | Pm0f00m00f00 0m00fff0 | oooooooo ooosssssso |
| lncZBTB42 19 | LNC ZBTB42 | ENST00000 555578 | 1574 | 381 | UGAUAAGCUUG UGUCCAUC | Pm00f000fff0f 0fff0f0 | oooooooo ooosssssso |
| lncZBTB42 20 | LNC ZBTB42 | ENST00000 555578 | 1575 | 382 | UCGAUAAGCUU GUGUCCAU | Pmf00f000fff0f 0fff00 | oooooooo ooosssssso |
| lncZBTB42 21 | LNC ZBTB42 | ENST00000 555578 | 694 | 383 | UAAGUUAGGGU GAGUCAUC | Pm000ff00m0f 000ff0f0 | oooooooo ooosssssso |
| lncZBTB42 22 | LNC ZBTB42 | ENST00000 555578 | 699 | 384 | UCCAUCAAGUU AGGGUGAG | Pmff0ff000ff0 m00f000 | oooooooo ooosssssso |
| lncZBTB42 23 | LNC ZBTB42 | ENST00000 555578 | 2145 | 385 | UGAUUUACGUU GAUUAGGC | Pm00fff0f0ff00 ff0000 | oooooooo ooosssssso |
| lncZBTB42 24 | LNC ZBTB42 | ENST00000 555578 | 2149 | 386 | UGACAGAUUUA CGUUGAUU | Pm00f000fff0f 0ff00f0 | oooooooo ooosssssso |
| lncZBTB42 25 | LNC ZBTB42 | ENST00000 555578 | 700 | 387 | UUCCAUCAAGU UAGGGUGA | Pmfff0ff000ff0 00mf00 | oooooooo ooosssssso |
| lncZBTB42 26 | LNC ZBTB42 | ENST00000 555578 | 2134 | 388 | UAUUAGGCCUA ACUCACAG | Pm0ff000fff00f ff0f00 | oooooooo ooosssssso |
| lncZBTB42 27 | LNC ZBTB42 | ENST00000 555578 | 1307 | 389 | UGCAGUCCUUA CACAGAGU | Pm0f00fffff0f0 f000m0 | oooooooo ooosssssso |
| lncZBTB42 28 | LNC ZBTB42 | ENST00000 555578 | 640 | 390 | UCCUUAUAAAG ACGGGAAA | Pmffff0f0m000 f000m00 | oooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncZBTB42 29 | LNC ZBTB42 | ENST00000555578 | 1616 | 391 | UCUUGUAAUCCAGGGCCUU | Pmfff0f00fff0m00fff0 | ooooooooooosssssso |
| lncZBTB42 30 | LNC ZBTB42 | ENST00000555578 | 2133 | 392 | UUUAGGCCUAACUCACAGG | Pmff000fff00fff0f000 | ooooooooooosssssso |
| lncPANK1 1 | LNC PANK1 | ENST00000455699 | 174 | 393 | UGUUGAGCUCCAAUGCUGA | Pm0ff000ffff00f0ff00 | ooooooooooosssssso |
| lncPANK1 2 | LNC PANK1 | ENST00000455699 | 176 | 394 | UUAGUUGAGCUCCAAUGCU | Pmf00ff000ffff00f0f0 | ooooooooooosssssso |
| lncPANK1 3 | LNC PANK1 | ENST00000455699 | 179 | 395 | UCGGUAGUUGAGCUCCAAU | Pmf00f00ff000ffff000 | ooooooooooosssssso |
| lncPANK1 4 | LNC PANK1 | ENST00000455699 | 188 | 396 | UUGACACAGUCGGUAGUUG | Pmf00f0f00ff00f00ff0 | ooooooooooosssssso |
| lncPANK1 5 | LNC PANK1 | ENST00000455699 | 191 | 397 | UGAUUGACACAGUCGGUAG | Pm00ff00f0f00ff00f00 | ooooooooooosssssso |
| lncPANK1 6 | LNC PANK1 | ENST00000455699 | 211 | 398 | UGGAACCUGAUACUCUUAU | Pmm000fff00f0fffff00 | ooooooooooosssssso |
| lncPANK1 7 | LNC PANK1 | ENST00000455699 | 419 | 399 | UAAGACUAUAGACCUGCAU | Pmm000ff0f000fff0f00 | ooooooooooosssssso |
| lncPANK1 8 | LNC PANK1 | ENST00000455699 | 565 | 400 | UUUACGGAUACAAGUGCUG | Pmff0f000f0f000f0ff0 | ooooooooooosssssso |
| lncPANK1 9 | LNC PANK1 | ENST00000455699 | 568 | 401 | UGACUUACGGAUACAAGUG | Pm00fff0f000f0f000f0 | ooooooooooosssssso |
| lncPANK1 10 | LNC PANK1 | ENST00000455699 | 571 | 402 | UUGUGACUUACGGAUACAA | Pmf0f00fff0f000f0f00 | ooooooooooosssssso |
| lncPANK1 11 | LNC PANK1 | ENST00000455699 | 573 | 403 | UUGUGUGACUUACGGAUAC | Pmf0f0f00fff0f000f00 | ooooooooooosssssso |
| lncPANK1 12 | LNC PANK1 | ENST00000455699 | 636 | 404 | UCUUUUCGACAUUUUCCAU | Pmffffff00f0ffffff00 | ooooooooooosssssso |
| lncPANK1 13 | LNC PANK1 | ENST00000455699 | 415 | 405 | UCUAUAGACCUGCAUUAAA | Pmff0f000fff0f0ff000 | ooooooooooosssssso |
| lncPANK1 14 | LNC PANK1 | ENST00000455699 | 418 | 406 | UAGACUAUAGACCUGCAUU | Pm000ff0f000fff0f0f0 | ooooooooooosssssso |
| lncPANK1 15 | LNC PANK1 | ENST00000455699 | 505 | 407 | UGGCAUAUAAUCCUGGUGC | Pm00f0f0f00ffff00f00 | ooooooooooosssssso |
| lncPANK1 16 | LNC PANK1 | ENST00000455699 | 259 | 408 | UUCUGGUAUUGUCUGCCAA | Pmfff00f0ff0fff0ff00 | ooooooooooosssssso |
| lncPANK1 17 | LNC PANK1 | ENST00000455699 | 421 | 409 | UUAAAGACUAUAGACCUGC | Pmf00m00ff0f000fff00 | ooooooooooosssssso |
| lncPANK1 18 | LNC PANK1 | ENST00000455699 | 502 | 410 | UAUAUAAUCCUGGUGCCAA | Pm0f0f00ffff00f0ff00 | ooooooooooosssssso |
| lncPANK1 19 | LNC PANK1 | ENST00000455699 | 341 | 411 | UUGCAGCUAUUACUUGUCU | Pmf0f00ff0ff0fff0ff0 | ooooooooooosssssso |
| lncPANK1 20 | LNC PANK1 | ENST00000455699 | 351 | 412 | UCUCAAGGUUAUGCAGCUA | Pmff00m0ff0f0f00ff0 | ooooooooooosssssso |
| lncPANK1 21 | LNC PANK1 | ENST00000455699 | 257 | 413 | UUGGUAUUGUCUGCCAAGA | Pmf00f0ff0fff0ff0000 | ooooooooooosssssso |
| lncPANK1 22 | LNC PANK1 | ENST00000455699 | 367 | 414 | UCUCAGUCAGUAUCUUGCU | Pmfff00ff00f0ffff0f0 | ooooooooooosssssso |
| lncPANK1 23 | LNC PANK1 | ENST00000455699 | 55 | 415 | UGACAUAAGACUCAAUCCU | Pm00f0f0m00fff00fff0 | ooooooooooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncPANK1 24 | LNC PANK1 | ENST00000 455699 | 424 | 416 | UGAGUAAAGAC UAUAGACC | Pm000f00m00f f0f000f0 | ooooooooo ooosssssso |
| lncPANK1 25 | LNC PANK1 | ENST00000 455699 | 253 | 417 | UAUUGUCUGCC AAGAUGAU | Pm0ff0fff0ff00 00f000 | ooooooooo ooosssssso |
| lncPANK1 26 | LNC PANK1 | ENST00000 455699 | 217 | 418 | UAGCACAGGAA CCUGAUAC | Pm00f0f00m00 fff00f00 | ooooooooo ooosssssso |
| lncPANK1 27 | LNC PANK1 | ENST00000 455699 | 545 | 419 | UACAAUAGAGG CUUCAUAU | Pm0f00f00m00 ffff0f00 | ooooooooo ooosssssso |
| lncPANK1 28 | LNC PANK1 | ENST00000 455699 | 304 | 420 | UUCCUAACAUU UGGUCACU | Pmffff00f0fff0 0ff0f0 | ooooooooo ooosssssso |
| lncPANK1 29 | LNC PANK1 | ENST00000 455699 | 115 | 421 | UACUUCUACAU CCUGUUGU | Pm0fffff0f0ffff 0ff00 | ooooooooo ooosssssso |
| lncPANK1 30 | LNC PANK1 | ENST00000 455699 | 150 | 422 | UUGGAGAUGCU UUGCACAC | Pmf00m00f0fff f0f0f00 | ooooooooo ooosssssso |
| lncEBF3 1 | LNC EBF3 | ENST00000 456581 | 744 | 423 | UACAAAAGUCG CCAGGCAU | Pm0f00m00ff0 ff000f00 | ooooooooo ooosssssso |
| lncEBF3 2 | LNC EBF3 | ENST00000 456581 | 746 | 424 | UAUACAAAAGU CGCCAGGC | Pm0f0f00m00f f0ff0m00 | ooooooooo ooosssssso |
| lncEBF3 3 | LNC EBF3 | ENST00000 456581 | 1506 | 425 | UUCAUCCGUCU UUACCAGC | Pmff0fff0fffff0 ff000 | ooooooooo ooosssssso |
| lncEBF3 4 | LNC EBF3 | ENST00000 456581 | 1593 | 426 | UAUAUUCGUCU UUACUACC | Pm0f0fff0fffff0 ff0f0 | ooooooooo ooosssssso |
| lncEBF3 5 | LNC EBF3 | ENST00000 456581 | 1596 | 427 | UAGCAUAUUCG UCUUUACU | Pm00f0f0fff0ff fff0f0 | ooooooooo ooosssssso |
| lncEBF3 6 | LNC EBF3 | ENST00000 456581 | 1652 | 428 | UGUUGACGAUU CCUGCCAU | Pm0ff00f00ffff f0ff00 | ooooooooo ooosssssso |
| lncEBF3 7 | LNC EBF3 | ENST00000 456581 | 1655 | 429 | UGAUGUUGACG AUUCCUGC | Pm00f0ff00f00 fffff00 | ooooooooo ooosssssso |
| lncEBF3 8 | LNC EBF3 | ENST00000 456581 | 1656 | 430 | UAGAUGUUGAC GAUUCCUG | Pm000f0ff00f0 0ffffff0 | ooooooooo ooosssssso |
| lncEBF3 9 | LNC EBF3 | ENST00000 456581 | 1657 | 431 | UAAGAUGUUGA CGAUUCCU | Pmm000f0ff00 f00ffff0 | ooooooooo ooosssssso |
| lncEBF3 10 | LNC EBF3 | ENST00000 456581 | 2032 | 432 | UCUGCAACGGC UUCUUUGU | Pmff0f00f00fff ffff00 | ooooooooo ooosssssso |
| lncEBF3 11 | LNC EBF3 | ENST00000 456581 | 2209 | 433 | UCACAAUUCCA CGGAGCAA | Pm0f00ffff0f0 000f00 | ooooooooo ooosssssso |
| lncEBF3 12 | LNC EBF3 | ENST00000 456581 | 2593 | 434 | UCCUUUCGAAA UUGCUCAU | Pmffffff0m00ff 0fff00 | ooooooooo ooosssssso |
| lncEBF3 13 | LNC EBF3 | ENST00000 456581 | 2595 | 435 | UAACCUUUCGA AAUUGCUC | Pm00ffffff00m 0ff0ff0 | ooooooooo ooosssssso |
| lncEBF3 14 | LNC EBF3 | ENST00000 456581 | 2597 | 436 | UGGAACCUUUC GAAAUUGC | Pmm000ffffff0 00mff00 | ooooooooo ooosssssso |
| lncEBF3 15 | LNC EBF3 | ENST00000 456581 | 240 | 437 | UAAAAAGCCGA GCACUGGA | Pm000m00ff00 0f0ff000 | ooooooooo ooosssssso |
| lncEBF3 16 | LNC EBF3 | ENST00000 456581 | 2193 | 438 | UAAGAGAACGA UGUUUGUG | Pm000m000f0 0f0fff0f0 | ooooooooo ooosssssso |
| lncEBF3 17 | LNC EBF3 | ENST00000 456581 | 1878 | 439 | UUGGGACCAUU ACGUGAAA | Pmf0m00ff0ff0 f0f00m0 | ooooooooo ooosssssso |
| lncEBF3 18 | LNC EBF3 | ENST00000 456581 | 2205 | 440 | UAUUCCACGGA GCAAGAGA | Pm0ffff0fm000 f00m000 | ooooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncEBF3 19 | LNC EBF3 | ENST00000456581 | 1511 | 441 | UGACAAUCAUCCGUCUUUA | Pm00f00ff0fff0fffff0 | ooooooooooosssssso |
| lncEBF3 20 | LNC EBF3 | ENST00000456581 | 1843 | 442 | UUCACCUCUGGUACAUCUA | Pmff0fffff00f0f0fff0 | ooooooooooosssssso |
| lncEBF3 21 | LNC EBF3 | ENST00000456581 | 1879 | 443 | UCUGGGACCAUUACGUGAA | Pmff00m0ff0ff0f0f000 | ooooooooooosssssso |
| lncEBF3 22 | LNC EBF3 | ENST00000456581 | 1354 | 444 | UUCUGUACCAGUCAUAGCC | Pmfff0f0ff00ff0f00f0 | ooooooooooosssssso |
| lncEBF3 23 | LNC EBF3 | ENST00000456581 | 2317 | 445 | UUGUGAGUCUUACUGCAGA | Pmf0f000ffff0ff0f000 | ooooooooooosssssso |
| lncEBF3 24 | LNC EBF3 | ENST00000456581 | 1527 | 446 | UAAGCUUGGACCUCUAAGA | Pm000fff000fffff00m0 | ooooooooooosssssso |
| lncEBF3 25 | LNC EBF3 | ENST00000456581 | 1544 | 447 | UACAAAGGCCUACAGUAAA | Pm0f00m00fff0f00f000 | ooooooooooosssssso |
| lncEBF3 26 | LNC EBF3 | ENST00000456581 | 1325 | 448 | UCAGAUACAUGGGCGAACA | Pmf000f0f0f000f000f0 | ooooooooooosssssso |
| lncEBF3 27 | LNC EBF3 | ENST00000456581 | 2409 | 449 | UCUCAAGUCAUCAGACUCU | Pmfff000ff0ff000fff0 | ooooooooooosssssso |
| lncEBF3 28 | LNC EBF3 | ENST00000456581 | 933 | 450 | UUGAACUUACCAGAGACUU | Pmf000fff0ff000m0ff0 | ooooooooooosssssso |
| lncEBF3 29 | LNC EBF3 | ENST00000456581 | 1296 | 451 | UAAAGGGGUUAUUACAAAA | Pm000m000ff0ff0f00m0 | ooooooooooosssssso |
| lncEBF3 30 | LNC EBF3 | ENST00000456581 | 1297 | 452 | UCAAGGGGUUAUUACAAA | Pm000m000ff0ff0f000 | ooooooooooosssssso |
| lncScand1 1 | LNC Scand1 | ENST00000565493 | 849 | 453 | UAUCAUACGUCGGCAACCU | Pm0ff0f0f0ff00f00ff0 | ooooooooooosssssso |
| lncScand1 2 | LNC Scand1 | ENST00000565493 | 851 | 454 | UUUAUCAUACGUCGGCAAC | Pmff0ff0f0f0ff00f000 | ooooooooooosssssso |
| lncScand1 3 | LNC Scand1 | ENST00000565493 | 985 | 455 | UAACGUGGACGUAUCGCUU | Pm00f0f000f0f0ff0ff0 | ooooooooooosssssso |
| lncScand1 4 | LNC Scand1 | ENST00000565493 | 2663 | 456 | UAAAAUCGGGACUAAUUUG | Pmm000ff0m00ff00fff0 | ooooooooooosssssso |
| lncScand1 5 | LNC Scand1 | ENST00000565493 | 2971 | 457 | UUUUGUCCGCUAUAUACAC | Pmfff0fff0ff0f0f0f00 | ooooooooooosssssso |
| lncScand1 6 | LNC Scand1 | ENST00000565493 | 2973 | 458 | UAGUUUGUCCGCUAUAUAC | Pm00fff0fff0ff0f0f00 | ooooooooooosssssso |
| lncScand1 7 | LNC Scand1 | ENST00000565493 | 3283 | 459 | UAUGUCCGCUUAUAUACAC | Pm0f0fff0fff0f0f0f00 | ooooooooooosssssso |
| lncScand1 8 | LNC Scand1 | ENST00000565493 | 3285 | 460 | UCUAUGUCCGCUUAUAUAC | Pmff0f0fff0fff0f0f00 | ooooooooooosssssso |
| lncScand1 9 | LNC Scand1 | ENST00000565493 | 3288 | 461 | UCUCCUAUGUCCGCUUAUA | Pmfffff0f0fff0fff0f0 | ooooooooooosssssso |
| lncScand1 10 | LNC Scand1 | ENST00000565493 | 3312 | 462 | UACAUCGACUAGACGUAAA | Pm0f0ff00ff000f0f000 | ooooooooooosssssso |
| lncScand1 11 | LNC Scand1 | ENST00000565493 | 3313 | 463 | UAACAUCGACUAGACGUAA | Pm00f0ff00ff000f0f00 | ooooooooooosssssso |
| lncScand1 12 | LNC Scand1 | ENST00000565493 | 3314 | 464 | UUAACAUCGACUAGACGUA | Pmf00f0ff00ff000f0f0 | ooooooooooosssssso |
| lncScand1 13 | LNC Scand1 | ENST00000565493 | 4972 | 465 | UCAACACGCCUCUAGAUAA | Pmf00f0f0fffff000f00 | ooooooooooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncScand1 14 | LNC Scand1 | ENST00000565493 | 654 | 466 | UCUCUUCCGACAGCAAAGU | Pmfffffff00f00f00m00 | ooooooooooosssssso |
| lncScand1 15 | LNC Scand1 | ENST00000565493 | 656 | 467 | UCUCUCUUCCGACAGCAAA | Pmffffffffff00f0f000 | ooooooooooosssssso |
| lncScand1 16 | LNC Scand1 | ENST00000565493 | 733 | 468 | UAUAAACGGCCAGUAAAUC | Pm0f000f00ff00f000f0 | ooooooooooosssssso |
| lncScand1 17 | LNC Scand1 | ENST00000565493 | 736 | 469 | UUCCAUAAACGGCCAGUAA | Pmfff0f000f00ff00f00 | ooooooooooosssssso |
| lncScand1 18 | LNC Scand1 | ENST00000565493 | 991 | 470 | UUUAACAAACGUGGACGUA | Pmff00f000f0f000f0f0 | ooooooooooosssssso |
| lncScand1 19 | LNC Scand1 | ENST00000565493 | 1057 | 471 | UCCAGUCUAGCAUAGAACC | Pmff00fff00f0f00m0f0 | ooooooooooosssssso |
| lncScand1 20 | LNC Scand1 | ENST00000565493 | 1386 | 472 | UUCUUGCCUCGCUGUAAAC | Pmffff0ffff0ff0f0000 | ooooooooooosssssso |
| lncScand1 21 | LNC Scand1 | ENST00000565493 | 1459 | 473 | UUAGGACUCGUCUGUCCUU | Pmf00m0fff0fff0ffff0 | ooooooooooosssssso |
| lncScand1 22 | LNC Scand1 | ENST00000565493 | 1778 | 474 | UCAUACAUCGGGCACUUCU | Pmf0f0f0ff000f0ffff0 | ooooooooooosssssso |
| lncScand1 23 | LNC Scand1 | ENST00000565493 | 2158 | 475 | UUUUCCUACGAAUUCAAC | Pmffffff0f000ffff000 | ooooooooooosssssso |
| lncScand1 24 | LNC Scand1 | ENST00000565493 | 3981 | 476 | UUUAGAGGGGUGUUACUUA | Pmff000m000f0ff00ff0 | ooooooooooosssssso |
| lncScand1 25 | LNC Scand1 | ENST00000565493 | 4064 | 477 | UGUCUGCAUUCGCUCCUAA | Pm0fff0f0fff0fffff00 | ooooooooooosssssso |
| lncScand1 26 | LNC Scand1 | ENST00000565493 | 4168 | 478 | UCAAUGGUUAGACCAUCUG | Pmf00f00ff000ff0fff0 | ooooooooooosssssso |
| lncScand1 27 | LNC Scand1 | ENST00000565493 | 4435 | 479 | UACCAUCGUCUAGAUAUGG | Pm0ff0ff0fff000f0f00 | ooooooooooosssssso |
| lncScand1 28 | LNC Scand1 | ENST00000565493 | 4440 | 480 | UCUAAAACCAUCGUCUAGA | Pmff00m0ff0ff0fff000 | ooooooooooosssssso |
| lncScand1 29 | LNC Scand1 | ENST00000565493 | 4474 | 481 | UACUAAAAACGCUCUUGUA | Pm0ff00m00f0fffff0f0 | ooooooooooosssssso |
| lncScand1 30 | LNC Scand1 | ENST00000565493 | 4535 | 482 | UCAUUCGUAAAGCUUAGAU | Pmf0fff0f000mfff00m0 | ooooooooooosssssso |
| lncFAM69C2 1 | LNC FAM69C2 | ENST00000580048 | 166 | 483 | UUAUCUCUUAGCGGCUUCC | Pmf0ffffff00f00ffff0 | ooooooooooosssssso |
| lncFAM69C2 2 | LNC FAM69C2 | ENST00000580048 | 240 | 484 | UCGCUCAUCGAAUUUAGAU | Pmf0fff0ff000fff0000 | ooooooooooosssssso |
| lncFAM69C2 3 | LNC FAM69C2 | ENST00000580048 | 241 | 485 | UGCGCUCAUCGAAUUUAGA | Pm0f0fff0ff000fff000 | ooooooooooosssssso |
| lncFAM69C2 4 | LNC FAM69C2 | ENST00000580048 | 242 | 486 | UCGCGCUCAUCGAAUUUAG | Pmf0f0fff0ff000fff00 | ooooooooooosssssso |
| lncFAM69C2 5 | LNC FAM69C2 | ENST00000580048 | 764 | 487 | UCUUGUCGAACGUUUAAA | Pmfff0ff000f0ffff000 | ooooooooooosssssso |
| lncFAM69C2 6 | LNC FAM69C2 | ENST00000580048 | 766 | 488 | UUCCUUGUCGAACGUUUUA | Pmfffff0ff000f0ffff0 | ooooooooooosssssso |
| lncFAM69C2 7 | LNC FAM69C2 | ENST00000580048 | 768 | 489 | UAGCCUUGUCGAACGUUU | Pm00fffff0ff000f0ff0 | ooooooooooosssssso |
| lncFAM69C2 8 | LNC FAM69C2 | ENST00000580048 | 790 | 490 | UGUGCCGUUAACGUUCAUA | Pm0f0ff0ff00f0fff0f0 | ooooooooooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncFAM69C2 9 | LNC FAM69C2 | ENST00000 580048 | 795 | 491 | UAUGCUGUGCC GUUAACGU | Pmf0ff0ff0ff0f f00f00 | ooooooooo ooossssso |
| lncFAM69C2 10 | LNC FAM69C2 | ENST00000 580048 | 932 | 492 | UUUAUUCGUCU ACACAGGU | Pmff0fff0fff0f0 f0000 | ooooooooo ooossssso |
| lncFAM69C2 11 | LNC FAM69C2 | ENST00000 580048 | 1391 | 493 | UCCACUCGUUG GAAUGAUU | Pmff0fff0ff0m 00f00f0 | ooooooooo ooossssso |
| lncFAM69C2 12 | LNC FAM69C2 | ENST00000 580048 | 1999 | 494 | UAAUGUCGUUA UAAACUUG | Pm00f0ff0ff0f0 00fff0 | ooooooooo ooossssso |
| lncFAM69C2 13 | LNC FAM69C2 | ENST00000 580048 | 2001 | 495 | UGCAAUGUCGU UAUAAACU | Pm0f00f0ff0ff0 f000f0 | ooooooooo ooossssso |
| lncFAM69C2 14 | LNC FAM69C2 | ENST00000 580048 | 531 | 496 | UUUUCUCGAAA UCGGAGCG | Pmffffff0000ff 0m00f0 | ooooooooo ooossssso |
| lncFAM69C2 15 | LNC FAM69C2 | ENST00000 580048 | 535 | 497 | UGUCAUUUCUC GAAAUCGG | Pm0ff0ffffff00 0mff00 | ooooooooo ooossssso |
| lncFAM69C2 16 | LNC FAM69C2 | ENST00000 580048 | 597 | 498 | UGAGCCAUUCG AGAGAUUU | Pm000ff0fff00 000mff0 | ooooooooo ooossssso |
| lncFAM69C2 17 | LNC FAM69C2 | ENST00000 580048 | 876 | 499 | UUAACUCGAGG UUCAUGAA | Pmf00fff0000ff f0f000 | ooooooooo ooossssso |
| lncFAM69C2 18 | LNC FAM69C2 | ENST00000 580048 | 879 | 500 | UCUCUAACUCG AGGUUCAU | Pmffff00fff000 0fff00 | ooooooooo ooossssso |
| lncFAM69C2 19 | LNC FAM69C2 | ENST00000 580048 | 1573 | 501 | UUGCAUCUUCG CAGCUUAG | Pmf0f0ffffff0f0 0fff00 | ooooooooo ooossssso |
| lncFAM69C2 20 | LNC FAM69C2 | ENST00000 580048 | 1575 | 502 | UUUUGCAUCUU CGCAGCUU | Pmfff0f0ffffff0f 00ff0 | ooooooooo ooossssso |
| lncFAM69C2 21 | LNC FAM69C2 | ENST00000 580048 | 1927 | 503 | UCCACUAAGCA UAACCUAG | Pmff0ff000f0f0 0fff00 | ooooooooo ooossssso |
| lncFAM69C2 22 | LNC FAM69C2 | ENST00000 580048 | 2019 | 504 | UCAUGGAGUGU AGCAUCCA | Pmf0f0000f0f0 0f0fff0 | ooooooooo ooossssso |
| lncFAM69C2 23 | LNC FAM69C2 | ENST00000 580048 | 2674 | 505 | UAGGUCCUUGA UACCAACA | Pm000fffff00f0 ff00f0 | ooooooooo ooossssso |
| lncFAM69C2 24 | LNC FAM69C2 | ENST00000 580048 | 2721 | 506 | UUUCAAUAGGG CAUUGAGA | Pmfff00f0m00f 0ff0m00 | ooooooooo ooossssso |
| lncFAM69C2 25 | LNC FAM69C2 | ENST00000 580048 | 3316 | 507 | UUACAAGUUGG GAUCCUCU | Pmf0f000ff000 0fffff0 | ooooooooo ooossssso |
| lncFAM69C2 26 | LNC FAM69C2 | ENST00000 580048 | 1749 | 508 | UUUAUUCGAU AGUUUCUG | Pmff0ffff00f00 fffff0 | ooooooooo ooossssso |
| lncFAM69C2 27 | LNC FAM69C2 | ENST00000 580048 | 2532 | 509 | UCUCCUGGUAU AAGUGCUU | Pmffff00f0f00 0f0ff0 | ooooooooo ooossssso |
| lncFAM69C2 28 | LNC FAM69C2 | ENST00000 580048 | 2724 | 510 | UAUGUUCAAUA GGGCAUUG | Pm0f0fff00f00 m0f0ff0 | ooooooooo ooossssso |
| lncFAM69C2 29 | LNC FAM69C2 | ENST00000 580048 | 2744 | 511 | UAGCCAUCUUA CUACAGCC | Pm00ff0ffff0ff 0f00f0 | ooooooooo ooossssso |
| lncFAM69C2 30 | LNC FAM69C2 | ENST00000 580048 | 3321 | 512 | UGCAGCUACAA GUUGGGAU | Pm0f00ff0f000 ff000m0 | ooooooooo ooossssso |
| lncVEZF1 1 | LNC VEZF1 | ENST00000 585065 | 239 | 513 | UCAGUACUCGA UAUAUCAA | Pmf00f0fff00f0 f0ff00 | ooooooooo ooossssso |
| lncVEZF1 2 | LNC VEZF1 | ENST00000 585065 | 2307 | 514 | UUUUCUCGAGU ACAGAGGU | Pmffffff000f0f 00m000 | ooooooooo ooossssso |
| lncVEZF1 3 | LNC VEZF1 | ENST00000 585065 | 2637 | 515 | UCCAACAAAUC GCAAGUAA | Pmff00f000ff0f 000f00 | ooooooooo ooossssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncVEZF1 4 | LNC VEZF1 | ENST00000585065 | 2638 | 516 | UUCCACAAAU CGCAAGUA | Pmfff00f000ff0 f000f0 | ooooooooo ooosssssso |
| lncVEZF1 5 | LNC VEZF1 | ENST00000585065 | 2863 | 517 | UGGUAGUCGAG GGCUUUUA | Pm00f00ff000 m0fffff0 | ooooooooo ooosssssso |
| lncVEZF1 6 | LNC VEZF1 | ENST00000585065 | 3477 | 518 | UUCUGCCGUUG UCAAUUAC | Pmfff0ff0ff0ff0 0ff00 | ooooooooo ooosssssso |
| lncVEZF1 7 | LNC VEZF1 | ENST00000585065 | 3478 | 519 | UCUCUGCCGUU GUCAAUUA | Pmffff0ff0ff0ff 00ff0 | ooooooooo ooosssssso |
| lncVEZF1 8 | LNC VEZF1 | ENST00000585065 | 3675 | 520 | UCUAAGGUAAA CGGGCAAA | Pmff00m0f000 f000f000 | ooooooooo ooosssssso |
| lncVEZF1 9 | LNC VEZF1 | ENST00000585065 | 3804 | 521 | UUGUUAUCGAG UGGUUCUA | Pmf0ff0ff000f0 0ffff0 | ooooooooo ooosssssso |
| lncVEZF1 10 | LNC VEZF1 | ENST00000585065 | 3805 | 522 | UGUGUUAUCGA GUGGUUCU | Pm0f0ff0ff000f 00fff0 | ooooooooo ooosssssso |
| lncVEZF1 11 | LNC VEZF1 | ENST00000585065 | 3806 | 523 | UGGUGUUAUCG AGUGGUUC | Pm00f0ff0ff00 0f00ff0 | ooooooooo ooosssssso |
| lncVEZF1 12 | LNC VEZF1 | ENST00000585065 | 3808 | 524 | UUUGGUGUUAU CGAGUGGU | Pmff00f0ff0ff0 00f000 | ooooooooo ooosssssso |
| lncVEZF1 13 | LNC VEZF1 | ENST00000585065 | 4348 | 525 | UAGAUGGACGC AUUAUUUU | Pm000f000f0f0 ff0fff0 | ooooooooo ooosssssso |
| lncVEZF1 14 | LNC VEZF1 | ENST00000585065 | 4349 | 526 | UCAGAUGGACG CAUUAUUU | Pmf000f000f0f 0ff0ff0 | ooooooooo ooosssssso |
| lncVEZF1 15 | LNC VEZF1 | ENST00000585065 | 4350 | 527 | UUCAGAUGGAC GCAUUAUU | Pmff000f000f0 f0ff0f0 | ooooooooo ooosssssso |
| lncVEZF1 16 | LNC VEZF1 | ENST00000585065 | 4351 | 528 | UUUCAGAUGGA CGCAUUAU | Pmfff000f000f 0f0ff00 | ooooooooo ooosssssso |
| lncVEZF1 17 | LNC VEZF1 | ENST00000585065 | 2309 | 529 | UAGUUUCUCGA GUACAGAG | Pm00fffff000f 0f0m00 | ooooooooo ooosssssso |
| lncVEZF1 18 | LNC VEZF1 | ENST00000585065 | 2312 | 530 | UCAAAGUUUCU CGAGUACA | Pmf00m0ffffff 000f0f0 | ooooooooo ooosssssso |
| lncVEZF1 19 | LNC VEZF1 | ENST00000585065 | 2449 | 531 | UGUAGGUAAUG GGUCACAC | Pm0f000f00f00 0ff0f00 | ooooooooo ooosssssso |
| lncVEZF1 20 | LNC VEZF1 | ENST00000585065 | 2539 | 532 | UACUCAUAGGC ACCAACAU | Pm0fff0f000f0f f00f00 | ooooooooo ooosssssso |
| lncVEZF1 21 | LNC VEZF1 | ENST00000585065 | 2541 | 533 | UAUACUCAUAG GCACCAAC | Pm0f0fff0f000f 0ff000 | ooooooooo ooosssssso |
| lncVEZF1 22 | LNC VEZF1 | ENST00000585065 | 3674 | 534 | UUAAGGUAAAC GGGCAAAG | Pmf00m0f000f 000f0m00 | ooooooooo ooosssssso |
| lncVEZF1 23 | LNC VEZF1 | ENST00000585065 | 3727 | 535 | UUACUUUCGCC AAGUGACA | Pmf0fffff0ff00 0f00f0 | ooooooooo ooosssssso |
| lncVEZF1 24 | LNC VEZF1 | ENST00000585065 | 3730 | 536 | UUUUUACUUUC GCCAAGUG | Pmffff0fffff0ff 000f0 | ooooooooo ooosssssso |
| lncVEZF1 25 | LNC VEZF1 | ENST00000585065 | 4441 | 537 | UCUCUAGUCCA AGACAUCU | Pmffff00fff0m 00f0ff0 | ooooooooo ooosssssso |
| lncVEZF1 26 | LNC VEZF1 | ENST00000585065 | 4444 | 538 | UUGUCUCUAGU CCAAGACA | Pmf0fffff00fff0 00mf0 | ooooooooo ooosssssso |
| lncVEZF1 27 | LNC VEZF1 | ENST00000585065 | 4650 | 539 | UAAAAAUCGAA CUUCUGGU | Pm00m00ff000 fffff000 | ooooooooo ooosssssso |
| lncVEZF1 28 | LNC VEZF1 | ENST00000585065 | 2723 | 540 | UGCUAAACCUA UCAGCUUC | Pm0ff000fff0ff 00fff0 | ooooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncVEZF1 29 | LNC VEZF1 | ENST00000 585065 | 3116 | 541 | UAAGCACACUA AGGGCUUU | Pm000f0f0ff0 m000fff0 | ooooooooo ooosssssso |
| lncVEZF1 30 | LNC VEZF1 | ENST00000 585065 | 3369 | 542 | UUAAUGGACCA ACUCUUUA | Pmf00000ff00 ffffff0 | ooooooooo ooosssssso |
| lncFBXO 1 | LNC FBXO 256 | ENST00000 607352 | 198 | 543 | UGACGACAUAU AAACGGCC | Pm00f00f0f0f0 00f00f0 | ooooooooo ooosssssso |
| lncFBXO 2 | LNC FBXO 256 | ENST00000 607352 | 199 | 544 | UAGACGACAUA UAAACGGC | Pm000f00f0f0f 000f000 | ooooooooo ooosssssso |
| lncFBXO 3 | LNC FBXO 256 | ENST00000 607352 | 886 | 545 | UACUUACGACA AAGCUACA | Pm0fff0f00f00 m0ff0f0 | ooooooooo ooosssssso |
| lncFBXO 4 | LNC FBXO 256 | ENST00000 607352 | 887 | 546 | UAACUUACGAC AAAGCUAC | Pm00fff0f00f0 m00ff00 | ooooooooo ooosssssso |
| lncFBXO 5 | LNC FBXO 256 | ENST00000 607352 | 888 | 547 | UUAACUUACGA CAAAGCUA | Pmf00fff0f00f0 000ff0 | ooooooooo ooosssssso |
| lncFBXO 6 | LNC FBXO 256 | ENST00000 607352 | 889 | 548 | UAUAACUUACG ACAAAGCU | Pm0f00fff0f00f 00m0f0 | ooooooooo ooosssssso |
| lncFBXO 7 | LNC FBXO 256 | ENST00000 607352 | 890 | 549 | UCAUAACUUAC GACAAAGC | Pmf0f00fff0f00 f00m00 | ooooooooo ooosssssso |
| lncFBXO 8 | LNC FBXO 256 | ENST00000 607352 | 2596 | 550 | UAACAACGCUC UCAACCAG | Pm00f00f0ffff f00ff00 | ooooooooo ooosssssso |
| lncFBXO 9 | LNC FBXO 256 | ENST00000 607352 | 2598 | 551 | UUAACAACGC UCUCAACC | Pmf000f00f0fff ff00f0 | ooooooooo ooosssssso |
| lncFBXO 10 | LNC FBXO 256 | ENST00000 607352 | 2842 | 552 | UUCAGUCGCAA GACAGAAC | Pmff00ff0f000 mf00m00 | ooooooooo ooosssssso |
| lncFBXO 11 | LNC FBXO 256 | ENST00000 607352 | 2844 | 553 | UGAUCAGUCGC AAGACAGA | Pm00ff00ff0f0 0m0f000 | ooooooooo ooosssssso |
| lncFBXO 12 | LNC FBXO 256 | ENST00000 607352 | 2846 | 554 | UAAGAUCAGUC GCAAGACA | Pm0000ff00ff0 f0m00f0 | ooooooooo ooosssssso |
| lncFBXO 13 | LNC FBXO 256 | ENST00000 607352 | 2845 | 555 | UAGAUCAGUCG CAAGACAG | Pm000ff00ff0f 0000f00 | ooooooooo ooosssssso |
| lncFBXO 14 | LNC FBXO 256 | ENST00000 607352 | 2847 | 556 | UGAAGAUCAGU CGCAAGAC | Pm00m00ff00f f0f00m00 | ooooooooo ooosssssso |
| lncFBXO 15 | LNC FBXO 256 | ENST00000 607352 | 2871 | 557 | UAGUAACGGAU AGGACAAC | Pm0f00f000f0 000f000 | ooooooooo ooosssssso |
| lncFBXO 16 | LNC FBXO 256 | ENST00000 607352 | 2873 | 558 | UUCAGUAACGG AUAGGACA | Pmff00f00f000 f00m0f0 | ooooooooo ooosssssso |
| lncFBXO 17 | LNC FBXO 256 | ENST00000 607352 | 3806 | 559 | UGGUGUUAUCG AGUGGUUC | Pm00f0ff0ff00 0f00ff0 | ooooooooo ooosssssso |
| lncFBXO 18 | LNC FBXO 256 | ENST00000 607352 | 685 | 560 | UAGCUAGAUCU ACCUCACA | Pm00ff000fff0f fff0f0 | ooooooooo ooosssssso |
| lncFBXO 19 | LNC FBXO 256 | ENST00000 607352 | 687 | 561 | UGAAGCUAGAU CUACCUCA | Pmm000ff000f ff0ffff0 | ooooooooo ooosssssso |
| lncFBXO 20 | LNC FBXO 256 | ENST00000 607352 | 689 | 562 | UAUGAAGCUAG AUCUACCU | Pm0f00m0ff00 0fff0ff0 | ooooooooo ooosssssso |
| lncFBXO 21 | LNC FBXO 256 | ENST00000 607352 | 1073 | 563 | UGGAUUGGAUA CCUUAAGA | Pm000ff000f0f fff00m0 | ooooooooo ooosssssso |
| lncFBXO 22 | LNC FBXO 256 | ENST00000 607352 | 1071 | 564 | UAUUGGAUACC UUAAGAUG | Pm0ff000f0ffff 0000f0 | ooooooooo ooosssssso |
| lncFBXO 23 | LNC FBXO 256 | ENST00000 607352 | 2071 | 565 | UACCUAUGCUA GUCAAGAG | Pm0fff0f0ff00f f000m0 | ooooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncFBXO 24 | LNC FBXO 256 | ENST00000 607352 | 2074 | 566 | UCAGACCUAUG CUAGUCAA | Pmf000fff0f0ff 00ff00 | ooooooooo ooossssso |
| lncFBXO 25 | LNC FBXO 256 | ENST00000 607352 | 2076 | 567 | UAACAGACCUA UGCUAGUC | Pm00f000fff0f 0ff00f0 | ooooooooo ooossssso |
| lncFBXO 26 | LNC FBXO 256 | ENST00000 607352 | 2600 | 568 | UAUUAAACAAC GCUCUCAA | Pm0ff000f00f0 fffff00 | ooooooooo ooossssso |
| lncFBXO 27 | LNC FBXO 256 | ENST00000 607352 | 2870 | 569 | UGUAACGGAUA GGACAACC | Pm0f00f000f00 m0f00f0 | ooooooooo ooossssso |
| lncFBXO 28 | LNC FBXO 256 | ENST00000 607352 | 2874 | 570 | UUUCAGUAACG GAUAGGAC | Pmfff00f00f00 0f000m0 | ooooooooo ooossssso |
| lncFBXO 29 | LNC FBXO 256 | ENST00000 607352 | 2876 | 571 | UCUUUCAGUAA CGGAUAGG | Pmfffff00f00f0 00f000 | ooooooooo ooossssso |
| lncFBXO 30 | LNC FBXO 256 | ENST00000 607352 | 200 | 572 | UAAGACGACAU AUAAACGG | Pmm000f00f0f 0f000f00 | ooooooooo ooossssso |
| lncNDST3 1 | LNC NDST3 | ENST00000 602414 | 77 | 573 | UAACUACGUAC UUUCACCU | Pm00ff0f0f0fff ff0ff0 | ooooooooo ooossssso |
| lncNDST3 2 | LNC NDST3 | ENST00000 602414 | 78 | 574 | UCAACUACGUA CUUUCACC | Pmf00ff0f0f0ff fff0f0 | ooooooooo ooossssso |
| lncNDST3 3 | LNC NDST3 | ENST00000 602414 | 79 | 575 | UACAACUACGU ACUUUCAC | Pm0f00ff0f0f0f ffff00 | ooooooooo ooossssso |
| lncNDST3 4 | LNC NDST3 | ENST00000 602414 | 81 | 576 | UAGACAACUAC GUACUUUC | Pm000f00ff0f0 f0fff0 | ooooooooo ooossssso |
| lncNDST3 5 | LNC NDST3 | ENST00000 602414 | 440 | 577 | UUCCAUCGUAA UGUGUUCA | Pmfff0ff0f00f0 f0fff0 | ooooooooo ooossssso |
| lncNDST3 6 | LNC NDST3 | ENST00000 602414 | 441 | 578 | UAUCCAUCGUA AUGUGUUC | Pm0fff0ff0f00f 0f0ff0 | ooooooooo ooossssso |
| lncNDST3 7 | LNC NDST3 | ENST00000 602414 | 442 | 579 | UCAUCCAUCGU AAUGUGUU | Pmf0fff0ff0f00 f0f0f0 | ooooooooo ooossssso |
| lncNDST3 8 | LNC NDST3 | ENST00000 602414 | 443 | 580 | UUCAUCCAUCG UAAUGUGU | Pmff0fff0ff0f0 0f0f00 | ooooooooo ooossssso |
| lncNDST3 9 | LNC NDST3 | ENST00000 602414 | 444 | 581 | UAUCAUCCAUC GUAAUGUG | Pm0ff0fff0ff0f 00f0f0 | ooooooooo ooossssso |
| lncNDST3 10 | LNC NDST3 | ENST00000 602414 | 445 | 582 | UCAUCAUCCAU CGUAAUGU | Pmf0ff0fff0ff0f 00f00 | ooooooooo ooossssso |
| lncNDST3 11 | LNC NDST3 | ENST00000 602414 | 508 | 583 | UAUUGCCGGAU GCUGAAUA | Pm0ff0ff000f0f f000f0 | ooooooooo ooossssso |
| lncNDST3 12 | LNC NDST3 | ENST00000 602414 | 523 | 584 | UAACUACGAUA AGUCCAUU | Pm00ff0f00f00 0fff0f0 | ooooooooo ooossssso |
| lncNDST3 13 | LNC NDST3 | ENST00000 602414 | 524 | 585 | UCAACUACGAU AAGUCCAU | Pmf00ff0f00f0 00fff00 | ooooooooo ooossssso |
| lncNDST3 14 | LNC NDST3 | ENST00000 602414 | 625 | 586 | UUAUCACGGAC CACCUUAA | Pmf0ff0f000ff0 ffff00 | ooooooooo ooossssso |
| lncNDST3 15 | LNC NDST3 | ENST00000 602414 | 626 | 587 | UUUAUCACGGA CCACCUUA | Pmff0ff0f000ff 0ffff0 | ooooooooo ooossssso |
| lncNDST3 16 | LNC NDST3 | ENST00000 602414 | 627 | 588 | UAUUAUCACGG ACCACCUU | Pm0ff0ff0f000f f0fff0 | ooooooooo ooossssso |
| lncNDST3 17 | LNC NDST3 | ENST00000 602414 | 628 | 589 | UAAUUAUCACG GACCACCU | Pm00ff0ff0f00 0ff0ff0 | ooooooooo ooossssso |
| lncNDST3 18 | LNC NDST3 | ENST00000 602414 | 629 | 590 | UUAAUUAUCAC GGACCACC | Pmf00ff0ff0f00 0ff0f0 | ooooooooo ooossssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncNDST3 19 | LNC NDST3 | ENST00000 602414 | 91 | 591 | UAACUUACGAA AGACAACU | Pm00fff0f000 m00f00f0 | ooooooooo ooosssssso |
| lncNDST3 20 | LNC NDST3 | ENST00000 602414 | 92 | 592 | UUAACUUACGA AAGACAAC | Pmf00fff0f00m 000f000 | ooooooooo ooosssssso |
| lncNDST3 21 | LNC NDST3 | ENST00000 602414 | 515 | 593 | UUAAGUCCAUU GCCGGAUG | Pm000fff0ff0f f000f0 | ooooooooo ooosssssso |
| lncNDST3 22 | LNC NDST3 | ENST00000 602414 | 550 | 594 | UGAUAUUAUUC GGAACACC | Pm00f0ff0fff0 m00f0f0 | ooooooooo ooosssssso |
| lncNDST3 23 | LNC NDST3 | ENST00000 602414 | 551 | 595 | UGGAUAUUAUU CGGAACAC | Pm000f0ff0fff0 0m0f00 | ooooooooo ooosssssso |
| lncNDST3 24 | LNC NDST3 | ENST00000 602414 | 623 | 596 | UUCACGGACCA CCUUAAAU | Pmff0f000ff0ff ff00m0 | ooooooooo ooosssssso |
| lncNDST3 25 | LNC NDST3 | ENST00000 602414 | 624 | 597 | UAUCACGGACC ACCUUAAA | Pm0ff0f000ff0f fff000 | ooooooooo ooosssssso |
| lncNDST3 26 | LNC NDST3 | ENST00000 602414 | 630 | 598 | UUUAAUUAUCA CGGACCAC | Pmff00ff0ff0f0 00ff00 | ooooooooo ooosssssso |
| lncNDST3 27 | LNC NDST3 | ENST00000 602414 | 130 | 599 | UUUUAGGUAAG GCAGUAAG | Pmfff000f0m0 0f00f000 | ooooooooo ooosssssso |
| lncNDST3 28 | LNC NDST3 | ENST00000 602414 | 131 | 600 | UUUUUAGGUAA GGCAGUAA | Pmffff000f000 mf00f00 | ooooooooo ooosssssso |
| lncNDST3 29 | LNC NDST3 | ENST00000 602414 | 516 | 601 | UAUAAGUCCAU UGCCGGAU | Pm0f000fff0ff0 ff00m0 | ooooooooo ooosssssso |
| lncNDST3 30 | LNC NDST3 | ENST00000 602414 | 519 | 602 | UACGAUAAGUC CAUUGCCG | Pm0f00f000fff 0ff0ff0 | ooooooooo ooosssssso |
| lncMALAT1 1 | LNC Malat1 | MALAT1 | 445 | 603 | UCCAACUAAGC GAAUGGCU | Pmff00ff000f0 00f00f0 | ooooooooo ooosssssso |
| lncMALAT1 2 | LNC Malat1 | MALAT1 | 860 | 604 | UUCCAUUACGC AACUGAGC | Pmfff0ff0f0f00 ff00m0 | ooooooooo ooosssssso |
| lncMALAT1 3 | LNC Malat1 | MALAT1 | 1006 | 605 | UUUAAACGGGU CAUCAAAC | Pmff000f000f0 0ff00m0 | ooooooooo ooosssssso |
| lncMALAT1 4 | LNC Malat1 | MALAT1 | 1007 | 606 | UUUUAAACGGG UCAUCAAA | Pmfff000f000ff 0ff000 | ooooooooo ooosssssso |
| lncMALAT1 5 | LNC Malat1 | MALAT1 | 1818 | 607 | UUCGUCUGCGU UUAGUAAA | Pmff0fff0f0fff0 0f000 | ooooooooo ooosssssso |
| lncMALAT1 6 | LNC Malat1 | MALAT1 | 1821 | 608 | UUUUUCGUCUG CGUUUAGU | Pmfffff0fff0f0f ff000 | ooooooooo ooosssssso |
| lncMALAT1 7 | LNC Malat1 | MALAT1 | 2513 | 609 | UCUUCCGUUAC GAAAGUCC | Pmfffff0ff0f00 0m0ff0 | ooooooooo ooosssssso |
| lncMALAT1 8 | LNC Malat1 | MALAT1 | 2813 | 610 | UAAUCGUUAGC GCUCCUUC | Pm00ff0ff00f0f fffff0 | ooooooooo ooosssssso |
| lncMALAT1 9 | LNC Malat1 | MALAT1 | 3087 | 611 | UCACCUCAGUA CGAAACUC | Pmf0ffff00f0f0 0m0fff | ooooooooo ooosssssso |
| lncMALAT1 10 | LNC Malat1 | MALAT1 | 7883 | 612 | UUUGAAACCGA UUAUGGAU | Pmff0m00ff00f f0f00m0 | ooooooooo ooosssssso |
| lncMALAT1 11 | LNC Malat1 | MALAT1 | 8585 | 613 | UAUUAGGUUCU CGUGUAAA | Pm0ff000fffff0 f0f000 | ooooooooo ooosssssso |
| lncMALAT1 12 | LNC Malat1 | MALAT1 | 1218 | 614 | UUCACCGGAAU UCGAUCAC | Pmff0ff0m00ff f00ff00 | ooooooooo ooosssssso |
| lncMALAT1 13 | LNC Malat1 | MALAT1 | 1251 | 615 | UCGAGGCGUAU UUAUAGAC | Pm0m0f0f0ff f0f00m0 | ooooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncMALAT1 14 | LNC Malat1 | MALAT1 | 3014 | 616 | UAACAUAUUGC CGACCUCA | Pm00f0f0ff0ff0 0ffff0 | ooooooooo ooosssssso |
| lncMALAT1 15 | LNC Malat1 | MALAT1 | 5094 | 617 | UGUAGAUUCCG UAACUUUA | Pm0f000ffff0f0 0ffff0 | ooooooooo ooosssssso |
| lncMALAT1 16 | LNC Malat1 | MALAT1 | 5338 | 618 | UCUGAGGCAAA CGAAACAU | Pmff0000f000f 00m0f00 | ooooooooo ooosssssso |
| lncMALAT1 17 | LNC Malat1 | MALAT1 | 5970 | 619 | UAGUGUUCGCA GACAAAGU | Pm00f0fff0f00 0f00m00 | ooooooooo ooosssssso |
| lncMALAT1 18 | LNC Malat1 | MALAT1 | 6008 | 620 | UUCGUUCUUCC GCUCAAAU | Pmff0fffffff0f ff00m0 | ooooooooo ooosssssso |
| lncMALAT1 19 | LNC Malat1 | MALAT1 | 6634 | 621 | UAUAGCAGCGG GAUCAGAA | Pm0f00f00f00 m0ff00m0 | ooooooooo ooosssssso |
| lncMALAT1 20 | LNC Malat1 | MALAT1 | 6662 | 622 | UUACUCCAGUC GUUUCACA | Pmf0ffff00ff0ff ff0f0 | ooooooooo ooosssssso |
| lncMALAT1 21 | LNC Malat1 | MALAT1 | 6782 | 623 | UUCACAAAUAC GACUGCUU | Pmff0f000f0f0 0ff0ff0 | ooooooooo ooosssssso |
| lncMALAT1 22 | LNC Malat1 | MALAT1 | 7439 | 624 | UUUAAGCCUUC GGUGCCUU | Pmff000fffff00 f0fff0 | ooooooooo ooosssssso |
| lncMALAT1 23 | LNC Malat1 | MALAT1 | 7681 | 625 | UAAGCACCGCU UGAGAUUU | Pm000f0ff0fff0 000ff0 | ooooooooo ooosssssso |
| lncMALAT1 24 | LNC Malat1 | MALAT1 | 8219 | 626 | UUCAGCUUCCG CUAAGAUG | Pmff00ffffff0ff0 00mf0 | ooooooooo ooosssssso |
| lncMALAT1 25 | LNC Malat1 | MALAT1 | 4012 | 627 | UUUUGGCCUAC UCAAGCUC | Pmfff00fff0fff0 00ff0 | ooooooooo ooosssssso |
| lncMALAT1 26 | LNC Malat1 | MALAT1 | 2325 | 628 | UUUCUGGUCUA CGUAAACA | Pmffff00fff0f0f 000f0 | ooooooooo ooosssssso |
| lncMALAT1 27 | LNC Malat1 | MALAT1 | 2742 | 629 | UUCUUCACCAC GAACUGCU | Pmfffff0ff0f00 0ff0f0 | ooooooooo ooosssssso |
| lncMALAT1 28 | LNC Malat1 | MALAT1 | 1423 | 630 | UACUUAACGCU AAGCAAUA | Pm0fff00f0ff00 0f00f0 | ooooooooo ooosssssso |
| lncMALAT1 29 | LNC Malat1 | MALAT1 | 1610 | 631 | UGUAUUAAUUC GGGGCUCU | Pm0f0ff00fff0 m00fff0 | ooooooooo ooosssssso |
| lncMALAT1 30 | LNC Malat1 | MALAT1 | 810 | 632 | UAAAUGGCGGA CUUUCUCC | Pm000f00f000f ffffff0 | ooooooooo ooosssssso |
| lncFAM22E1 1 | LNC FAM22E1 | ENST00000 605920 | 509 | 633 | UGGGAAUACCU CUAGUUCU | Pm00m00f0ffff f00fff0 | ooooooooo ooosssssso |
| lncFAM22E1 2 | LNC FAM22E1 | ENST00000 605920 | 716 | 634 | UAUAAAGCGCA CGGAUGGA | Pm0f00m0f0f0 f000f000 | ooooooooo ooosssssso |
| lncFAM22E1 3 | LNC FAM22E1 | ENST00000 605920 | 1139 | 635 | UGAUUUAAGGC UGGUAUCC | Pm00fff0m00ff 00f0ff0 | ooooooooo ooosssssso |
| lncFAM22E1 4 | LNC FAM22E1 | ENST00000 605920 | 1148 | 636 | UAGUCGGCUCG AUUUAAGG | Pm00ff00fff00f ff00m0 | ooooooooo ooosssssso |
| lncFAM22E1 5 | LNC FAM22E1 | ENST00000 605920 | 1149 | 637 | UUAGUCGGCUC GAUUUAAG | Pmf00ff00fff00 fff000 | ooooooooo ooosssssso |
| lncFAM22E1 6 | LNC FAM22E1 | ENST00000 605920 | 1150 | 638 | UGUAGUCGGCU CGAUUUAA | Pmf0f00ff00fff0 0fff00 | ooooooooo ooosssssso |
| lncFAM22E1 7 | LNC FAM22E1 | ENST00000 605920 | 1328 | 639 | UAUUCCGCUGA AGCCAACU | Pm0ffff0ff00m 0ff00f0 | ooooooooo ooosssssso |
| lncFAM22E1 8 | LNC FAM22E1 | ENST00000 605920 | 1334 | 640 | UGUAGGUAUUC CGCUGAAG | Pm0f000f0ffff0 0f00m0 | ooooooooo ooosssssso |

TABLE 2-continued

Antisense Strand Oligonucleotides

| Oligo ID | Gene Name | Accession number | Start Site | SEQ ID NO: | Antisense sequence | AntiSense Chemistry | AntiSense Backbone |
|---|---|---|---|---|---|---|---|
| lncFAM22E1 9 | LNC FAM22E1 | ENST00000 605920 | 1335 | 641 | UAGUAGGUAUU CCGCUGAA | Pm00f000f0ffff 0ff000 | ooooooooo ooosssssso |
| lncFAM22E1 10 | LNC FAM22E1 | ENST00000 605920 | 1362 | 642 | UCAAUCGGCUU GUUGAAUA | Pmf00ff00fff0f f000f0 | ooooooooo ooosssssso |
| lncFAM22E1 11 | LNC FAM22E1 | ENST00000 605920 | 1363 | 643 | UUCAAUCGGCU UGUUGAAU | Pmff00ff00fff0 ff00m0 | ooooooooo ooosssssso |
| lncFAM22E1 12 | LNC FAM22E1 | ENST00000 605920 | 1364 | 644 | UAUCAAUCGGC UUGUUGAA | Pm0ff00ff00fff 0ff000 | ooooooooo ooosssssso |
| lncFAM22E1 13 | LNC FAM22E1 | ENST00000 605920 | 1365 | 645 | UGAUCAAUCGG CUUGUUGA | Pm00ff00ff00ff f0ff00 | ooooooooo ooosssssso |
| lncFAM22E1 14 | LNC FAM22E1 | ENST00000 605920 | 1366 | 646 | UUGAUCAAUCG GCUUGUUG | Pmf00ff00ff00f ff0ff0 | ooooooooo ooosssssso |
| lncFAM22E1 15 | LNC FAM22E1 | ENST00000 605920 | 1367 | 647 | UGUGAUCAAUC GGCUUGUU | Pm0f00ff00ff0 0fff0f0 | ooooooooo ooosssssso |
| lncFAM22E1 16 | LNC FAM22E1 | ENST00000 605920 | 1368 | 648 | UUGUGAUCAAU CGGCUUGU | Pmf0f00ff00ff0 0fff00 | ooooooooo ooosssssso |
| lncFAM22E1 17 | LNC FAM22E1 | ENST00000 605920 | 1369 | 649 | UAUGUGAUCAA UCGGCUUG | Pm0f0f00ff00ff 00fff0 | ooooooooo ooosssssso |
| lncFAM22E1 18 | LNC FAM22E1 | ENST00000 605920 | 1562 | 650 | UAGCCAUAAGG GUAAGGGA | Pm00ff0f0m00 0f000m00 | ooooooooo ooosssssso |
| lncFAM22E1 19 | LNC FAM22E1 | ENST00000 605920 | 1563 | 651 | UUAGCCAUAAG GGUAAGGG | Pmf00ff0f000 m0f000m0 | ooooooooo ooosssssso |
| lncFAM22E1 20 | LNC FAM22E1 | ENST00000 605920 | 1564 | 652 | UUUAGCCAUAA GGGUAAGG | Pmff00ff0f00m 00f00m0 | ooooooooo ooosssssso |
| lncFAM22E1 21 | LNC FAM22E1 | ENST00000 605920 | 1140 | 653 | UCGAUUUAAGG CUGGUAUC | Pmf00fff0m00f f00f0f0 | ooooooooo ooosssssso |
| lncFAM22E1 22 | LNC FAM22E1 | ENST00000 605920 | 1565 | 654 | UUUUAGCCAUA AGGGUAAG | Pmfff00ff0f0m 000f000 | ooooooooo ooosssssso |
| lncFAM22E1 23 | LNC FAM22E1 | ENST00000 605920 | 507 | 655 | UGAAUACCUCU AGUUCUUC | Pm000f0fffff00 fffff0 | ooooooooo ooosssssso |
| lncFAM22E1 24 | LNC FAM22E1 | ENST00000 605920 | 508 | 656 | UGGAAUACCUC UAGUUCUU | Pm00m0f0fffff 00ffff0 | ooooooooo ooosssssso |
| lncFAM22E1 25 | LNC FAM22E1 | ENST00000 605920 | 1141 | 657 | UUCGAUUUAAG GCUGGUAU | Pmff00fff0m00 ff00f00 | ooooooooo ooosssssso |
| lncFAM22E1 26 | LNC FAM22E1 | ENST00000 605920 | 1142 | 658 | UCUCGAUUUAA GGCUGGUA | Pmfff00fff00m 0ff00f0 | ooooooooo ooosssssso |
| lncFAM22E1 27 | LNC FAM22E1 | ENST00000 605920 | 1370 | 659 | UAAUGUGAUCA AUCGGCUU | Pm00f0f00ff00 ff00ff0 | ooooooooo ooosssssso |
| lncFAM22E1 28 | LNC FAM22E1 | ENST00000 605920 | 1389 | 660 | UUGCACUGCUA GAGCUGAA | Pmf0f0ff0ff0m 00ff000 | ooooooooo ooosssssso |
| lncFAM22E1 29 | LNC FAM22E1 | ENST00000 605920 | 1390 | 661 | UUUGCACUGCU AGAGCUGA | Pmff0f0ff0ff0ffm 000ff00 | ooooooooo ooosssssso |
| lncFAM22E1 30 | LNC FAM22E1 | ENST00000 605920 | 1492 | 662 | UUGCUGUCAUA AGAUCAAA | Pm0ff0ff0f0m 00ff000 | ooooooooo ooosssssso |

Table 2 Legend:
o: phosphodiester
s: phosphorothioate
P: 5' phosphorylation
0: 2'-OH
f: 2'-fluoro
m: 2' O-methyl

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Publication No. WO2010/033247 (Application No. PCT/US2009/005247), filed on Sep. 22, 2009, and entitled "REDUCED SIZE SELF-DELIVERING RNAI COMPOUNDS," U.S. Pat. No. 8,796,443, issued on Aug. 5, 2014, published as US 2012/0040459 on Feb. 16, 2012, entitled "REDUCED SIZE SELF-DELIVERING RNAI COMPOUNDS," PCT Publication No. WO2009/102427 (Application No. PCT/US2009/000852), filed on Feb. 11, 2009, and entitled, "MODIFIED RNAI POLYNUCLE-OTIDES AND USES THEREOF," and US Patent Publication No. 2011/0039914, published on Feb. 17, 2011 and entitled "MODIFIED RNAI POLYNUCLEOTIDES AND USES THEREOF," PCT Publication No. WO 2011/119887 (Application No. PCT/US2011/029867), filed on Mar. 24, 2011, and entitled RNA INTERFERENCE IN DERMAL AND FIBROTIC INDICATIONS, and U.S. Pat. No. 8,664, 189, issued on Mar. 4, 2014, published as US 2011/0237648 on Sep. 29, 2011, entitled "RNA INTERFERENCE IN DERMAL AND FIBROTIC INDICATIONS."

The invention claimed is:

1. An isolated, double stranded nucleic acid molecule comprising a guide strand of 18-23 nucleotides in length that has complementarity to a lncRNA sequence, and a passenger strand of 8-16 nucleotides in length, wherein the molecule comprises a double stranded region and a single stranded region, wherein the single stranded region is the 3' end of the guide strand, is 2-13 nucleotides in length, and comprises at least two phosphorothioate modifications, wherein at least 50% of the pyrimidines in the nucleic acid molecule are modified,
   wherein the isolated double stranded nucleic acid molecule is an lncRNA inhibitor of the lncRNA MALAT1; and
   wherein the double stranded nucleic acid molecule comprises at least 12 contiguous nucleotides of a sequence selected from SEQ ID NOs: 287, 288, 293, 295, 299, 617, 618, 623, 625, and 629.

2. The nucleic acid molecule of claim 1, wherein the first nucleotide relative to the 5'end of the guide strand has a 2'-O-methyl modification, optionally wherein the 2'-O-methyl modification is a 5P-2'-O-methyl U modification, or a 5' vinyl phosphonate 2'-O-methyl U modification.

3. The nucleic acid molecule of claim 1, wherein at least 60%, at least 80%, at least 90% or wherein 100% of the pyrimidines in the nucleic acid molecule are modified.

4. The nucleic acid molecule of claim 1, wherein at least one U or C includes a hydrophobic modification, optionally wherein a plurality of U's and/or C's include a hydrophobic modification, optionally wherein the hydrophobic modification is a methyl or ethyl hydrophobic base modification.

5. The nucleic acid molecule of claim 1, wherein the guide strand comprises:

(i) 6-8 phosphorothioate modifications;
(ii) 4-14 phosphorothioate modifications; or,
(iii) at least eight phosphorothioate modifications located within the first 10 nucleotides relative to the 3'end of the guide strand.

6. The nucleic acid molecule of claim 1, wherein the single stranded region of the guide strand is 6 nucleotides long to 8 nucleotides long.

7. The nucleic acid molecule of claim 1, wherein the double stranded region is 13 nucleotides long and/or wherein the double stranded nucleic acid molecule has one end that is blunt or includes a one nucleotide overhang.

8. The nucleic acid molecule of claim 1, wherein the passenger strand is linked at the 3' end to a lipophilic group.

9. The nucleic acid molecule of claim 8, wherein the lipophilic group is a sterol, optionally wherein the sterol is cholesterol.

10. The nucleic acid molecule of claim 1, wherein the guide strand is at least 50% chemically modified.

11. A method for modulating lncRNA expression and/or activity in a cell, comprising contacting a cell with the nucleic acid molecule of claim 1 in an amount effective to modulate lncRNA expression and/or activity in the cell.

12. The method of claim 11, wherein the lncRNA is localized in the nucleus of the cell.

13. The method of claim 11, wherein the cell is a bacterial cell or a eukaryotic cell.

14. The method of claim 13, wherein the cell is a mammalian cell.

15. The method of claim 11, wherein the cell is contacted with the isolated nucleic acid molecule in vivo or ex vivo.

16. A method of delivering a nucleic acid molecule to a cell, the method comprising administering an isolated nucleic acid molecule to a cell, wherein the isolated nucleic acid molecule comprises a guide strand that has complementarity to a lncRNA sequence and a passenger a strand, wherein the passenger strand is between 8-15 nucleotides in length and comprises at least two phosphorothioate modifications, wherein at least 50% of the pyrimidines in the passenger strand are modified, wherein the molecule comprises a hydrophobic conjugate;
wherein the isolated double stranded nucleic acid molecule is an lncRNA inhibitor of the lncRNA MALAT1; and
wherein the double stranded nucleic acid molecule comprises at least 12 contiguous nucleotides of a sequence selected from SEQ ID NOs: 287, 288, 293, 295, 299, 617, 618, 623, 625, and 629.

17. The method of claim 11, wherein the lncRNA is localized in the cytoplasm of the cell.

18. The method of claim 11, wherein the lncRNA is localized both in the nucleus and the cytoplasm of the cell.

19. The method of claim 14, wherein the mammalian cell is a mammalian stem cell.

\* \* \* \* \*

SEQUENCE LISTING

```
<160> NUMBER OF SEQ ID NOS: 662

<210> SEQ ID NO 1
<211> LENGTH: 672
<212> TYPE: DNA
<213> ORGANISM: Homo sapiens

<400> SEQUENCE: 1
ggaatagcgt catcagttct ataagagagc gtgtgccgaa ggcctcggcc tttcacattc      60
gggaagcgtc gggattaggt gaaagtacgt agttgtcttt cgtaagttaa aatgataatt     120
gggccgaaac ttactgcctt acctaaaagg cagcgcagtc aggatattgg taggtcgggg     180
gcggctttgg aaaccctthaa gtttacaagc atgcgcggac ttgagtgctc attaggtcgc     240
cgggcgtcca cgtgcagccc tggaccctga acccggcgt gcgtgggccg tgggccctcg      300
gggaaaggtt ccgtgcactc ggggactccg gtgaagcctg ttcagccgtc tgtgtcatgt     360
ggccatcttg agtctactct gtcgctcttg tgccctagca ccccgagaac cgtcagtttg     420
agccagatgg aagctgagct gaacacatta cgatggatga tggaaacata agactatcaa     480
gaaatccaag tggtaatggg cgaagtttat tcagcatccg gcaatggact tatcgtagtt     540
ggggaaacgg gtgttccgaa taatatcctg gaagttatca ggacacctat tttaaatata     600
ggcctgaatt ttgtaaagta atatttaagg tggtccgtga taattaaata aaatgcttaa     660
ttcatgtggc ta                                                         672

<210> SEQ ID NO 2
<211> LENGTH: 8708
<212> TYPE: DNA
<213> ORGANISM: Homo sapiens

<400> SEQUENCE: 2
gtaaaggact ggggccccgc aactggcctc tcctgccctc ttaagcgcag cgccatttta      60
gcaacgcaga agcccggcgc cgggaagcct cagctcgcct gaaggcaggt cccctctgac     120
gcctccggga gcccaggttt cccagagtcc ttgggacgca gcgacgagtt gtgctgctat     180
cttagctgtc cttataggct ggccattcca ggtggtggta tttagataaa accactcaaa     240
ctctgcagtt tggtcttggg gtttggagga aagcttttat ttttcttcct gctccggttc     300
agaaggtctg aagctcatac ctaaccaggc ataacacaga atctgcaaaa caaaaacccc     360
taaaaaagca gacccagagc agtgtaaaca cttctgggtg tgtccctgac tggctgccca     420
aggtctctgt gtcttcggag acaaagccat tcgcttagtt ggtctacttt aaaaggccac     480
```

```
ttgaactcgc tttccatggc gatttgcctt gtgagcactt tcaggagagc ctggaagctg    540
aaaaacggta gaaaattttc cgtgcgggcc gtgggggggct ggcggcaact gggggggccgc   600 agatcagagt gggccactgg cagccaacgg cccccggggc tcaggcgggg agcagctctg    660
tggtgtggga ttgaggcgtt ttccaagagt gggttttcac gtttctaaga tttcccaagc    720
agacagcccg tgctgctccg atttctcgaa caaaaaagca aaacgtgtgg ctgtcttggg    780
agcaagtcgc aggactgcaa gcagttgggg gagaaagtcc gccattttgc cacttctcaa    840
ccgtccctgc aaggctgggg ctcagttgcg taatggaaag taaagccctg aactatcaca    900
ctttaatctt ccttcaaaag gtggtaaact atacctactg tccctcaaga gaacacaaga    960
agtgctttaa gaggtatttt aaaagttccg ggggttttgt gaggtgtttg atgacccgtt   1020
taaaatatga tttccatgtt tcttttgtct aaagtttgca gctcaaatct ttccacacgc   1080
tagtaattta agtatttctg catgtgtagt ttgcattcaa gttccataag ctgttaagaa   1140
aaatctagaa aagtaaaact agaaccctatt tttaaccgaa gaactacttt ttgcctccct   1200
cacaaaggcg gcggaaggtg atcgaattcc ggtgatgcga gttgttctcc gtctataaat   1260
acgcctcgcc cgagctgtgc ggtaggcatt gaggcagcca gcgcaggggc ttctgctgag   1320
ggggcaggcg gagcttgagg aaaccgcaga taagtttttt tctctttgaa agatagagat   1380
taatacaact acttaaaaaa tatagtcaat aggttactaa gatattgctt agcgttaagt   1440
ttttaacgta atttaatag cttaagattt taagagaaaa tatgaagact tagaagagta   1500
gcatgaggaa ggaaaagata aaaggtttct aaaacatgac ggaggttgag atgaagcttc   1560
ttcatggagt aaaaaatgta tttaaaagaa aattgagaga aaggactaca gagccccgaa   1620
ttaataccaa tagaagggca atgcttttag attaaaatga aggtgactta aacagcttaa   1680
agtttagttt aaaagttgta ggtgattaaa ataatttgaa ggcgatcttt taaaaagaga   1740
ttaaaccgaa ggtgattaaa agaccttgaa atccatgacg cagggagaat tgcgtcattt   1800
aaagcctagt taacgcattt actaaacgca gacgaaaatg gaaagattaa ttgggagtgg   1860
taggatgaaa caatttggag aagatagaag tttgaagtgg aaaactggaa gacagaagta   1920
cgggaaggcg aagaaaagaa tagagaagat agggaaatta aagataaaaa acatactttt   1980
agaagaaaaa agataaattt aaacctgaaa agtaggaagc agaagaaaaa agacaagcta   2040
ggaaacaaaa agctaagggc aaaatgtaca aacttagaag aaaattggaa gatagaaaca   2100
agatagaaaa tgaaaatatt gtcaagagtt tcagatagaa aatgaaaaac aagctaagac   2160
aagtattgga gaagtataga agatagaaaa atataaagcc aaaaattgga taaaatagca   2220
ctgaaaaaat gaggaaatta ttggtaacca atttatttta aaagcccatc aatttaattt   2280
ctggtggtgc agaagttaga aggtaaagct tgagaagatg agggtgttta cgtagaccag   2340
aaccaattta gaagaatact tgaagctaga aggggaagtt ggttaaaaat cacatcaaaa   2400
agctactaaa aggactggtg taatttaaaa aaaactaagg cagaaggctt ttggaagagt   2460
tagaagaatt tggaaggcct taaatatagt agcttagttt gaaaaatgtg aaggactttc   2520
gtaacggaag taattcaaga tcaagagtaa ttaccaactt aatgtttttg cattggactt   2580
tgagttaaga ttatttttta aatcctgagg actagcatta attgacagct gacccaggtg   2640
ctacacagaa gtggattcag tgaatctagg aagacagcag cagacaggat tccaggaacc   2700
agtgtttgat gaagctagga ctgaggcaa agcgagcaag cagcagttcg tggtgaagat   2760
aggaaaagag tccaggagcc agtgcgattt ggtgaaggaa gctaggaaga aggaaggagc   2820
gctaacgatt tggtggtgaa gctaggaaaa aggattccag gaaggagcga gtgcaatttg   2880
```

```
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgttttctg gaacttactt atggtaacct     3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt ttttttttta cacgaatttg aggaaaacca aatgaatttg atagccaaat    3300
tgagacaatt tcagcaaatc tgtaagcagt ttgtatgttt agttgggta  atgaagtatt    3360 tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttcttttc ccttaggtct gtctagaatc ctaaaggcaa     3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac ccccttaatc agactttaaa    3720
agtgcttaac ccccttaaact tgttattttt tacttgaagc attttgggat ggtcttaaca    3780
gggaagagag agggtggggg agaaaatgtt ttttctaag attttccaca gatgctatag     3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080
gggaggggca aatattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt ttcccccccag tttgaattgg aagctgggg  gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt ttttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt tttagtgta     4680 ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860
tttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
acggaatcta ccattttaaa gttaattgct tgtcaagcta taaccacaaa aataatgaat    5160
tgatgagaaa tacaatgaag aggcaatgtc catctcaaaa tactgctttt acaaaagcag    5220
```

| | |
|---|---|
| aataaaagcg aaaagaaatg aaaatgttac actacattaa tcctggaata aaagaagccg | 5280 |
| aaataaatga gagatgagtt gggatcaagt ggattgagga ggctgtgctg tgtgccaatg | 5340 |
| tttcgtttgc ctcagacagg tatctcttcg ttatcagaag agttgcttca tttcatctgg | 5400 |
| gagcagaaaa cagcaggcag ctgttaacag ataagtttaa cttgcatctg cagtattgca | 5460 |
| tgttagggat aagtgcttat ttttaagagc tgtggagttc ttaaatatca accatggcac | 5520 |
| tttctcctga cccctteect aggggatttc aggattgaga aatttttcca tcgagccttt | 5580 |
| ttaaaattgt aggacttgtt cctgtgggct tcagtgatgg gatagtacac ttcactcaga | 5640 |
| ggcatttgca tctttaaata atttcttaaa agcctctaaa gtgatcagtg ccttgatgcc | 5700 |
| aactaaggaa atttgtttag cattgaatct ctgaaggctc tatgaaagga atagcatgat | 5760 |
| gtgctgttag aatcagatgt tactgctaaa atttacatgt tgtgatgtaa attgtgtaga | 5820 |
| aaaccattaa atcattcaaa ataataaact atttttatta gagaatgtat acttttagaa | 5880 |
| agctgtctcc ttatttaaat aaaatagtgt ttgtctgtag ttcagtgttg gggcaatctt | 5940 |
| gggggggatt cttctctaat cttcagaaaa ctttgtctgc gaacactctt taatggacca | 6000 |
| gatcaggatt tgagcggaag aacgaatgta actttaaggc aggaaagaca aattttattc | 6060 |
| ttcataaagt gatgagcata taataattcc aggcacatgg caatagaggc cctctaaata | 6120 |
| aggaataaat aacctcttag acaggtggga gattatgatc agagtaaaag gtaattacac | 6180 |
| attttatttc cagaaagtca ggggtctata aattgacagt gattagagta atacttttc | 6240 |
| acatttccaa agtttgcatg ttaactttaa atgcttacaa tcttagagtg gtaggcaatg | 6300 |
| ttttacacta ttgaccttat ataggdaagg gagggggtgc ctgtgggtt ttaaagaatt | 6360 |
| ttcctttgca gaggcatttc atccttcatg aagccattca ggattttgaa ttgcatatga | 6420 |
| gtgcttggct cttccttctg ttctagtgag tgtatgagac cttgcagtga gtttatcagc | 6480 |
| atactcaaaa ttttttttcct ggaatttgga gggatgggag gagggggtgg ggcttacttg | 6540 |
| ttgtagcttt ttttttttttt acagacttca cagagaatgc agttgtcttg acttcaggtc | 6600 |
| tgtctgttct gttggcaagt aaatgcagta ctgttctgat cccgctgcta ttagaatgca | 6660 |
| ttgtgaaacg actggagtat gattaaaagt tgtgttcccc aatgcttgga gtagtgattg | 6720 |
| ttgaaggaaa aaatccagct gagtgataaa ggctgagtgt tgaggaaatt tctgcagttt | 6780 |
| taagcagtcg tatttgtgat tgaagctgag tacattttgc tggtgtattt ttaggtaaaa | 6840 |
| tgcttttttgt tcatttctgg tggtgggagg ggactgaagc ctttagtctt ttccagatgc | 6900 |
| aaccttaaaa tcagtgacaa gaaacattcc aaacaagcaa cagtcttcaa gaaattaaac | 6960 |
| tggcaagtgg aaatgtttaa acagttcagt gatctttagt gcattgttta tgtgtgggtt | 7020 |
| tctctctccc ctcccttggt cttaattctt acatgcagga acactcagca gacacacgta | 7080 |
| tgcgaagggc cagagaagcc agacccagta agaaaaaata gcctatttac tttaaataaa | 7140 |
| ccaaacattc cattttaaat gtggggattg ggaaccacta gttctttcag atggtattct | 7200 |
| tcagactata gaaggagctt ccagttgaat tcaccagtgg acaaaatgag gaaaacaggt | 7260 |
| gaacaagctt tttctgtatt tacatacaaa gtcagatcag ttatgggaca atagtattga | 7320 |
| atagatttca gctttatgct ggagtaactg gcatgtgagc aaactgtgtt ggcgtggggg | 7380 |
| tggaggggtg aggtgggcgc taagccttt tttaagattt ttcaggtacc cctcactaaa | 7440 |
| ggcaccgaag gcttaaagta ggacaaccat ggagccttcc tgtggcagga gagacaacaa | 7500 |
| agcgctatta tcctaaggtc aagagaagtg tcagcctcac ctgatttta ttagtaatga | 7560 |
| ggacttgcct caactccctc tttctggagt gaagcatccg aaggaatgct tgaagtaccc | 7620 |

-continued

```
ctgggcttct cttaacattt aagcaagctg tttttatagc agctcttaat aataaagccc    7680
aaatctcaag cggtgcttga aggggaggga aaggggaaa gcgggcaacc acttttccct    7740
agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatccataa tcggtttcaa ggtaacgatg gtgtcgaggt    7920 cttttggtggg ttgaactatg ttagaaaagg ccattaattt gcctgcaaat tgttaacaga    7980
agggtattaa aaccacagct aagtagctct attataatac ttatccagtg actaaaacca    8040
acttaaacca gtaagtggag aaataacatg ttcaagaact gtaatgctgg gtgggaacat    8100
gtaacttgta gactggagaa gataggcatt tgagtggctg agagggcttt tgggtgggaa    8160
tgcaaaaatt ctctgctaag acttttttcag gtgaacataa cagacttggc caagctagca    8220
tcttagcgga agctgatctc caatgctctt cagtagggtc atgaaggttt ttcttttcct    8280
gagaaaacaa cacgtattgt tttctcaggt tttgctttt ggccttttc tagcttaaaa    8340 aaaaaaaag caaagatgc tggtggttgg cactcctggt ttccaggacg gggttcaaat    8400
ccctgcggcg tctttgcttt gactactaat ctgtcttcag gactcttct gtatttctcc    8460 ttttctctgc aggtgctagt tcttggagtt ttggggaggt gggaggtaac agcacaatat    8520
ctttgaacta tatacatcct tgatgtataa tttgtcagga gcttgacttg attgtatatt    8580
catatttaca cgagaaccta ataactgc cttgtctttt tcaggtaata gcctgcagct    8640
ggtgttttga aagccctac tgctgaaaac ttaacaattt tgtgtaataa aatggagaa    8700 gctctaaa                                                              8708
```

<210> SEQ ID NO 3
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 3
ccgcuucaga auca                                                         14

<210> SEQ ID NO 4
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 4
ugaucccgag ccua                                                         14

<210> SEQ ID NO 5
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 5
uuuuuccgcu guaa                                                         14

<210> SEQ ID NO 6
<211> LENGTH: 14
<212> TYPE: RNA

-continued

```
<213> ORGANISM: Artificial Sequence
<220> FEATURE:
<223> OTHER INFORMATION: Synthetic Polynucleotide

<400> SEQUENCE: 6
uuuuccgcug uaaa                                                       14

<210> SEQ ID NO 7
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 7
uuuccgcugu aaaa                                                       14

<210> SEQ ID NO 8
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 8
uuccgcugua aaua                                                       14

<210> SEQ ID NO 9
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 9
uccgcuguaa auaa                                                       14

<210> SEQ ID NO 10
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 10
gccaagcgga auua                                                       14

<210> SEQ ID NO 11
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 11
ccaagcggaa uuua                                                       14

<210> SEQ ID NO 12
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 12
caagcggaau uuaa                                                       14
```

```
<210> SEQ ID NO 13
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 13
aagcggaauu uaaa                                                           14

<210> SEQ ID NO 14
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 14
agcggaauuu aaaa                                                           14

<210> SEQ ID NO 15
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 15
gcggaauuua aaua                                                           14

<210> SEQ ID NO 16
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 16
ugagccgcag agaa                                                           14

<210> SEQ ID NO 17
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 17
agccgcagag auca                                                           14

<210> SEQ ID NO 18
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 18
uaccacguca guca                                                           14

<210> SEQ ID NO 19
<211> LENGTH: 14
<212> TYPE: RNA
<213> ORGANISM: Artificial Sequence
<220> FEATURE:
```

<223> OTHER INFORMATION: Synthetic Polynucleotide

<400> SEQUENCE: 19
accacgucag ucua                                                         14

<210> SEQ ID NO 20
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 20
acgagcuuaa caca                                                         14

<210> SEQ ID NO 21
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 21
cgagcuuaac acga                                                         14

<210> SEQ ID NO 22
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 22
gagcuuaaca cgca                                                         14

<210> SEQ ID NO 23
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 23
ccuuucgaau gcaa                                                         14

<210> SEQ ID NO 24
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 24
uucgaaugca cuua                                                         14

<210> SEQ ID NO 25
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 25
ucaagucgac guca                                                         14

```
<210> SEQ ID NO 26
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 26
aggccccgaa cuua                                                        14

<210> SEQ ID NO 27
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 27
ccaucguuac aaua                                                        14

<210> SEQ ID NO 28
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 28
auccuuucga auga                                                        14

<210> SEQ ID NO 29
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 29
ggcccauacc cuaa                                                        14

<210> SEQ ID NO 30
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 30
uauagacccu gaaa                                                        14

<210> SEQ ID NO 31
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 31
uagugcuauc acaa                                                        14

<210> SEQ ID NO 32
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 32
guugaccacu gcaa                                                   14

<210> SEQ ID NO 33
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 33
ucugcccgaa ucua                                                   14

<210> SEQ ID NO 34
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 34
ugcccgaauc uuca                                                   14

<210> SEQ ID NO 35
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 35
ccgaaucuuc acaa                                                   14

<210> SEQ ID NO 36
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 36
aauucgaccc guaa                                                   14

<210> SEQ ID NO 37
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 37
ucgacccgua acaa                                                   14

<210> SEQ ID NO 38
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 38
acccguaaca gcua                                                   14

<210> SEQ ID NO 39
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 39
uccgaugugc uuca                                                        14

<210> SEQ ID NO 40
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 40
acggaccuuu auua                                                        14

<210> SEQ ID NO 41
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 41
ucuccgaaga gaua                                                        14

<210> SEQ ID NO 42
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 42
uccgaagaga uuca                                                        14

<210> SEQ ID NO 43
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 43
ccgaagagau ucca                                                        14

<210> SEQ ID NO 44
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 44
agccgauuag cuga                                                        14

<210> SEQ ID NO 45
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 45
```
cuuaucgcca caca                                                         14

<210> SEQ ID NO 46
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 46
uggacguuug aaaa                                                         14

<210> SEQ ID NO 47
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 47
ggacguuuga aaaa                                                         14

<210> SEQ ID NO 48
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 48
uaggccuaau caaa                                                         14

<210> SEQ ID NO 49
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 49
ccuaaucaac guaa                                                         14

<210> SEQ ID NO 50
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 50
uucccgucuu uaua                                                         14

<210> SEQ ID NO 51
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 51
acacaagcuu auca                                                         14

<210> SEQ ID NO 52
<211> LENGTH: 14
<212> TYPE: RNA
<213> ORGANISM: Artificial Sequence

```
<220> FEATURE:
<223> OTHER INFORMATION: Synthetic Polynucleotide

<400> SEQUENCE: 52
cacaagcuua ucga                                                      14

<210> SEQ ID NO 53
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 53
cucacccuaa cuua                                                      14

<210> SEQ ID NO 54
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 54
ccuaacuuga ugga                                                      14

<210> SEQ ID NO 55
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 55
aucaacguaa auca                                                      14

<210> SEQ ID NO 56
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 56
acguaaaucu guca                                                      14

<210> SEQ ID NO 57
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 57
cuaacuugau ggaa                                                      14

<210> SEQ ID NO 58
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 58
aguuaggccu aaua                                                      14
```

```
<210> SEQ ID NO 59
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 59
guguaaggac ugca                                                      14

<210> SEQ ID NO 60
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 60
cgucuuuaua agga                                                      14

<210> SEQ ID NO 61
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 61
ccuggauuac aaga                                                      14

<210> SEQ ID NO 62
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 62
gaguuaggcc uaaa                                                      14

<210> SEQ ID NO 63
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 63
auuggagcuc aaca                                                      14

<210> SEQ ID NO 64
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 64
uggagcucaa cuaa                                                      14

<210> SEQ ID NO 65
<211> LENGTH: 14
<212> TYPE: RNA
<213> ORGANISM: Artificial Sequence
<220> FEATURE:
<223> OTHER INFORMATION: Synthetic Polynucleotide
```

-continued

<400> SEQUENCE: 65
agcucaacua ccga                                                    14

<210> SEQ ID NO 66
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 66
accgacugug ucaa                                                    14

<210> SEQ ID NO 67
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 67
gacuguguca auca                                                    14

<210> SEQ ID NO 68
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 68
aguaucaggu ucca                                                    14

<210> SEQ ID NO 69
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 69
ggucuauagu cuua                                                    14

<210> SEQ ID NO 70
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 70
cuuguauccg uaaa                                                    14

<210> SEQ ID NO 71
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 71
guauccguaa guca                                                    14

<210> SEQ ID NO 72

-continued

```
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 72
uccguaaguc acaa                                                       14

<210> SEQ ID NO 73
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 73
cguaagucac acaa                                                       14

<210> SEQ ID NO 74
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 74
aaaugucgaa aaga                                                       14

<210> SEQ ID NO 75
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 75
ugcaggucua uaga                                                       14

<210> SEQ ID NO 76
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 76
aggucuauag ucua                                                       14

<210> SEQ ID NO 77
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 77
aggauuauau gcca                                                       14

<210> SEQ ID NO 78
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 78
```
agacaauacc agaa                                                    14

<210> SEQ ID NO 79
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 79
ucuauagucu uuaa                                                    14

<210> SEQ ID NO 80
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 80
accaggauua uaua                                                    14

<210> SEQ ID NO 81
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 81
aguaauagcu gcaa                                                    14

<210> SEQ ID NO 82
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 82
gcauaaccuu gaga                                                    14

<210> SEQ ID NO 83
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 83
gcagacaaua ccaa                                                    14

<210> SEQ ID NO 84
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 84
gauacugacu gaga                                                    14

<210> SEQ ID NO 85
<211> LENGTH: 14
<212> TYPE: RNA

```
<213> ORGANISM: Artificial Sequence
<220> FEATURE:
<223> OTHER INFORMATION: Synthetic Polynucleotide

<400> SEQUENCE: 85
ugagucuuau guca                                                      14

<210> SEQ ID NO 86
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 86
auagucuuua cuca                                                      14

<210> SEQ ID NO 87
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 87
cuuggcagac aaua                                                      14

<210> SEQ ID NO 88
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 88
agguuccugu gcua                                                      14

<210> SEQ ID NO 89
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 89
aagccucuau ugua                                                      14

<210> SEQ ID NO 90
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 90
ccaaauguua ggaa                                                      14

<210> SEQ ID NO 91
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 91
aggauguaga agua                                                      14
```

<210> SEQ ID NO 92
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 92
caaagcaucu ccaa                                                      14

<210> SEQ ID NO 93
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 93
uggcgacuuu ugua                                                      14

<210> SEQ ID NO 94
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 94
gcgacuuuug uaua                                                      14

<210> SEQ ID NO 95
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 95
uaaagacgga ugaa                                                      14

<210> SEQ ID NO 96
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 96
uaaagacgaa uaua                                                      14

<210> SEQ ID NO 97
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 97
agacgaauau gcua                                                      14

<210> SEQ ID NO 98
<211> LENGTH: 14
<212> TYPE: RNA
<213> ORGANISM: Artificial Sequence
<220> FEATURE:

<223> OTHER INFORMATION: Synthetic Polynucleotide

<400> SEQUENCE: 98
aggaaucguc aaca                                                         14

<210> SEQ ID NO 99
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 99
aaucgucaac auca                                                         14

<210> SEQ ID NO 100
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 100
aucgucaaca ucua                                                         14

<210> SEQ ID NO 101
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 101
ucgucaacau cuua                                                         14

<210> SEQ ID NO 102
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 102
gaagccguug caga                                                         14

<210> SEQ ID NO 103
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 103
ccguggaauu guga                                                         14

<210> SEQ ID NO 104
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 104
caauuucgaa agga                                                         14

<210> SEQ ID NO 105
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 105
auuucgaaag guua                                                            14

<210> SEQ ID NO 106
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 106
uucgaaaggu ucca                                                            14

<210> SEQ ID NO 107
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 107
ugcucggcuu uuua                                                            14

<210> SEQ ID NO 108
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 108
acaucguucu cuua                                                            14

<210> SEQ ID NO 109
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 109
cguaaugguc ccaa                                                            14

<210> SEQ ID NO 110
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 110
ugcuccgugg aaua                                                            14

<210> SEQ ID NO 111
<211> LENGTH: 14
<212> TYPE: RNA
<213> ORGANISM: Artificial Sequence
<220> FEATURE:
<223> OTHER INFORMATION: Synthetic Polynucleotide

```
<400> SEQUENCE: 111
acggaugauu guca                                                    14

<210> SEQ ID NO 112
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 112
guaccagagg ugaa                                                    14

<210> SEQ ID NO 113
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 113
guaauggucc caga                                                    14

<210> SEQ ID NO 114
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 114
ugacugguac agaa                                                    14

<210> SEQ ID NO 115
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 115
aguaagacuc acaa                                                    14

<210> SEQ ID NO 116
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 116
gagguccaag cuua                                                    14

<210> SEQ ID NO 117
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 117
uguaggccuu ugua                                                    14

<210> SEQ ID NO 118
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 118
gcccauguau cuga                                                    14

<210> SEQ ID NO 119
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 119
cugaugacuu gaga                                                    14

<210> SEQ ID NO 120
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 120
ucugguaagu ucaa                                                    14

<210> SEQ ID NO 121
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 121
uaauaacccc uuua                                                    14

<210> SEQ ID NO 122
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 122
aauaaccccu uuga                                                    14

<210> SEQ ID NO 123
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 123
gccgacguau gaua                                                    14

<210> SEQ ID NO 124
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 124
```
cgacguauga uaaa					14

<210> SEQ ID NO 125
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 125
auacguccac guua					14

<210> SEQ ID NO 126
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 126
uagucccgau uuua					14

<210> SEQ ID NO 127
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 127
uauagcggac aaaa					14

<210> SEQ ID NO 128
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 128
uagcggacaa acua					14

<210> SEQ ID NO 129
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 129
uauaagcgga caua					14

<210> SEQ ID NO 130
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 130
uaagcggaca uaga					14

<210> SEQ ID NO 131
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 131
gcggacauag gaga                                                        14

<210> SEQ ID NO 132
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 132
gucuagucga ugua                                                        14

<210> SEQ ID NO 133
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 133
ucuagucgau guua                                                        14

<210> SEQ ID NO 134
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 134
cuagucgaug uuaa                                                        14

<210> SEQ ID NO 135
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 135
uagaggcgug uuga                                                        14

<210> SEQ ID NO 136
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 136
gcugucggaa gaga                                                        14

<210> SEQ ID NO 137
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 137
ugucggaaga gaga                                                        14

```
<210> SEQ ID NO 138
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 138
acuggccguu uaua                                                     14

<210> SEQ ID NO 139
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 139
ggccguuuau ggaa                                                     14

<210> SEQ ID NO 140
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 140
ccacguuugu uaaa                                                     14

<210> SEQ ID NO 141
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 141
uaugcuagac ugga                                                     14

<210> SEQ ID NO 142
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 142
cagcgaggca agaa                                                     14

<210> SEQ ID NO 143
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 143
cagacgaguc cuaa                                                     14

<210> SEQ ID NO 144
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 144
ugcccgaugu auga                                                       14

<210> SEQ ID NO 145
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 145
aauucguagg aaaa                                                       14

<210> SEQ ID NO 146
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 146
aacaccccuc uaaa                                                       14

<210> SEQ ID NO 147
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 147
agcgaaugca gaca                                                       14

<210> SEQ ID NO 148
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 148
ggucuaacca uuga                                                       14

<210> SEQ ID NO 149
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 149
ucuagacgau ggua                                                       14

<210> SEQ ID NO 150
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 150
acgaugguuu uaga                                                       14

<210> SEQ ID NO 151
```

```
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 151
gagcguuuuu agua                                                            14

<210> SEQ ID NO 152
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 152
agcuuuacga auga                                                            14

<210> SEQ ID NO 153
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 153
ccgcuaagag auaa                                                            14

<210> SEQ ID NO 154
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 154
aauucgauga gcga                                                            14

<210> SEQ ID NO 155
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 155
auucgaugag cgca                                                            14

<210> SEQ ID NO 156
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 156
uucgaugagc gcga                                                            14

<210> SEQ ID NO 157
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 157
```
aacguucgac aaga                                                    14

<210> SEQ ID NO 158
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 158
cguucgacaa ggaa                                                    14

<210> SEQ ID NO 159
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 159
uucgacaagg acua                                                    14

<210> SEQ ID NO 160
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 160 acguuacgg caca                                                     14

<210> SEQ ID NO 161
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 161
aacggcacag caua                                                    14

<210> SEQ ID NO 162
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 162
uguagacgaa uaaa                                                    14

<210> SEQ ID NO 163
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 163
uuccaacgag ugga                                                    14

<210> SEQ ID NO 164
<211> LENGTH: 14
<212> TYPE: RNA

```
<213> ORGANISM: Artificial Sequence
<220> FEATURE:
<223> OTHER INFORMATION: Synthetic Polynucleotide

<400> SEQUENCE: 164
uuauaacgac auua                                                        14

<210> SEQ ID NO 165
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 165
auaacgacau ugca                                                        14

<210> SEQ ID NO 166
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 166
cgauuucgag aaaa                                                        14

<210> SEQ ID NO 167
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 167
uucgagaaau gaca                                                        14

<210> SEQ ID NO 168
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 168
ucucgaaugg cuca                                                        14

<210> SEQ ID NO 169
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 169
gaaccucgag uuaa                                                        14

<210> SEQ ID NO 170
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 170
ccucgaguua gaga                                                        14
```

```
<210> SEQ ID NO 171
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 171
cugcgaagau gcaa                                                        14

<210> SEQ ID NO 172
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 172
gcgaagaugc aaaa                                                        14

<210> SEQ ID NO 173
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 173
uuaugcuuag ugga                                                        14

<210> SEQ ID NO 174
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 174
gcuacacucc auga                                                        14

<210> SEQ ID NO 175
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 175
guaucaagga ccua                                                        14

<210> SEQ ID NO 176
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 176
augcccuauu gaaa                                                        14

<210> SEQ ID NO 177
<211> LENGTH: 14
<212> TYPE: RNA
<213> ORGANISM: Artificial Sequence
<220> FEATURE:
```

<223> OTHER INFORMATION: Synthetic Polynucleotide

<400> SEQUENCE: 177
aucccaacuu guaa                                                        14

<210> SEQ ID NO 178
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 178
acuaucgaaa uaaa                                                        14

<210> SEQ ID NO 179
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 179
cuuauaccag gaga                                                        14

<210> SEQ ID NO 180
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 180
cccuauugaa caua                                                        14

<210> SEQ ID NO 181
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 181
uaguaagaug gcua                                                        14

<210> SEQ ID NO 182
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 182
aacuuguagc ugca                                                        14

<210> SEQ ID NO 183
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 183
auaucgagua cuga                                                        14

```
<210> SEQ ID NO 184
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 184
uguacucgag aaaa                                                        14

<210> SEQ ID NO 185
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 185
ugcgauuugu ugga                                                        14

<210> SEQ ID NO 186
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 186
gcgauuuguu ggaa                                                        14

<210> SEQ ID NO 187
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 187
gcccucgacu acca                                                        14

<210> SEQ ID NO 188
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 188
ugacaacggc agaa                                                        14

<210> SEQ ID NO 189
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 189
gacaacggca gaga                                                        14

<210> SEQ ID NO 190
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 190
cguuuaccuu aga                                                      13

<210> SEQ ID NO 191
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 191
ccacucgaua acaa                                                     14

<210> SEQ ID NO 192
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 192
cacucgauaa caca                                                     14

<210> SEQ ID NO 193
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 193
acucgauaac acca                                                     14

<210> SEQ ID NO 194
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 194
ucgauaacac caaa                                                     14

<210> SEQ ID NO 195
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 195
aaugcgucca ucua                                                     14

<210> SEQ ID NO 196
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 196
augcguccau cuga                                                     14

<210> SEQ ID NO 197
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 197
ugcguccauc ugaa                                                    14

<210> SEQ ID NO 198
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 198
gcguccaucu gaaa                                                    14

<210> SEQ ID NO 199
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 199
uacucgagaa acua                                                    14

<210> SEQ ID NO 200
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 200
ucgagaaacu uuga                                                    14

<210> SEQ ID NO 201
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 201
acccauuacc uaca                                                    14

<210> SEQ ID NO 202
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 202
ggugccuaug agua                                                    14

<210> SEQ ID NO 203
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 203
```
ugccuaugag uaua                                                         14

<210> SEQ ID NO 204
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 204
cccguuuacc uuaa                                                         14

<210> SEQ ID NO 205
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 205
cuuggcgaaa guaa                                                         14

<210> SEQ ID NO 206
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 206
ggcgaaagua aaaa                                                         14

<210> SEQ ID NO 207
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 207
ucuuggacua gaga                                                         14

<210> SEQ ID NO 208
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 208
uggacuagag acaa                                                         14

<210> SEQ ID NO 209
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 209
aaguucgauu uuua                                                         14

<210> SEQ ID NO 210
<211> LENGTH: 14
<212> TYPE: RNA
<213> ORGANISM: Artificial Sequence

```
<220> FEATURE:
<223> OTHER INFORMATION: Synthetic Polynucleotide

<400> SEQUENCE: 210
ugauagguuu agca                                                             14

<210> SEQ ID NO 211
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 211
ccuuagugug cuua                                                             14

<210> SEQ ID NO 212
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 212
aguuggucca uuaa                                                             14

<210> SEQ ID NO 213
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 213
uuuauauguc guca                                                             14

<210> SEQ ID NO 214
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 214
uuauaugucg ucua                                                             14

<210> SEQ ID NO 215
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 215
cuuugucgua agua                                                             14

<210> SEQ ID NO 216
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 216
uuugucguaa guua                                                             14
```

```
<210> SEQ ID NO 217
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 217
uugucguaag uuaa                                                      14

<210> SEQ ID NO 218
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 218
ugucguaagu uaua                                                      14

<210> SEQ ID NO 219
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 219
gucguaaguu auga                                                      14

<210> SEQ ID NO 220
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 220
ugagagcguu guua                                                      14

<210> SEQ ID NO 221
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 221
agagcguugu uuaa                                                      14

<210> SEQ ID NO 222
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 222
gucuugcgac ugaa                                                      14

<210> SEQ ID NO 223
<211> LENGTH: 14
<212> TYPE: RNA
<213> ORGANISM: Artificial Sequence
<220> FEATURE:
<223> OTHER INFORMATION: Synthetic Polynucleotide
```

-continued

<400> SEQUENCE: 223
cuugcgacug auca                                                14

<210> SEQ ID NO 224
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 224
ugcgacugau cuua                                                14

<210> SEQ ID NO 225
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 225
uugcgacuga ucua                                                14

<210> SEQ ID NO 226
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 226
gcgacugauc uuca                                                14

<210> SEQ ID NO 227
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 227
ccuauccguu acua                                                14

<210> SEQ ID NO 228
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 228
uauccguuac ugaa                                                14

<210> SEQ ID NO 229
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 229
acucgauaac acca                                                14

<210> SEQ ID NO 230

```
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 230
gguagaucua gcua                                                        14

<210> SEQ ID NO 231
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 231
uagaucuagc uuca                                                        14

<210> SEQ ID NO 232
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 232
gaucuagcuu caua                                                        14

<210> SEQ ID NO 233
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 233
agguauccaa ucca                                                        14

<210> SEQ ID NO 234
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 234
uaagguaucc aaua                                                        14

<210> SEQ ID NO 235
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 235
gacuagcaua ggua                                                        14

<210> SEQ ID NO 236
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 236
```

-continued uagcauaggu cuga  14

<210> SEQ ID NO 237
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 237
gcauaggucu guua  14

<210> SEQ ID NO 238
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 238
agcguuguuu aaua  14

<210> SEQ ID NO 239
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 239
uccuauccgu uaca  14

<210> SEQ ID NO 240
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 240
auccguuacu gaaa  14

<210> SEQ ID NO 241
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 241
ccguuacuga aaga  14

<210> SEQ ID NO 242
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 242
uauaugucgu cuua  14

<210> SEQ ID NO 243
<211> LENGTH: 14
<212> TYPE: RNA

```
<213> ORGANISM: Artificial Sequence
<220> FEATURE:
<223> OTHER INFORMATION: Synthetic Polynucleotide

<400> SEQUENCE: 243
aaaguacgua guua                                                 14

<210> SEQ ID NO 244
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 244
aaguacguag uuga                                                 14

<210> SEQ ID NO 245
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 245
aguacguagu ugua                                                 14

<210> SEQ ID NO 246
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 246
uacguaguug ucua                                                 14

<210> SEQ ID NO 247
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 247
acauuacgau ggaa                                                 14

<210> SEQ ID NO 248
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 248
cauuacgaug gaua                                                 14

<210> SEQ ID NO 249
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 249
auuacgaugg auga                                                 14
```

<210> SEQ ID NO 250
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 250
uuacgaugga ugaa                                                        14

<210> SEQ ID NO 251
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 251
uacgauggau gaua                                                        14

<210> SEQ ID NO 252
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 252
acgauggaug auga                                                        14

<210> SEQ ID NO 253
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 253
agcauccggc aaua                                                        14

<210> SEQ ID NO 254
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 254
acuuaucgua guua                                                        14

<210> SEQ ID NO 255
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 255
cuuaucguag uuga                                                        14

<210> SEQ ID NO 256
<211> LENGTH: 14
<212> TYPE: RNA
<213> ORGANISM: Artificial Sequence
<220> FEATURE:

<223> OTHER INFORMATION: Synthetic Polynucleotide

<400> SEQUENCE: 256
gugguccgug auaa                                                         14

<210> SEQ ID NO 257
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 257
ugguccguga uaaa                                                         14

<210> SEQ ID NO 258
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 258
gguccgugau aaua                                                         14

<210> SEQ ID NO 259
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 259
guccgugaua auua                                                         14

<210> SEQ ID NO 260
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 260
uccgugauaa uuaa                                                         14

<210> SEQ ID NO 261
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 261
ucuuucguaa guua                                                         14

<210> SEQ ID NO 262
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 262
cuuucguaag uuaa                                                         14

```
<210> SEQ ID NO 263
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 263
ggcaauggac uuaa                                                         14

<210> SEQ ID NO 264
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 264
uccgaauaau auca                                                         14

<210> SEQ ID NO 265
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 265
ccgaauaaua ucca                                                         14

<210> SEQ ID NO 266
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 266
aggugguccg ugaa                                                         14

<210> SEQ ID NO 267
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 267
ggugguccgu gaua                                                         14

<210> SEQ ID NO 268
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 268
ccgugauaau uaaa                                                         14

<210> SEQ ID NO 269
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 269
ugccuuaccu aaaa                                                    14

<210> SEQ ID NO 270
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 270
gccuuaccua aaaa                                                    14

<210> SEQ ID NO 271
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 271
gcaauggacu uaua                                                    14

<210> SEQ ID NO 272
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 272
auggacuuau cgua                                                    14

<210> SEQ ID NO 273
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 273
uucgcuuagu ugga                                                    14

<210> SEQ ID NO 274
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 274
guugcguaau ggaa                                                    14

<210> SEQ ID NO 275
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 275
augacccguu uaaa                                                    14

<210> SEQ ID NO 276
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 276
ugacccguuu aaaa                                                         14

<210> SEQ ID NO 277
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 277
uaaacgcaga cgaa                                                         14

<210> SEQ ID NO 278
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 278
acgcagacga aaaa                                                         14

<210> SEQ ID NO 279
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 279
uucguaacgg aaga                                                         14

<210> SEQ ID NO 280
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 280
agcgcuaacg auua                                                         14

<210> SEQ ID NO 281
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 281
ucguacugag guga                                                         14

<210> SEQ ID NO 282
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 282
```

```
uaaucgguuu caaa                                              14

<210> SEQ ID NO 283
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 283
acgagaaccu aaua                                              14

<210> SEQ ID NO 284
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 284
cgaauuccgg ugaa                                              14

<210> SEQ ID NO 285
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 285
uaaauacgcc ucga                                              14

<210> SEQ ID NO 286
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 286
ucggcaauau guua                                              14

<210> SEQ ID NO 287
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 287
uuacggaauc uaca                                              14

<210> SEQ ID NO 288
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 288
ucguuugccu caga                                              14

<210> SEQ ID NO 289
<211> LENGTH: 14
<212> TYPE: RNA
<213> ORGANISM: Artificial Sequence
```

```
<220> FEATURE:
<223> OTHER INFORMATION: Synthetic Polynucleotide

<400> SEQUENCE: 289
gucugcgaac acua                                                    14

<210> SEQ ID NO 290
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 290
agcggaagaa cgaa                                                    14

<210> SEQ ID NO 291
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 291
aucccgcugc uaua                                                    14

<210> SEQ ID NO 292
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 292
aacgacugga guaa                                                    14

<210> SEQ ID NO 293
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 293
gucguauuug ugaa                                                    14

<210> SEQ ID NO 294
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 294
accgaaggcu uaaa                                                    14

<210> SEQ ID NO 295
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 295
ucaagcggug cuua                                                    14
```

```
<210> SEQ ID NO 296
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 296
uagcggaagc ugaa                                                        14

<210> SEQ ID NO 297
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 297
ugaguaggcc aaaa                                                        14

<210> SEQ ID NO 298
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 298
acguagacca gaaa                                                        14

<210> SEQ ID NO 299
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 299
uucgugguga agaa                                                        14

<210> SEQ ID NO 300
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 300
cuuagcguua agua                                                        14

<210> SEQ ID NO 301
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 301
cccgaauuaa uaca                                                        14

<210> SEQ ID NO 302
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 302
aaguccgcca uuua                                                      14

<210> SEQ ID NO 303
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 303
uagagguauu ccca                                                      14

<210> SEQ ID NO 304
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 304
ccgugcgcuu uaua                                                      14

<210> SEQ ID NO 305
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 305
ccagccuuaa auca                                                      14

<210> SEQ ID NO 306
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 306
aaucgagccg acua                                                      14

<210> SEQ ID NO 307
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 307
aucgagccga cuaa                                                      14

<210> SEQ ID NO 308
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 308
ucgagccgac uaca                                                      14

<210> SEQ ID NO 309
```

```
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 309
gcuucagcgg aaua                                              14

<210> SEQ ID NO 310
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 310
gcggaauacc uaca                                              14

<210> SEQ ID NO 311
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 311
cggaauaccu acua                                              14

<210> SEQ ID NO 312
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 312
aacaagccga uuga                                              14

<210> SEQ ID NO 313
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 313
acaagccgau ugaa                                              14

<210> SEQ ID NO 314
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 314
caagccgauu gaua                                              14

<210> SEQ ID NO 315
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 315
```
aagccgauug auca                                                         14

<210> SEQ ID NO 316
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 316
agccgauuga ucaa                                                         14

<210> SEQ ID NO 317
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 317
gccgauugau caca                                                         14

<210> SEQ ID NO 318
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 318
ccgauugauc acaa                                                         14

<210> SEQ ID NO 319
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 319
cgauugauca caua                                                         14

<210> SEQ ID NO 320
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 320
uacccuuaug gcua                                                         14

<210> SEQ ID NO 321
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 321
acccuuaugg cuaa                                                         14

<210> SEQ ID NO 322
<211> LENGTH: 14
<212> TYPE: RNA

```
<213> ORGANISM: Artificial Sequence
<220> FEATURE:
<223> OTHER INFORMATION: Synthetic Polynucleotide

<400> SEQUENCE: 322
cccuuauggc uaaa                                                 14

<210> SEQ ID NO 323
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 323
cagccuuaaa ucga                                                 14

<210> SEQ ID NO 324
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 324
ccuuauggcu aaaa                                                 14

<210> SEQ ID NO 325
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 325
acuagaggua uuca                                                 14

<210> SEQ ID NO 326
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 326
cuagagguau ucca                                                 14

<210> SEQ ID NO 327
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 327
agccuuaaau cgaa                                                 14

<210> SEQ ID NO 328
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 328
gccuuaaauc gaga                                                 14
```

<210> SEQ ID NO 329
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 329
gauugaucac auua                                                      14

<210> SEQ ID NO 330
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 330
cucuagcagu gcaa                                                      14

<210> SEQ ID NO 331
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 331
ucuagcagug caaa                                                      14

<210> SEQ ID NO 332
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 332
ucuuaugaca gcaa                                                      14

<210> SEQ ID NO 333
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 333
ugauucugaa gcggaaccu                                                 19

<210> SEQ ID NO 334
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 334
uaggcucggg aucauguaa                                                 19

<210> SEQ ID NO 335
<211> LENGTH: 19
<212> TYPE: RNA
<213> ORGANISM: Artificial Sequence
<220> FEATURE:

```
<223> OTHER INFORMATION: Synthetic Polynucleotide

<400> SEQUENCE: 335
uuacagcgga aaaaggcag                                                   19

<210> SEQ ID NO 336
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 336
uuuacagcgg aaaaaggca                                                   19

<210> SEQ ID NO 337
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 337
uuuuacagcg gaaaaaggc                                                   19

<210> SEQ ID NO 338
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 338
uauuuacagc ggaaaaagg                                                   19

<210> SEQ ID NO 339
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 339
uuauuuacag cggaaaaag                                                   19

<210> SEQ ID NO 340
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 340
uaauuccgcu uggcaagaa                                                   19

<210> SEQ ID NO 341
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 341
uaaauuccgc uuggcaaga                                                   19
```

<210> SEQ ID NO 342
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 342
uuaaauuccg cuuggcaag                                        19

<210> SEQ ID NO 343
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 343
uuuaaauucc gcuuggcaa                                        19

<210> SEQ ID NO 344
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 344
uuuuaaauuc cgcuuggca                                        19

<210> SEQ ID NO 345
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 345
uauuuaaauu ccgcuuggc                                        19

<210> SEQ ID NO 346
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 346
uucucugcgg cucaaaugu                                        19

<210> SEQ ID NO 347
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 347
ugaucucugc ggcucaaau                                        19

<210> SEQ ID NO 348
<211> LENGTH: 19
<212> TYPE: RNA
<213> ORGANISM: Artificial Sequence
<220> FEATURE:
<223> OTHER INFORMATION: Synthetic Polynucleotide

```
<400> SEQUENCE: 348
ugacugacgu gguaggauu                                                    19

<210> SEQ ID NO 349
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 349
uagacugacg ugguaggau                                                    19

<210> SEQ ID NO 350
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 350
uguguuaagc ucguuuucc                                                    19

<210> SEQ ID NO 351
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 351
ucguguuaag cucguuuuc                                                    19

<210> SEQ ID NO 352
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 352
ugcguguuaa gcucguuuu                                                    19

<210> SEQ ID NO 353
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 353
uugcauucga aaggaucca                                                    19

<210> SEQ ID NO 354
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 354
uaagugcauu cgaaaggau                                                    19

<210> SEQ ID NO 355
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 355
ugacgucgac uugagaaag                                                19

<210> SEQ ID NO 356
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 356
uaaguucggg gccuacaaa                                                19

<210> SEQ ID NO 357
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 357
uauuguaacg auggagcug                                                19

<210> SEQ ID NO 358
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 358
ucauucgaaa ggauccauc                                                19

<210> SEQ ID NO 359
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 359
uuaggguaug ggccuaaau                                                19

<210> SEQ ID NO 360
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 360
uuucaggguc uauauaaga                                                19

<210> SEQ ID NO 361
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 361
```

```
uugugauagc acuacuaca                                                  19

<210> SEQ ID NO 362
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 362
uugcaguggu caacuugua                                                  19

<210> SEQ ID NO 363
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 363
uagauucggg cagagauug                                                  19

<210> SEQ ID NO 364
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 364
ugaagauucg ggcagagau                                                  19

<210> SEQ ID NO 365
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 365
uugugaagau cgggcaga                                                   19

<210> SEQ ID NO 366
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 366
uuacgggucg aauuguguc                                                  19

<210> SEQ ID NO 367
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 367
uuguuacggg ucgaauugu                                                  19

<210> SEQ ID NO 368
<211> LENGTH: 19
<212> TYPE: RNA
<213> ORGANISM: Artificial Sequence
```

<220> FEATURE:
<223> OTHER INFORMATION: Synthetic Polynucleotide

<400> SEQUENCE: 368
uagcuguuac gggucgaau                                                    19

<210> SEQ ID NO 369
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 369
ugaagcacau cggaugugu                                                    19

<210> SEQ ID NO 370
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 370
uaauaaaggu ccguggaaa                                                    19

<210> SEQ ID NO 371
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 371
uaucucuucg gagagaucc                                                    19

<210> SEQ ID NO 372
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 372
ugaaucucuu cggagagau                                                    19

<210> SEQ ID NO 373
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 373
uggaaucucu ucggagaga                                                    19

<210> SEQ ID NO 374
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 374
ucagcuaauc ggcuaugga                                                    19

```
<210> SEQ ID NO 375
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 375
uguguggcga uaagcuugu                                                    19

<210> SEQ ID NO 376
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 376
uuuucaaacg uccagcagc                                                    19

<210> SEQ ID NO 377
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 377
uuuuucaaac guccagcag                                                    19

<210> SEQ ID NO 378
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 378
uuugauuagg ccuaacuca                                                    19

<210> SEQ ID NO 379
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 379
uuacguugau uaggccuaa                                                    19

<210> SEQ ID NO 380
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 380
uauaaagacg ggaaauuug                                                    19

<210> SEQ ID NO 381
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 381
ugauaagcuu guguccauc                                                    19

<210> SEQ ID NO 382
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 382
ucgauaagcu uguguccau                                                    19

<210> SEQ ID NO 383
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 383
uaaguuaggg ugagucauc                                                    19

<210> SEQ ID NO 384
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 384
uccaucaagu uagggugag                                                    19

<210> SEQ ID NO 385
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 385
ugauuuacgu ugauuaggc                                                    19

<210> SEQ ID NO 386
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 386
ugacagauuu acguugauu                                                    19

<210> SEQ ID NO 387
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 387
uuccaucaag uuaggguga                                                    19

<210> SEQ ID NO 388

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 388
uauuaggccu aacucacag                                                  19

<210> SEQ ID NO 389
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 389
ugcaguccuu acacagagu                                                  19

<210> SEQ ID NO 390
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 390
uccuuauaaa gacgggaaa                                                  19

<210> SEQ ID NO 391
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 391
ucuuguaauc cagggccuu                                                  19

<210> SEQ ID NO 392
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 392
uuuaggccua acucacagg                                                  19

<210> SEQ ID NO 393
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 393
uguugagcuc caaugcuga                                                  19

<210> SEQ ID NO 394
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 394
```
uuaguugagc uccaaugcu                                              19

<210> SEQ ID NO 395
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 395
ucgguaguug agcuccaau                                              19

<210> SEQ ID NO 396
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 396
uugacacagu cgguaguug                                              19

<210> SEQ ID NO 397
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 397
ugauugacac agucgguag                                              19

<210> SEQ ID NO 398
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 398
uggaaccuga uacucuuau                                              19

<210> SEQ ID NO 399
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 399
uaagacuaua gaccugcau                                              19

<210> SEQ ID NO 400
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 400
uuuacggaua caagugcug                                              19

<210> SEQ ID NO 401
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 401
ugacuuacgg auacaagug                                              19

<210> SEQ ID NO 402
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 402
uugugacuua cggauacaa                                              19

<210> SEQ ID NO 403
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 403
uugugugacu uacggauac                                              19

<210> SEQ ID NO 404
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 404
ucuuuucgac auuuuccau                                              19

<210> SEQ ID NO 405
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 405
ucuauagacc ugcauuaaa                                              19

<210> SEQ ID NO 406
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 406
uagacuauag accugcauu                                              19

<210> SEQ ID NO 407
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 407
uggcauauaa uccuggugc                                              19
```

<210> SEQ ID NO 408
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 408
uucugguauu gucugccaa                                                    19

<210> SEQ ID NO 409
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 409
uuaaagacua uagaccugc                                                    19

<210> SEQ ID NO 410
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 410
uauauaaucc uggugccaa                                                    19

<210> SEQ ID NO 411
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 411
uugcagcuau uacuugucu                                                    19

<210> SEQ ID NO 412
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 412
ucucaagguu augcagcua                                                    19

<210> SEQ ID NO 413
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 413
uugguauugu cugccaaga                                                    19

<210> SEQ ID NO 414
<211> LENGTH: 19
<212> TYPE: RNA
<213> ORGANISM: Artificial Sequence
<220> FEATURE:

<223> OTHER INFORMATION: Synthetic Polynucleotide

<400> SEQUENCE: 414
ucucagucag uaucuugcu					19

<210> SEQ ID NO 415
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 415
ugacauaaga cucaauccu					19

<210> SEQ ID NO 416
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 416
ugaguaaaga cuauagacc					19

<210> SEQ ID NO 417
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 417
uauugucugc caagaugau					19

<210> SEQ ID NO 418
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 418
uagcacagga accugauac					19

<210> SEQ ID NO 419
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 419
uacaauagag gcuucauau					19

<210> SEQ ID NO 420
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 420
uuccuaacau uuggcacu					19

```
<210> SEQ ID NO 421
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 421
uacuucuaca uccuguugu                                                  19

<210> SEQ ID NO 422
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 422
uuggagaugc uuugcacac                                                  19

<210> SEQ ID NO 423
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 423
uacaaaaguc gccaggcau                                                  19

<210> SEQ ID NO 424
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 424
uauacaaaag ucgccaggc                                                  19

<210> SEQ ID NO 425
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 425
uucauccguc uuuaccagc                                                  19

<210> SEQ ID NO 426
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 426
uauauucguc uuuacuacc                                                  19

<210> SEQ ID NO 427
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 427
uagcauauuc gucuuuacu                                              19

<210> SEQ ID NO 428
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 428
uguugacgau uccugccau                                              19

<210> SEQ ID NO 429
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 429
ugauguugac gauuccugc                                              19

<210> SEQ ID NO 430
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 430
uagauguuga cgauuccug                                              19

<210> SEQ ID NO 431
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 431
uaagauguug acgauuccu                                              19

<210> SEQ ID NO 432
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 432
ucugcaacgg cuucuuugu                                              19

<210> SEQ ID NO 433
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 433
ucacaauucc acggagcaa                                              19

<210> SEQ ID NO 434
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 434
uccuuucgaa auugcucau                                                    19

<210> SEQ ID NO 435
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 435
uaaccuuucg aaauugcuc                                                    19

<210> SEQ ID NO 436
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 436
uggaaccuuu cgaaauugc                                                    19

<210> SEQ ID NO 437
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 437
uaaaaagccg agcacugga                                                    19

<210> SEQ ID NO 438
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 438
uaagagaacg auguuugug                                                    19

<210> SEQ ID NO 439
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 439
uugggaccau uacgugaaa                                                    19

<210> SEQ ID NO 440
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 440
```
uauuccacgg agcaagaga               19

<210> SEQ ID NO 441
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 441
ugacaaucau ccgucuuua               19

<210> SEQ ID NO 442
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 442
uucaccucug guacaucua               19

<210> SEQ ID NO 443
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 443
ucugggacca uuacgugaa               19

<210> SEQ ID NO 444
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 444
uucuguacca gucauagcc               19

<210> SEQ ID NO 445
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 445
uugugagucu uacugcaga               19

<210> SEQ ID NO 446
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 446
uaagcuugga ccucuaaga               19

<210> SEQ ID NO 447
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 447
uacaaaggcc uacaguaaa                                                    19

<210> SEQ ID NO 448
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 448
ucagauacau gggcgaaca                                                    19

<210> SEQ ID NO 449
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 449
ucucaaguca ucagacucu                                                    19

<210> SEQ ID NO 450
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 450
uugaacuuac cagagacuu                                                    19

<210> SEQ ID NO 451
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 451 uaaaggggu auuacaaaa                                                     19

<210> SEQ ID NO 452
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 452
ucaaaggggu uauuacaaa                                                    19

<210> SEQ ID NO 453
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 453
uaucauacgu cggcaaccu                                                    19
```

<210> SEQ ID NO 454
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 454
uuuaucauac gucggcaac                                              19

<210> SEQ ID NO 455
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 455
uaacguggac guaucgcuu                                              19

<210> SEQ ID NO 456
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 456
uaaaaucggg acuaauuug                                              19

<210> SEQ ID NO 457
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 457
uuuuguccgc uauauacac                                              19

<210> SEQ ID NO 458
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 458
uaguuugucc gcuauauac                                              19

<210> SEQ ID NO 459
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 459
uauguccgcu uauauacac                                              19

<210> SEQ ID NO 460
<211> LENGTH: 19
<212> TYPE: RNA
<213> ORGANISM: Artificial Sequence
<220> FEATURE:
<223> OTHER INFORMATION: Synthetic Polynucleotide

```
<400> SEQUENCE: 460
ucuauguccg cuuauauac                                          19

<210> SEQ ID NO 461
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 461
ucuccuaugu ccgcuuaua                                          19

<210> SEQ ID NO 462
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 462
uacaucgacu agacguaaa                                          19

<210> SEQ ID NO 463
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 463
uaacaucgac uagacguaa                                          19

<210> SEQ ID NO 464
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 464
uuaacaucga cuagacgua                                          19

<210> SEQ ID NO 465
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 465
ucaacacgcc ucuagauaa                                          19

<210> SEQ ID NO 466
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 466
ucucuuccga cagcaaagu                                          19

<210> SEQ ID NO 467
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 467
ucucucuucc gacagcaaa                                                    19

<210> SEQ ID NO 468
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 468
uauaaacggc caguaaauc                                                    19

<210> SEQ ID NO 469
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 469
uuccauaaac ggccaguaa                                                    19

<210> SEQ ID NO 470
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 470
uuuaacaaac guggacgua                                                    19

<210> SEQ ID NO 471
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 471
uccagucuag cauagaacc                                                    19

<210> SEQ ID NO 472
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 472
uucuugccuc gcuguaaac                                                    19

<210> SEQ ID NO 473
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 473
```
uuaggacucg ucuguccuu                                              19

<210> SEQ ID NO 474
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 474
ucauacaucg ggcacuucu                                              19

<210> SEQ ID NO 475
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 475
uuuuccuacg aauuucaac                                              19

<210> SEQ ID NO 476
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 476
uuuagagggg uguuacuua                                              19

<210> SEQ ID NO 477
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 477
ugucugcauu cgcuccuaa                                              19

<210> SEQ ID NO 478
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 478
ucaaugguua gaccaucug                                              19

<210> SEQ ID NO 479
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 479
uaccaucguc uagauaugg                                              19

<210> SEQ ID NO 480
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 480
ucuaaaacca ucgucuaga                                                19

<210> SEQ ID NO 481
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 481
uacuaaaaac gcucuugua                                                19

<210> SEQ ID NO 482
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 482
ucauucguaa agcuuagau                                                19

<210> SEQ ID NO 483
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 483
uuaucucuua gcggcuucc                                                19

<210> SEQ ID NO 484
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 484
ucgcucaucg aauuuagau                                                19

<210> SEQ ID NO 485
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 485
ugcgcucauc gaauuuaga                                                19

<210> SEQ ID NO 486
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 486
ucgcgcucau cgaauuuag                                                19
```

```
<210> SEQ ID NO 487
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 487
ucuugucgaa cguuuuaaa                                                19

<210> SEQ ID NO 488
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 488
uuccuugucg aacguuuua                                                19

<210> SEQ ID NO 489
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 489
uaguccuugu cgaacguuu                                                19

<210> SEQ ID NO 490
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 490
ugugccguua acguucaua                                                19

<210> SEQ ID NO 491
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 491
uaugcugugc cguuaacgu                                                19

<210> SEQ ID NO 492
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 492
uuuauucguc uacacaggu                                                19

<210> SEQ ID NO 493
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 493
uccacucguu ggaaugauu                                              19

<210> SEQ ID NO 494
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 494
uaaugucguu auaaacuug                                              19

<210> SEQ ID NO 495
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 495
ugcaaugucg uuauaaacu                                              19

<210> SEQ ID NO 496
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 496
uuuucucgaa aucggagcg                                              19

<210> SEQ ID NO 497
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 497
ugucauuucu cgaaaucgg                                              19

<210> SEQ ID NO 498
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 498
ugagccauuc gagagauuu                                              19

<210> SEQ ID NO 499
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 499
uuaacucgag guucaugaa                                              19

```
<210> SEQ ID NO 500
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 500
ucucuaacuc gagguucau                                                19

<210> SEQ ID NO 501
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 501
uugcaucuuc gcagcuuag                                                19

<210> SEQ ID NO 502
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 502
uuuugcaucu ucgcagcuu                                                19

<210> SEQ ID NO 503
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 503
uccacuaagc auaaccuag                                                19

<210> SEQ ID NO 504
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 504
ucauggagug uagcaucca                                                19

<210> SEQ ID NO 505
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 505
uagguccuug auaccaaca                                                19

<210> SEQ ID NO 506
<211> LENGTH: 19
<212> TYPE: RNA
<213> ORGANISM: Artificial Sequence
<220> FEATURE:
<223> OTHER INFORMATION: Synthetic Polynucleotide
```

-continued

```
<400> SEQUENCE: 506
uuucaauagg gcauugaga                                                19

<210> SEQ ID NO 507
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 507
uuacaaguug ggauccucu                                                19

<210> SEQ ID NO 508
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 508
uuuauuucga uaguuucug                                                19

<210> SEQ ID NO 509
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 509
ucuccuggua uaagugcuu                                                19

<210> SEQ ID NO 510
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 510
uauguucaau agggcauug                                                19

<210> SEQ ID NO 511
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 511
uagccaucuu acuacagcc                                                19

<210> SEQ ID NO 512
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 512
ugcagcuaca aguugggau                                                19

<210> SEQ ID NO 513
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 513
ucaguacucg auauaucaa                                                    19

<210> SEQ ID NO 514
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 514
uuuucucgag uacagaggu                                                    19

<210> SEQ ID NO 515
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 515
uccaacaaau cgcaaguaa                                                    19

<210> SEQ ID NO 516
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 516
uuccaacaaa ucgcaagua                                                    19

<210> SEQ ID NO 517
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 517
ugguagucga gggcuuuua                                                    19

<210> SEQ ID NO 518
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 518
uucugccguu gucaauuac                                                    19

<210> SEQ ID NO 519
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 519
```
ucucugccgu ugucaauua                                                19

<210> SEQ ID NO 520
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 520
ucuaagguaa acgggcaaa                                                19

<210> SEQ ID NO 521
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 521
uuguuaucga gugguucua                                                19

<210> SEQ ID NO 522
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 522
uguguuaucg agugguucu                                                19

<210> SEQ ID NO 523
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 523
ugguguuauc gagugguuc                                                19

<210> SEQ ID NO 524
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 524
uuugguguua ucgaguggu                                                19

<210> SEQ ID NO 525
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 525
uagauggacg cauuauuuu                                                19

<210> SEQ ID NO 526
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 526
ucagauggac gcauuauuu                                                    19

<210> SEQ ID NO 527
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 527
uucagaugga cgcauuauu                                                    19

<210> SEQ ID NO 528
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 528
uuucagaugg acgcauuau                                                    19

<210> SEQ ID NO 529
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 529
uaguuucucg aguacagag                                                    19

<210> SEQ ID NO 530
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 530
ucaaaguuuc ucgaguaca                                                    19

<210> SEQ ID NO 531
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 531
uguagguaau gggucacac                                                    19

<210> SEQ ID NO 532
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 532
uacucauagg caccaacau                                                    19
```

```
<210> SEQ ID NO 533
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 533
uauacucaua ggcaccaac                                                 19

<210> SEQ ID NO 534
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 534
uuaagguaaa cgggcaaag                                                 19

<210> SEQ ID NO 535
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 535
uuacuuucgc caagugaca                                                 19

<210> SEQ ID NO 536
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 536
uuuuuacuuu cgccaagug                                                 19

<210> SEQ ID NO 537
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 537
ucucuagucc aagacaucu                                                 19

<210> SEQ ID NO 538
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 538
uugucucuag uccaagaca                                                 19

<210> SEQ ID NO 539
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 539
uaaaaaucga acuucuggu                                              19

<210> SEQ ID NO 540
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 540
ugcuaaaccu aucagcuuc                                              19

<210> SEQ ID NO 541
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 541
uaagcacacu aagggcuuu                                              19

<210> SEQ ID NO 542
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 542
uuaauggacc aacucuuua                                              19

<210> SEQ ID NO 543
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 543
ugacgacaua uaaacggcc                                              19

<210> SEQ ID NO 544
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 544
uagacgacau auaaacggc                                              19

<210> SEQ ID NO 545
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 545
uacuuacgac aaagcuaca                                              19

<210> SEQ ID NO 546

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 546
uaacuuacga caaagcuac                                                19

<210> SEQ ID NO 547
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 547
uuaacuuacg acaaagcua                                                19

<210> SEQ ID NO 548
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 548
uauaacuuac gacaaagcu                                                19

<210> SEQ ID NO 549
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 549
ucauaacuua cgacaaagc                                                19

<210> SEQ ID NO 550
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 550
uaacaacgcu cucaaccag                                                19

<210> SEQ ID NO 551
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 551
uuaaacaacg cucucaacc                                                19

<210> SEQ ID NO 552
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 552
```

| | |
|---|---|
| uucagucgca agacagaac | 19 |

<210> SEQ ID NO 553
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 553

| | |
|---|---|
| ugaucagucg caagacaga | 19 |

<210> SEQ ID NO 554
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 554

| | |
|---|---|
| uaagaucagu cgcaagaca | 19 |

<210> SEQ ID NO 555
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 555

| | |
|---|---|
| uagaucaguc gcaagacag | 19 |

<210> SEQ ID NO 556
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 556

| | |
|---|---|
| ugaagaucag ucgcaagac | 19 |

<210> SEQ ID NO 557
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 557

| | |
|---|---|
| uaguaacgga uaggacaac | 19 |

<210> SEQ ID NO 558
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 558

| | |
|---|---|
| uucaguaacg gauaggaca | 19 |

<210> SEQ ID NO 559
<211> LENGTH: 19
<212> TYPE: RNA

<213> ORGANISM: Artificial Sequence
<220> FEATURE:
<223> OTHER INFORMATION: Synthetic Polynucleotide

<400> SEQUENCE: 559
ugguguuauc gagugguuc                                                19

<210> SEQ ID NO 560
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 560
uagcuagauc uaccucaca                                                19

<210> SEQ ID NO 561
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 561
ugaagcuaga ucuaccuca                                                19

<210> SEQ ID NO 562
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 562
uaugaagcua gaucuaccu                                                19

<210> SEQ ID NO 563
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 563
uggauuggau accuuaaga                                                19

<210> SEQ ID NO 564
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 564
uauuggauac cuuaagaug                                                19

<210> SEQ ID NO 565
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 565
uaccuaugcu agucaagag                                                19

```
<210> SEQ ID NO 566
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 566
ucagaccuau gcuagucaa                                                      19

<210> SEQ ID NO 567
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 567
uaacagaccu augcuaguc                                                      19

<210> SEQ ID NO 568
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 568
uauuaaacaa cgcucucaa                                                      19

<210> SEQ ID NO 569
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 569
uguaacggau aggacaacc                                                      19

<210> SEQ ID NO 570
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 570
uuucaguaac ggauaggac                                                      19

<210> SEQ ID NO 571
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 571
ucuuucagua acggauagg                                                      19

<210> SEQ ID NO 572
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 572
uaagacgaca uauaaacgg                                                    19

<210> SEQ ID NO 573
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 573
uaacuacgua cuuucaccu                                                    19

<210> SEQ ID NO 574
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 574
ucaacuacgu acuuucacc                                                    19

<210> SEQ ID NO 575
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 575
uacaacuacg uacuuucac                                                    19

<210> SEQ ID NO 576
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 576
uagacaacua cguacuuuc                                                    19

<210> SEQ ID NO 577
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 577
uuccaucgua auguguuca                                                    19

<210> SEQ ID NO 578
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 578
uauccaucgu aauguguuc                                                    19

```
<210> SEQ ID NO 579
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 579
ucauccaucg uaauguguu                                                    19

<210> SEQ ID NO 580
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 580
uucauccauc guaaugugu                                                    19

<210> SEQ ID NO 581
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 581
uaucauccau cguaaugug                                                    19

<210> SEQ ID NO 582
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 582
ucaucaucca ucguaaugu                                                    19

<210> SEQ ID NO 583
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 583
uauugccgga ugcugaaua                                                    19

<210> SEQ ID NO 584
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 584
uaacuacgau aaguccauu                                                    19

<210> SEQ ID NO 585
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 585
ucaacuacga uaaguccau                                                19

<210> SEQ ID NO 586
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 586
uuaucacgga ccaccuuaa                                                19

<210> SEQ ID NO 587
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 587
uuuaucacgg accaccuua                                                19

<210> SEQ ID NO 588
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 588
uauuaucacg gaccaccuu                                                19

<210> SEQ ID NO 589
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 589
uaauuaucac ggaccaccu                                                19

<210> SEQ ID NO 590
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 590
uuaauuauca cggaccacc                                                19

<210> SEQ ID NO 591
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 591
uaacuuacga aagacaacu                                                19

<210> SEQ ID NO 592
<211> LENGTH: 19

```
<212> TYPE: RNA
<213> ORGANISM: Artificial Sequence
<220> FEATURE:
<223> OTHER INFORMATION: Synthetic Polynucleotide

<400> SEQUENCE: 592
uuaacuuacg aaagacaac                                              19

<210> SEQ ID NO 593
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 593
uuaaguccau ugccggaug                                              19

<210> SEQ ID NO 594
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 594
ugauauuauu cggaacacc                                              19

<210> SEQ ID NO 595
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 595
uggauauuau ucggaacac                                              19

<210> SEQ ID NO 596
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 596
uucacggacc accuuaaau                                              19

<210> SEQ ID NO 597
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 597
uaucacggac caccuuaaa                                              19

<210> SEQ ID NO 598
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 598
```
uuuaauuauc acggaccac                                      19

<210> SEQ ID NO 599
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 599
uuuuaggtaa ggcaguaag                                      19

<210> SEQ ID NO 600
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 600
uuuuuaggua aggcaguaa                                      19

<210> SEQ ID NO 601
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 601
uauaagucca uugccggau                                      19

<210> SEQ ID NO 602
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 602
uacgauaagu ccauugccg                                      19

<210> SEQ ID NO 603
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 603
uccaacuaag cgaauggcu                                      19

<210> SEQ ID NO 604
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 604
uuccauuacg caacugagc                                      19

<210> SEQ ID NO 605
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 605
uuuaaacggg ucaucaaac                                              19

<210> SEQ ID NO 606
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 606
uuuuaaacgg gucaucaaa                                              19

<210> SEQ ID NO 607
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 607
uucgucugcg uuuaguaaa                                              19

<210> SEQ ID NO 608
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 608
uuuuucgucu gcguuuagu                                              19

<210> SEQ ID NO 609
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 609
ucuuccguua cgaaagucc                                              19

<210> SEQ ID NO 610
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 610
uaaucguuag cgcuccuuc                                              19

<210> SEQ ID NO 611
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 611
ucaccucagu acgaaacuc                                              19
```

```
<210> SEQ ID NO 612
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 612
uuugaaaccg auuauggau                                                19

<210> SEQ ID NO 613
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 613
uauuagguuc ucguguaaa                                                19

<210> SEQ ID NO 614
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 614
uucaccggaa uucgaucac                                                19

<210> SEQ ID NO 615
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 615
ucgaggcgua uuuauagac                                                19

<210> SEQ ID NO 616
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 616
uaacauauug ccgaccuca                                                19

<210> SEQ ID NO 617
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 617
uguagauucc guaacuuua                                                19

<210> SEQ ID NO 618
<211> LENGTH: 19
<212> TYPE: RNA
<213> ORGANISM: Artificial Sequence
<220> FEATURE:
<223> OTHER INFORMATION: Synthetic Polynucleotide
```

<400> SEQUENCE: 618
ucugaggcaa acgaaacau                                                    19

<210> SEQ ID NO 619
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 619
uaguguucgc agacaaagu                                                    19

<210> SEQ ID NO 620
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 620
uucguucuuc cgcucaaau                                                    19

<210> SEQ ID NO 621
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 621
uauagcagcg ggaucagaa                                                    19

<210> SEQ ID NO 622
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 622
uuacuccagu cguuucaca                                                    19

<210> SEQ ID NO 623
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 623
uucacaaaua cgacugcuu                                                    19

<210> SEQ ID NO 624
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 624
uuuaagccuu cggugccuu                                                    19

<210> SEQ ID NO 625

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 625
uaagcaccgc uugagauuu                                          19

<210> SEQ ID NO 626
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 626
uucagcuucc gcuaagaug                                          19

<210> SEQ ID NO 627
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 627
uuuuggccua cucaagcuc                                          19

<210> SEQ ID NO 628
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 628 uuucggucu acguaaaca                                           19

<210> SEQ ID NO 629
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 629
uucuucacca cgaacugcu                                          19

<210> SEQ ID NO 630
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 630
uacuuaacgc uaagcaaua                                          19

<210> SEQ ID NO 631
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 631
```

-continued

| | |
|---|---|
| uguauuaauu cggggcucu | 19 |

<210> SEQ ID NO 632
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 632

| | |
|---|---|
| uaaauggcgg acuucucc | 19 |

<210> SEQ ID NO 633
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 633

| | |
|---|---|
| ugggaauacc ucuaguucu | 19 |

<210> SEQ ID NO 634
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 634

| | |
|---|---|
| uauaaagcgc acggaugga | 19 |

<210> SEQ ID NO 635
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 635

| | |
|---|---|
| ugauuuaagg cugguaucc | 19 |

<210> SEQ ID NO 636
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 636

| | |
|---|---|
| uagucggcuc gauuuaagg | 19 |

<210> SEQ ID NO 637
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 637

| | |
|---|---|
| uuagucggcu cgauuuaag | 19 |

<210> SEQ ID NO 638
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 638
uguagucggc ucgauuuaa                                                    19

<210> SEQ ID NO 639
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 639
uauuccgcug aagccaacu                                                    19

<210> SEQ ID NO 640
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 640
uguagguauu ccgcugaag                                                    19

<210> SEQ ID NO 641
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 641
uaguagguau uccgcugaa                                                    19

<210> SEQ ID NO 642
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 642
ucaaucggcu uguugaaua                                                    19

<210> SEQ ID NO 643
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 643
uucaaucggc uuguugaau                                                    19

<210> SEQ ID NO 644
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 644
uaucaaucgg cuuguugaa                                                    19
```

```
<210> SEQ ID NO 645
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 645
ugaucaaucg gcuuguuga                                                19

<210> SEQ ID NO 646
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 646
uugaucaauc ggcuuguug                                                19

<210> SEQ ID NO 647
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 647
ugugaucaau cggcuuguu                                                19

<210> SEQ ID NO 648
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 648
uugugaucaa ucggcuugu                                                19

<210> SEQ ID NO 649
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 649
uaugugauca aucggcuug                                                19

<210> SEQ ID NO 650
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 650
uagccauaag gguaaggga                                                19

<210> SEQ ID NO 651
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 651
uuagccauaa ggguaaggg                                                  19

<210> SEQ ID NO 652
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 652
uuuagccaua aggguaagg                                                  19

<210> SEQ ID NO 653
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 653
ucgauuuaag gcugguauc                                                  19

<210> SEQ ID NO 654
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 654
uuuuagccau aaggguaag                                                  19

<210> SEQ ID NO 655
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 655
ugaauaccuc uaguucuuc                                                  19

<210> SEQ ID NO 656
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 656
uggaauaccu cuaguucuu                                                  19

<210> SEQ ID NO 657
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 657
uucgauuuaa ggcugguau                                                  19

```
<210> SEQ ID NO 658
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 658
ucucgauuua aggcuggua                                                  19

<210> SEQ ID NO 659
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 659
uaaugugauc aaucggcuu                                                  19

<210> SEQ ID NO 660
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 660
uugcacugcu agagcugaa                                                  19

<210> SEQ ID NO 661
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 661
uuugcacugc uagagcuga                                                  19

<210> SEQ ID NO 662
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 662
uugcugucau aagaucaaa                                                  19
```